United States Patent
Nordvall et al.

(10) Patent No.: US 11,840,524 B2
(45) Date of Patent: Dec. 12, 2023

(54) 4-SUBSTITUTED PHENYL-1,3,5-TRIAZINE DERIVATIVES AS MODULATORS OF TRK RECEPTORS

(71) Applicant: ALZECURE PHARMA AB, Huddinge (SE)

(72) Inventors: Gunnar Nordvall, Rönninge (SE); Pontus Forsell, Huddinge (SE)

(73) Assignee: ALZECURE PHARMA AB, Huddinge (SE)

(*) Notice: Subject to any disclaimer, the term of this patent is extended or adjusted under 35 U.S.C. 154(b) by 55 days.

(21) Appl. No.: 17/255,642

(22) PCT Filed: Jun. 28, 2019

(86) PCT No.: PCT/GB2019/051853
§ 371 (c)(1),
(2) Date: Dec. 23, 2020

(87) PCT Pub. No.: WO2020/002950
PCT Pub. Date: Jan. 2, 2020

(65) Prior Publication Data
US 2021/0371402 A1    Dec. 2, 2021

(30) Foreign Application Priority Data
Jun. 28, 2018  (GB) ..................... 1810668

(51) Int. Cl.
*C07D 403/10* (2006.01)
*A61K 45/06* (2006.01)
*C07D 403/12* (2006.01)

(52) U.S. Cl.
CPC ............ *C07D 403/10* (2013.01); *A61K 45/06* (2013.01); *C07D 403/12* (2013.01)

(58) Field of Classification Search
CPC ..... C07D 403/10; C07D 403/12; A61P 25/28; A61K 31/53; A61K 45/06
See application file for complete search history.

(56) References Cited

U.S. PATENT DOCUMENTS

| | | | |
|---|---|---|---|
| 3,933,814 A | 1/1976 | Haberkorn et al. | |
| 3,948,893 A | 4/1976 | Aichinger et al. | |
| 3,966,725 A | 6/1976 | Reisdorff et al. | |
| 4,219,552 A | 8/1980 | Haberkorn et al. | |
| 4,837,216 A | 6/1989 | Mehlhorn et al. | |
| 4,874,860 A | 10/1989 | Gallenkamp et al. | |
| 4,933,341 A | 6/1990 | Lindner et al. | |
| 5,519,133 A | 5/1996 | Crews et al. | |
| 5,604,180 A | 2/1997 | Crews et al. | |
| 5,679,791 A | 10/1997 | Crews, Jr. et al. | |
| 5,726,126 A | 3/1998 | Crews et al. | |
| 6,465,460 B1 | 10/2002 | Hundley et al. | |
| 2003/0186320 A1 | 10/2003 | Yu | |
| 2020/0113910 A1 | 4/2020 | Nordvall et al. | |
| 2020/0399230 A1 | 12/2020 | Nordvall et al. | |
| 2021/0261513 A1 | 8/2021 | Nordvall et al. | |
| 2022/0306589 A1 | 9/2022 | Nordvall et al. | |
| 2022/0324819 A1 | 10/2022 | Nordvall et al. | |

FOREIGN PATENT DOCUMENTS

| | | |
|---|---|---|
| CN | 105209427 A | 12/2015 |
| DE | 2246109 | 3/1974 |
| DE | 2718799 | 11/1978 |
| DE | 3314739 | 10/1984 |
| DE | 3408768 | 9/1985 |
| DE | 3516631 | 11/1986 |
| DE | 3516632 | 11/1986 |
| DE | 4000624 | 1/1990 |
| DE | 19958388 | 6/2001 |
| EP | 0081142 | 6/1983 |
| EP | 0279219 | 8/1988 |
| EP | 0334135 | 9/1989 |
| EP | 0339555 | 11/1989 |

(Continued)

OTHER PUBLICATIONS

Bailey et al. Tropomyosin receptor kinase inhibitors: an updated patent review for 2010-2016—Part I. *Expert opinion on therapeutic patents*, 27, 6(8), 733-751 (2017).

Bartus R.T., On neurodegenerative diseases, models, and treatment strategies: lessons learned and lessons forgotten a generation following the cholinergic hypothesis. *Exp. Neurol.*, 2000, 163, 495-529.

Blurton-Jones M., Neural stem cells improve cognition via BDNF in a transgenic model of Alzheimer disease. *PNAS*, 2009, 106, 32, 13594-13599.

Boots et al, BDNF Val66Met predicts cognitive decline in the Wisconsin Registry for Alzheimer's Prevention. *Neurology*, 2017, 88, 1-9.

Calabrese et al., Modulation of neuroplastic molecules in selected brain regions after chronic administration of the novel antidepressant agomelatine . . . *Psychopharmacology*, 2011, 215, 267-275.

(Continued)

*Primary Examiner* — Kortney L. Klinkel
*Assistant Examiner* — Padmaja S Rao
(74) *Attorney, Agent, or Firm* — Parker Highlander PLLC

(57) ABSTRACT

There is provided a compound of formula (I), wherein $R^1$, $R^2$, $R^3$, $Q^1$, $Q^2$, $Q^3$, X, A and n are as defined herein, which compounds are useful in the treatment of diseases characterised by impaired signalling of neurotrophins and/or other trophic factors, such as Alzheimer's disease and the like.

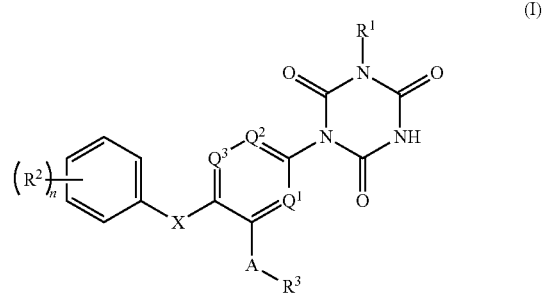

33 Claims, No Drawings

(56) References Cited

FOREIGN PATENT DOCUMENTS

| | | |
|---|---|---|
| EP | 0640600 | 3/1995 |
| EP | 0745595 | 12/1996 |
| EP | 1157991 | 11/2001 |
| GB | 1571368 | 7/1980 |
| SE | 402103 | 6/1978 |
| WO | WO 2000/37084 | 6/2000 |
| WO | WO 01/10862 | 2/2001 |
| WO | WO 02/06277 | 1/2002 |
| WO | WO 02/13831 | 2/2002 |
| WO | WO 02/14288 | 2/2002 |
| WO | WO 03/011839 | 2/2003 |
| WO | WO 03/101980 | 12/2003 |
| WO | WO 2004/007499 | 1/2004 |
| WO | WO 2008/019785 | 2/2008 |
| WO | WO 2008/148008 | 12/2008 |
| WO | WO 2011/150347 A2 | 12/2011 |
| WO | WO 2014/144342 A1 | 9/2014 |
| WO | WO 2015/107053 | 7/2015 |
| WO | WO 2016/094682 | 6/2016 |
| WO | WO 2018/115891 | 6/2018 |

OTHER PUBLICATIONS

Castrén E. et al., Brain-derived neurotrophic factor in mood disorders and antidepressant treatments. *Neurobiol Dis.* 2017, 119-126.
Castrén E., Neurotrophins and psychiatric disorders. *Handb. Exp. Pharmacol.*, 2014, 220, 461-479.
Chaldakov G, The metabotrophic NGF and BDNF: an emerging concept. *Arch Ital Biol.* 2011, 149, 257-63.
Chen et al., Brain-derived neurotrophic factor accelerates gut motility in slow-transit constipation. *Acta. Physiol.*, 2014, 212(3), 226-238.
Coulie B., et al., Medical Management of Constipation. *Gastroenterology,* 2000, 119(1), 41-50.
Gasparini et al., Effects of Aerobic Exercise on Mild Cognitive Impairment. A Controlled Trial. *Trends Neurosci.*, 2003, 26(8), 404-6.
Guo et al., The synthesis and antioxidant activity of the Schiff bases of chitosan and carboxymethyl chitosan. Biorg. Med. Chem. Lett., 2005, 15(3), 693-698.
Hoshaw et al., Central administration of IGF-I and BDNF leads to long-lasting antidepressant-like effects. *Brain Res.*, 2005, 1037, 204-208.
Lihama, T et al, Regiospecific Syntheses of All Isomeric Nitrofluorenones and Nitrofluorenes by Transition Metal Catalyzed Cross-Coupling Reactions. *Synthesis*, 3, 184-8, 1989.
Kim et al. Pharmacokinetics and Metabolism of Toltrazuil and Its Major Metabolites after Oral Administration in Broilers. J Poult. Sci. 2013, Marc., vol. 50, No. 3, 257-261.
Li JS et al., Modulation of FGF receptor signaling as an intervention and potential therapy for myelin breakdown in Alzheimer's disease. *Med Hypotheses,* 2013, 80, 341-4.
Lim et al., "BDNF Val66Met moderates memory impairment, hippocampal function and tau in preclinical autosomal dominant Alzheimer's disease." *Brain,* 2016, 139(10), 2766-2777.
Lucidi-Phillipi CA et al., TrkA activation is sufficient to rescue axotomized cholinergic neurons. *Neuron.*, 1996, 16, 653-663.
A controlled trial of recombinant methionyl human BDNF in ALS: The BDNF Study Group (Phase III). *Neurology,* 1999, 52(7), 1427.
Paibir, S. G. et al., High-performance liquid chromatographic analysis of phenobarbital and phenobarbital metabolites in human urine. *J. Chromatogr.* B, Mar. 1997, vol. 691, No. 1, p. 111-117.
Shimizu et al., Alterations of serum levels of brain-derived neurotrophic factor (BDNF) in depressed patients with or without antidepressants. *Biological Psychiatry,* 2003, 70-75.
Sen et al., Serum brain-derived neurotrophic factor, depression, and antidepressant medications: meta-analyses and implications. *Biological Psychiatry,* 2008, 527-532.
Senda, S. et al., "Uracil derivatives and related compounds. VII. Synthesis and anti-inflammatory activity of bucolome's related compounds" In: Yakugaku Zasshi, 1969, vol. 89, No. 2, p. 254-259.
Suzuki et al. Identification of approved drugs that inhibit the binding of amyloid β oligomers to ephrin type-B receptor 2 . . . *FEBS Open Bio,* 2016, 6 461-468.
Tsoka et al, "Effects of BNN27, a Novel C17-Spiroepoxy Steroid Derivative, on Experimental Retinal Detachment-Induced Photoreceptor Cell Death", 8:10661, pp. 1-12 (2018).
Yeo, GS. et al., A de novo mutation affecting human TrkB associated with severe obesity and developmental delay. *Nat. Neurosci.*, 2004, 7, 1187-1189.
Wellmer A. et al., A double-blind placebo-controlled clinical trial of recombinant human brain-derived neurotrophic factor (rhBDNF) in diabetic polyneuropathy.*J. Peripher. Nerv. Syst.,* 2001, 6(4), 204-210.
Zhang et al. Roles of brain-derived neurotrophic factor/tropomyosin-related kinase B (BONE/TrkB) signalling in Alzheimer's disease. *Journal of Clinical Neuroscience,* vol. 19, No. 7, 2012, 946-949.
Office Action issued in Russian Application No. 2019120431 based on PCT/GB2017/053868, dated Mar. 9, 2021, and English language translation thereof.
O. A. Gomazkov "Neurotrophins: therapeutic potential and the concept of «minipeptides»", Neurochemistry, vol. 29, 3, 2012, 189-199. And English language translation thereof.
Non-Final Office Action issued in U.S. Appl. No. 17/255,632, dated Nov. 16, 2021.
Restriction Requirement issued in U.S. Appl. No. 16/471,923, dated May 1, 2020.
Non-Final Office Action issued in U.S. Appl. No. 16/471,923, dated Aug. 11, 2020.
Restriction Requirement issued in U.S. Appl. No. 16/975,437, dated Aug. 6, 2021.
Non-Final Office Action issued in U.S. Appl. No. 16/975,437, dated Sep. 17, 2021.
Machine translation of Russian Office Action issued in Russian application No. 2020126542 (based on PCT application No. PCT/GB2019/050523), dated Sep. 14, 2022.
Dyson G. et al., "Chemistry of Synthetic drugs substances", translated from English M: "Mir" 1964, pp. 12-19. (available in Russian language; relevance provided in the transmittal letter).
Fundamentals of medical prevention. Educational Methodological Manual for Students and Cadets of Cycles Professional Development of State Professional Educational Institutions Novosibirsk, 2016, UDC 614.2-084, BBC 51.1(2)2, pp. 13-21. (available in Russian language; relevance provided in the transmittal letter).
*Short Course of Molecular Pharmacology* edited by P.V. Sergeeva, M., 1975, p. 10. (available in Russian language; relevance provided in the transmittal letter).
Kholodov, L. E. et al., "Clinical pharmacokinetics," *Medicine,* 1985, pp. 83-98, 134-138, 160, 378-380. (available in Russian language; relevance provided in the transmittal letter).
Guidelines for conducting preclinical studies of drugs Part one.-M; Drig and K, 2012, 944s, edited by Mironov A.N. (available in Russian language; relevance provided in the transmittal letter).
Chou, T-C, "Drug Combination Studies and Their Synergy Quantification Using the Chou-Talalay Method," *Cancer Research;* 70.2 (2010): 440-446.
Kharkevich, D. A., Pharmacology Textbook, 2010, 20th edition, pp. 77-82. (available in Russian language; relevance provided in the transmittal letter).
Mashkovsky, Medicines, 14th Ed., vol. 1, Moscow, 2001, p. 11. (available in Russian language; relevance provided in the transmittal letter).
Vengerovsky, A. I., Pharmacological incompatibility/Bulletin of Siberian Medicine, 2003, 3, pp. 49-56. (available in Russian language; relevance provided in the transmittal letter).
Translation of Office Action issued in Chinese patent application No. 2019800147986 (based on PCT application No. PCT/GB2019/050523), dated Dec. 29, 2022.
Silverman, Richard B., The Organic Chemistry of Drug Design and Drug Action, $2^{nd}$ Ed, published Jan. 2008, pp. 17-23. (available in Chinese language; relevance provided in the transmittal letter).

(56) References Cited

OTHER PUBLICATIONS

Ghilardi, J. R. et al., "Sustained blockade of neurotrophin receptors TrkA, TrkB and TrkC reduces non-malignant skeletal pain but not the maintenance of sensory and sympathetic nerve fibers," *Bone,* 48 (2011): 389-398.

Damasio, A. R., "Alzheimer's Disease and Related Dementias," *Textbook of Medicine,* 20$^{th}$ edition, 2 (1997): 1992-1996.

Layzer, R. B. "Section Five-Degenerative Diseases of the Nervous System," *Textbook of Medicine,* 20$^{th}$ edition, 2 (1997): 2050-2057.

U.S. Appl. No. 17/172,516, filed Feb. 10, 2021; first inventor Gunnar Nordvall; 68 pages.

U.S. Appl. No. 17/329,777, filed May 25, 2021; first inventor Gunnar Nordvall; 67 pages.

Fusheng L. et al., "The role of brain-derived neurotrophic factor in Alzheimer's disease," *Practical Preventative Medicine,* 14.4 (2007): 1320-1323.

4-SUBSTITUTED PHENYL-1,3,5-TRIAZINE DERIVATIVES AS MODULATORS OF TRK RECEPTORS

This application is a national phase application under 35 U.S.C. § 371 of International Application No. PCT/GB2019/051853 filed Jun. 28, 2019, which claims priority to United Kingdom Application No. 1810668.2, filed Jun. 28, 2018. The entire text of each of the above referenced disclosures is specifically incorporated herein by reference.

FIELD OF THE INVENTION

This invention relates to novel pharmaceutically-active compounds, to pharmaceutical compositions comprising such compounds, as well as to their pharmaceutical use. In particular, the invention relates to the use of these compounds and compositions in methods for the treatment and/or prevention of diseases characterised by impaired signalling of neurotrophins and/or other trophic factors.

BACKGROUND OF THE INVENTION

The listing or discussion of an apparently prior-published document in this specification should not necessarily be taken as an acknowledgement that the document is part of the state of the art or is common general knowledge.

Nerve growth factor (NGF), Brain Derived Neurotrophic Factor (BDNF), neurotrophin-3 (NT-3) and neurotrophin-4/5 all belong to the neurotrophin protein family. These hormones act through a class of receptor tyrosine kinases called tropomyosin-receptor kinase (Trk). Ligand binding to Trks initiates receptor dimerization and autophosphorylation of the kinase domain, which activates the kinase activity of the receptor. This results in further receptor phosphorylation at Tyr490, Tyr751 and Tyr785 of TrkA (or their equivalent residues in other Trk receptors). This phosphorylation leads to adaptor binding sites that couple the receptor to SHC adaptor protein 1 (SHC-1), phosphoinositide 3-kinase (PI3K) and phospholipase Cγ1 (PLCγ1). The coupling of adaptor proteins to the receptor initiates several different cellular events leading to e.g. neurite outgrowth and axonal elongation. These receptors, and their signalling pathways, play a pivotal role in many key processes in the brain e.g. hippocampal neurogenesis, synaptic plasticity, and long-term potentiation, a proposed mechanism underlying memory formation at the level of the synapse. Both NGF/TrkA and BDNF/TrkB-stimulated signalling is also necessary for the survival and morphogenesis of neurons.

In addition to activation of Trk-receptors by classical ligand binding, there are ligand independent events that can regulate neurotrophin signalling.

The balance between the activity of the receptor tyrosine kinase and the activity of tyrosine phosphatases intricately regulates the levels of phosphorylated receptor. Thus, protein tyrosine phosphatases such as PTP-1B or other phosphatases can increase neurotrophin signalling and regulate temporal and spatial activity of the Trk-receptor as well as receptor tyrosine kinases.

Also, adenosine and adenosine agonists can mediate phosphorylation of Trk-receptors, via a mechanism that requires the adenosine 2A (A2A) receptor. This phosphorylation of Trk-receptors is independent of ligand binding suggesting that modulation of Trk-receptor signalling can be accomplished by several different mechanisms.

Synapse loss and a decrease in the hippocampal volume are pathological signatures of Alzheimer's disease in the brain and a number of studies suggest that synapse loss is the best neuroanatomical indicator of cognitive decline in the disease. Basal forebrain cholinergic neurons (BFCN) are a subpopulation of neurons that seem to be particularly vulnerable to the pathology of AD. Dysfunctional atrophy of these neurons, which in turn results in severe loss of cortical and hippocampal innervation, may be the source for the malfunction of the cholinergic system in AD (Bartus R T Exp Neurol 2000; 163:495-529). The severe cortical cholinergic deficits in the disease also include a loss of choline acetyltransferase (ChAT) and acetylcholinesterase (AChE) activity. The basal forebrain cholinergic system is dependent on NGF and cholinergic basal forebrain neurons are the major cell group that expresses the receptor for NGF, i.e. TrkA. Although the role of NGF in cholinergic neuronal survival and function is well established, studies have also shown neuroprotective/neurorestorative effects mediated by this system, e.g. that axotomized cholinergic projections in animals can be rescued by TrkA activation (Lucidi-Phillipi C A, Neuron., 1996, 16(3):653-663).

An early morphological change in the brain of AD-patients is a decreased hippocampal volume. BDNF/TrkB-stimulated signalling has previously been shown to be necessary for survival and morphogenesis of especially hippocampal neurons. Moreover, it is widely accepted that BDNF plays a critical role in neuronal plasticity and long-term potentiation (LTP). Indeed, a growing body of experimental evidence suggests that increased BDNF signalling could potentially improve cognition in AD. The transplantation of stem cells into the brain of a triple-transgenic mouse model of AD, that expresses amyloid and tau pathology, i.e. the major neuropathological hallmarks of AD, results in improved cognition (Blurton-Jones M, PNAS, 2009. 106(32): p. 13594-13599). This effect is mediated by BDNF as gain-of-function studies show that recombinant BDNF mimics the beneficial effects of neural stem cell (NSC) transplantation. Furthermore, loss-of-function studies show that depletion of NSC-derived BDNF fails to improve cognition or restore hippocampal synaptic density.

Given the potent neuroprotective and neurorestorative effects of the TrkA/NGF and TrkB/BDNF systems, small molecule positive modulators of neurotrophin signalling might be beneficial in treating a number of diseases with neurodegeneration including, but not limited to, Alzheimer's disease, Lewy body dementia, frontotemporal dementia, HIV dementia, Huntington's disease, amyotrophic lateral sclerosis and other motor neuron diseases, Rett syndrome, epilepsy, Parkinson's disease and other parkinsonian disorders. The modulators can also be used in the treatment of diseases where enhancement of nerve regeneration is beneficial, such as demyelinating diseases including, but not limited to, multiple sclerosis. The modulators could also be used for neuroprotection before or after an insult such as spinal cord injury, stroke, hypoxia, ischemia, brain injury including traumatic brain injury. Moreover, the important role of these neurotrophin systems in synaptic plasticity is thought to mediate learning and memory processes, and indicates that the modulators could also be used in disorders where cognitive function is impaired, including, but not limited to, mild cognitive impairment, dementia disorders (including dementia of mixed vascular and degenerative origin, presenile dementia, senile dementia and dementia associated with Parkinson's disease, progressive supranuclear palsy or corticobasal degeneration) and cognitive dysfunction in schizophrenia.

Recent data have also indicated that NGF/TrkA and BDNF/TrkB systems may operate as metabotrophins, that is, be involved in the maintenance of cardiometabolic homeostasis (glucose and lipid metabolism as well as energy balance, cardioprotection, and wound healing) (Chaldakov G, Arch. Ital. Biol. 2011 June 149(2):257-63). In fact, mutations in the genes encoding BDNF and its receptor TrkB have been shown to lead to severe obesity in humans (Yeo, G S. et al. Nat. Neurosci. 2004, 7, 1187-1189). Therefore, indications such as atherosclerosis, obesity, diabetes and metabolic syndrome could also benefit from NGF/TrkA and BDNF/TrkB directed therapies.

Another area of interest when it comes to neurotrophin signalling is neuropsychiatric disorders (Castrén E et al., Neurobiol Dis. 2016 Jul. 15, 30169-3). Studies have, for example, clearly demonstrated that depressed patients have reduced serum BDNF levels, which are restored after successful recovery (Shimizu et al., 2003, Sen et al., 2008). Moreover, several studies have demonstrated that chronic treatment with various antidepressant drugs increase BDNF mRNA and protein levels in the cerebral cortex and hippocampus (Calabrese et al., Psychopharmacology, 2011, 215, pp. 267-275). Also, local administration of BDNF into the brain has been shown to reduce depression-like behavior and mimic the effects of antidepressants (Hoshaw et al., Brain Res., 2005, 1037, pp. 204-208). Notably, the role for BDNF does not seem to be restricted to depression; it has also been implicated in other disorders, such as anxiety and schizophrenia (Castrén E., Handb. Exp. Pharmacol., 2014, 220, pp. 461-479). These data suggest that therapies targeting neurotrophin systems e.g. NGF/TrkA and BDNF/TrkB could have a therapeutic effect in several neuropsychiatric disorders, including, but not limited to, depression, schizophrenia and anxiety.

It has also been demonstrated that both BDNF and NT3 stimulate gastrointestinal motility, accelerate colonic transit time and relieve constipation in humans (Coulie B., et al., Gastroenterology, 2000, 119(1), 41-50). The levels of BDNF in colonic biopsies from patients with slow-transit constipation have also been found to be reduced compared to healthy controls (Chen et al., Acta. Physiol., 2014, 212(3), 226-238). Furthermore, one of the observed adverse events in a large phase 3 clinical trial with >1,000 patients with the neurological disorder amyotrophic lateral sclerosis undergoing treatment with recombinant BDNF was increased gut motility, diarrhoea and relief of constipation (Neurology, 1999, 52(7), 1427). A similar observation was also made in a smaller clinical trial of BDNF in patients with diabetic neuropathy (Wellmer A. et al., J. Peripher. Nerv. Syst., 2001, 6(4), 204-210). Preclinical models have also suggested that BDNF and NT3 may play a role in the regulation of gastrointestinal motility. BDNF+/− heterozygous mice display decreased stool frequency and increased total gastrointestinal transit time, demonstrating that lower BDNF levels reduces gastrointestinal motility. BDNF also relieved loperamide-induced constipation in mice (Chen et al., Acta. Physiol., 2014, 212(3), 226-238). Accordingly, it is believed that neurotrophins and their receptors may play an important role in maintaining normal motility and therefore that modulation of neurotrophin signaling could represent a promising strategy for improving gut motility in patients suffering from constipation.

The finding that NGF and BDNF play important roles in neuronal homeostasis in combination with their neuroprotective and neurorestorative effect makes these pathways highly suitable as candidates for drug intervention for the treatment of diseases of the central nervous system and the peripheral nervous system. However, BDNF and NGF are themselves not ideal drug candidates due to their pharmacokinetic properties, the difficulties in administration and their limited ability to cross the blood-brain barrier. This has led to several attempts to identify peptides, cyclized peptides, peptide mimetics, small molecule agonist or selective modulators of NGF or BDNF. Several natural products such as gambogic amide (and analogues thereof), deoxygedunin and 7,8-dihydroxyflavone have been demonstrated to act as TrkA or TrkB agonists. Moreover, the tricyclic depressant amitriptyline has also been shown to be a TrkA and TrkB agonist. However, there is currently no specific TrkA or TrkB agonist that has reached the market. Therefore, there is an unmet need in the art for small molecule compounds that have the ability to stimulate or modulate TrkA and/or TrkB receptors, in combination with TrkC, FGFR1 and/or IGF1R and optionally other receptor tyrosine kinases for the treatment of both neurological and non-neurological disorders. There is still a need for compounds that have an improved potency and improved selectivity to TrkA and/or TrkB receptor.

BDNF production can be affected by a polymorphism within the BDNF gene (rs6265) causes a valine (Val) to methionine (Met) substitution at codon 66 (Val66Met). This polymorphism is found in approximately 30% of Caucasians and up to 70% in Asian populations. The presence of one or two Met alleles is associated with lower BDNF production in a subject. This lower BDNF production can lead to increased cognitive decline and decreased hippocampal volume.

A study by Boots et al (Neurology, 2017, 88, 1-9) demonstrated that subjects suffering sporadic Alzheimer's disease who carry the BDNF Met allele experience a steeper decline in episodic memory and executive function than non-carriers. Greater memory decline and decreased hippocampal function have also been observed in Val66Met patients with familial Alzheimer's disease (Lim et al., Brain, 2016, 139(10), 2766-2777). The same study also showed increased tau-protein and phosphorylated tau-protein in the cerebrospinal fluid in this patient group. The decline in memory in subjects with pre-clinical or clinical Alzheimer's disease was exacerbated by greater amyloid plaque burden, thus suggesting that it is possible to treat Alzheimer's disease at various stages of the disease by potentiating the effects of BDNF in patients with the Val66Met polymorphism. Such treatment may lead to neuroprotection and increased cognitive function.

In general therefore, there remains a need for alternative and/or more effective compounds that are useful in the treatment and/or prevention of diseases characterised by impaired signalling of neurotrophins and/or other trophic factors, and in particular neurodegenerative diseases such as Alzheimer's disease.

Toltrazuril (1-methyl-3-(3-methyl-4-{4-[(trifluoromethyl)sulfanyl]phenoxy}phenyl)-1,3,5-triazinane-2,4,6-trione; Baycox®) is a triazine-based antiprotozoal compounds that are used in veterinary medicine to treat coccidial infections, such as isosporiasis, toxoplasmosis, neosporosis, and equine protozoal meningoencephalitis.

A recent study by Suzuki et al. (FEBS Open Bio 2016, 6 461-468), reported that toltrazuril inhibits the binding of β-amyloid oligomers to ephrin type-B receptor 2 (EphB2; a receptor understood to play a role memory and learning functions) by 30%. However, due to a lack selectivity for this receptor it was not selected for further studies as a potential candidate compound for the treatment of Alzheimer's disease.

Other phenyl-1,3,5-triazine derivatives are disclosed for similar use in veterinary medicine in several old patent documents, such as U.S. Pat. No. 3,933,814, SE 402 103, DE 3 408 768 A1, EP 0 081 142 A2 and 279 219 A1. There is no suggestion that any of the compounds that are disclosed in any of these documents may be used to treat human patients per se and certainly not that the compounds may be useful in the treatment and/or prevention of diseases characterised by impaired signalling of neurotrophins and/or other trophic factors, such as Alzheimer's disease.

It has now surprisingly been found that certain 4-substituted phenyl-1,3,5-triazine derivatives are positive modulators of Trk receptors (including TrkA, TrkB and TrkC) and receptor tyrosine kinases such as IGF1R and/or FGFR1, and thus have properties rendering them useful for the treatment of diseases characterised by impaired signalling of neurotrophins and/or other trophic factors, such as Alzheimer's disease. As a result of their mode of action, the compounds are thought to be particularly suitable as therapeutic agents for use in disorders such as Alzheimer's disease, for example in patients having the Val66Met mutation in the brain-derived neurotrophic factor (BDNF) gene.

DETAILED DESCRIPTION OF THE INVENTION

According to an aspect of the invention, there is provided a compound of formula I

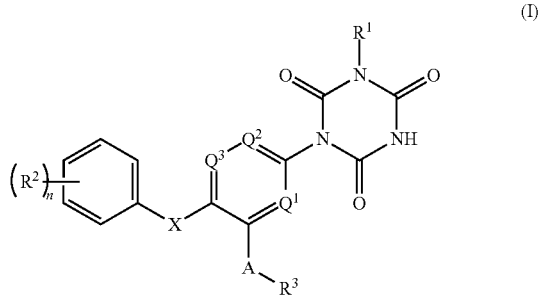

wherein:

$R^1$ represents methyl; phenyl optionally substituted by one or more groups selected from halogen, —CN, —C(O)NR$^{a1}$R$^{a2}$, —NR$^{a3}$R$^{a4}$, a 5-membered heteroaryl group, $C_{1-4}$ alkyl, $C_{1-4}$ alkoxy, $C_{1-4}$ alkoxy-$C_{1-4}$ alkyl or methylenedioxy, wherein the latter four groups are optionally substituted by one or more fluoro groups; or a 5-9-membered heteroaryl group optionally substituted by one or more groups selected from halogen, —CN, $C_{1-4}$ alkyl, $C_{1-4}$ alkoxy $C_{1-4}$ alkoxy-$C_{1-4}$ alkyl or phenyl, which latter four groups are optionally substituted by one or more fluoro groups;

$R^2$ represents halogen, hydroxy, cyano, —C(O)NR$^{a5}$R$^{a6}$, $C_{1-4}$ alkyl, $C_{1-4}$ alkoxy or $C_{1-4}$ alkoxy-$C_{1-4}$ alkyl, wherein the latter three groups are optionally substituted by one or more fluoro groups;

n represents 0, 1 or 2

$Q^1$, $Q^2$, and $Q^3$ each represent —C($R^4$)— or —N—, wherein a maximum of two of $Q^1$ to $Q^3$ represent —N—;

$R^4$ represents H, halogen, —CN, —NR$^{a7}$R$^{a8}$, $C_{1-4}$ alkyl, $C_{1-4}$ alkoxy or $C_{1-4}$ alkoxy-$C_{1-4}$ alkyl, which latter three groups are optionally substituted by one or more fluoro group;

X represents —C($R^5$)($R^6$)—, —O—, —S—, —N($R^7$)— or a direct bond;

$R^5$, $R^6$ and $R^7$ each independently represent H or $C_{1-2}$ alkyl;

A represents a direct bond, —O—, $C_{1-2}$ alkylene, —$C_{1-2}$alkyleneO—, —O$C_{1-2}$alkylene-, —N(H) $C_{1-2}$alkylene- or —$C_{1-2}$alkylene N(H)—, which latter five groups are optionally substituted by one or more halo, $C_{1-2}$ alkyl or =O groups;

$R^3$ represents a 5-6-membered heteroaryl group, optionally substituted by one or more group selected from halo, —CN, —NR$^{a9}$R$^{a10}$, —C(O)NR$^{a11}$R$^{a12}$, $C_{1-4}$ alkyl, $C_{1-4}$alkoxy or $C_{1-4}$ alkoxy-$C_{1-4}$ alkyl, which latter three groups are optionally substituted by one or more fluoro groups;

$R^{a1}$, $R^{a2}$, $R^{a3}$, $R^{a4}$, $R^{a5}$, $R^{a6}$, $R^{a7}$, $R^{a8}$, $R^{a9}$, $R^{a10}$, $R^{a11}$, and $R^{a12}$ each independently represent H or $C_{1-4}$ alkyl, which $C_{1-4}$ alkyl groups are optionally substituted by one or more fluoro groups; or $R^{a1}$ and $R^{a2}$, $R^{a3}$ and $R^{a4}$, $R^{a5}$ and $R^{a6}$, $R^{a7}$ and $R^{a8}$, $R^{a9}$ and $R^{a10}$ and $R^{a11}$ and $R^{a12}$ may independently be joined together to form, together with the atom to which they are attached, a 4- to 6-membered heterocyclyl ring, which heterocyclyl ring optionally contains one further heteroatom selected from N, O and S.

or a pharmaceutically-acceptable salt thereof, which compounds (including pharmaceutically-acceptable salts) may be referred to herein as the "compounds of the invention".

For the avoidance of doubt, the skilled person will understand that references herein to compounds of particular aspects of the invention (such as the first aspect of the invention, i.e. referring to compounds of formula I as defined in the first aspect of the invention) will include references to all embodiments and particular features thereof, which embodiments and particular features may be taken in combination to form further embodiments and features of the invention.

Unless indicated otherwise, all technical and scientific terms used herein will have their common meaning as understood by one of ordinary skill in the art to which this invention pertains.

Pharmaceutically acceptable salts include acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared using techniques known to those skilled in the art, such as by exchanging a counter-ion of a compound of the invention in the form of a salt with another counter-ion, for example using a suitable ion exchange resin.

Particular acid addition salts that may be mentioned include those formed by reaction with corresponding acids, thus protonating the compound of the invention, to form carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxy-benzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts), sulphonate salts (e.g. benzenesulphonate, methyl-, bromo- or chloro-benzenesulphonate, xylenesulphonate, methanesulphonate, ethanesulphonate, propanesulphonate, hydroxy-ethanesulphonate, 1- or 2-naphthalene-sulphonate or 1,5-naphthalene-disulphonate salts) or sulphate, pyrosulphate, bisulphate, sulphite, bisulphite, phosphate, monohydrogenphosphate, dihydrogenphosphate, metaphosphate, pyrophosphate or nitrate salts, and the like.

Particular base addition salts that may be mentioned include salts formed by reaction with corresponding bases, thus removing a proton from compounds of the invention, to form salts with alkali metals (such as Na and K salts), alkaline earth metals (such as Mg and Ca salts), organic bases (such as ethanolamine, diethanolamine, triethanolamine, tromethamine and lysine) and inorganic bases (such as ammonia and aluminium hydroxide). More particularly, base addition salts that may be mentioned include Mg, Ca and, most particularly, K and Na salts.

More particular salts that may be mentioned include Na salts.

For the avoidance of doubt, compounds of the invention may exist as solids, and thus the scope of the invention includes all amorphous, crystalline and part crystalline forms thereof, and may also exist as oils. Where compounds of the invention exist in crystalline and part crystalline forms, such forms may include solvates, which are included in the scope of the invention.

For the avoidance of doubt, compounds of the invention may also exist in solution (i.e. in solution in a suitable solvent). For example, compounds of the invention may exist in aqueous solution, in which case compounds of the invention may exist in the form of hydrates thereof.

Compounds of the invention may also exhibit tautomerism. All tautomeric forms and mixtures thereof are included within the scope of the invention (particularly those of sufficient stability to allow for isolation thereof).

Compounds of the invention may also contain one or more asymmetric carbon atoms and may therefore exhibit optical and/or diastereoisomerism (i.e. existing in enantiomeric or diastereomeric forms). Diastereoisomers may be separated using conventional techniques, e.g. chromatography or fractional crystallisation. The various stereoisomers (i.e. enantiomers) may be isolated by separation of a racemic or other mixture of the compounds using conventional, e.g. fractional crystallisation or HPLC, techniques. Alternatively the desired enantiomer or diastereoisomer may be obtained from appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution; for example, with a homochiral acid followed by separation of the diastereomeric derivatives by conventional means such as chromatography), or by reaction with an appropriate chiral reagent or chiral catalyst, all of which methods and processes may be performed under conditions known to the skilled person. Unless otherwise specified, all stereoisomers and mixtures thereof are included within the scope of the invention.

For the avoidance of doubt, the skilled person will understand that where a particular group is depicted herein as being bound to a ring system via a floating bond (i.e. a bond not shown as being bound to a particular atom within the ring), the relevant group may be bound to any suitable atom within the relevant ring system (i.e. the ring within which the floating bond terminates).

Unless otherwise specified, $C_{1-z}$ alkyl groups (where z is the upper limit of the range) defined herein may be straight-chain or, when there is a sufficient number (i.e. a minimum of two or three, as appropriate) of carbon atoms, be branched-chain, and/or cyclic (so forming a $C_{3-z}$ cycloalkyl group). When there is a sufficient number (i.e. a minimum of four) of carbon atoms, such groups may also be part cyclic (so forming a $C_{4-z}$ partial cycloalkyl group). For example, cycloalkyl groups that may be mentioned include cyclopropyl, cyclopentyl and cyclohexyl. Similarly, part cyclic alkyl groups (which may also be referred to as "part cycloalkyl" groups) that may be mentioned include cyclopropylmethyl. When there is a sufficient number of carbon atoms, such groups may also be multicyclic (e.g. bicyclic or tricyclic) and/or spirocyclic. For the avoidance of doubt, particular alkyl groups that may be mentioned include straight chain (i.e. not branched and/or cyclic) alkyl groups.

Unless otherwise specified, $C_{1-z}$ alkoxy groups (i.e. —$OC_{1-z}$ alkyl groups) (where z is the upper limit of the range) defined herein may be straight-chain or, when there is a sufficient number (i.e. a minimum of two or three, as appropriate) of carbon atoms, be branched-chain, and/or cyclic (so forming a —$OC_{3-z}$ cycloalkoxy group). When there is a sufficient number (i.e. a minimum of four) of carbon atoms, such groups may also be part cyclic (so forming a —$OC_{4-z}$ partial cycloalkoxy group). For example, cycloalkyloxy groups that may be mentioned include cyclopropoxy, cyclopentoxy and cyclohexoxy. Similarly, part cyclic alkoxy groups (which may also be referred to as "part cycloalkoxy" groups) that may be mentioned include cyclopropylmethoxy. When there is a sufficient number of carbon atoms, such groups may also be multicyclic (e.g. bicyclic or tricyclic) and/or spirocyclic. For the avoidance of doubt, particular alkyoxy groups that may be mentioned include straight chain (i.e. not branched and/or cyclic) alkoxy groups.

For the avoidance of doubt, references to $C_{1-z}$ alkoxy-$C_{1-z}$ alkyl groups indicate an alkoxyalkyl group (i.e. —$C_{1-z}$ alkyl-O—$C_{1-z}$ alkyl groups) such as methoxymethyl groups. As for alkyl and alkoxy groups, unless otherwise specified such groups may be straight-chain, or when there is a sufficient number of carbon atoms, be branched chain, cyclic and/or part cyclic.

For the avoidance of doubt, alkyl groups as described herein may also act as linker groups (i.e. groups joining two or more parts of the compound as described), in which case such groups may be referred to as "alkylene" groups.

As used herein, the term heterocyclyl may refer to non-aromatic monocyclic and polycyclic (e.g. bicyclic) heterocyclic groups (which groups may, where containing a sufficient number of atoms, also be bridged) in which at least one (e.g. one to four) of the atoms in the ring system is other than carbon (i.e. a heteroatom), and in which the total number of atoms in the ring system is between three and twelve (e.g. between five and ten, such as between three and eight; for example, forming a 5- or 6-membered heterocyclyl group). Further, such heterocyclyl groups may be saturated, forming a heterocycloalkyl, or unsaturated containing one or more carbon-carbon or, where possible, carbon-heteroatom or heteroatom-heteroatom double and/or triple bonds, forming for example a $C_{2-z}$ (e.g. $C_{4-z}$) heterocycloalkenyl (where z is the upper limit of the range) or a $C_{7-z}$ heterocycloalkynyl group.

For the avoidance of doubt, the skilled person will understand that heterocyclyl groups that may form part of compounds of the invention are those that are chemically obtainable, as known to those skilled in the art. Various heterocyclyl groups will be well-known to those skilled in the art, such as 7-azabicyclo-[2.2.1]heptanyl, 6-azabicyclo[3.1.1]heptanyl, 6-azabicyclo[3.2.1]-octanyl, 8-azabicyclo[3.2.1]octanyl, aziridinyl, azetidinyl, 2,3-dihydroisothiazolyl, dihydropyranyl, dihydropyridinyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, isothiazolidinyl, morpholinyl, 7-oxabicyclo[2.2.1]heptanyl, 6-oxabicyclo[3.2.1]-octanyl, oxetanyl, oxiranyl, piperazinyl, piperidinyl, pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuryl, tetrahydropyridinyl (such as 1,2,3,4-tetrahydropyridinyl and 1,2,3,6-tetrahydropyridinyl), thietanyl, thiiranyl, thiolanyl, tetrahydrothiopyranyl, thiomorpholinyl, trithianyl (including 1,3,5-trithianyl), tropanyl and the like.

Substituents on heterocyclyl groups may, where appropriate, be located on any atom in the ring system including a heteroatom. Further, in the case where the substituent is another cyclic compound, then the cyclic compound may be attached through a single atom on the heterocyclyl group, forming a spirocyclic compound. The point of attachment of heterocyclyl groups may be via any suitable atom in the ring system, including (where appropriate) a further heteroatom (such as a nitrogen atom), or an atom on any fused carbocyclic ring that may be present as part of the ring system. Heterocyclyl groups may also be in the N- or S-oxidised forms, as known to those skilled in the art.

At each occurrence when mentioned herein, particular heterocyclyl groups that may be mentioned include 4- to 8-membered heterocyclyl groups (e.g. a 4- to 6-membered heterocyclyl group, such as a 5- or 6-membered heterocyclyl group).

For the avoidance of doubt, references to polycyclic (e.g. bicyclic or tricyclic) groups (for example when employed in the context of heterocyclyl or cycloalkyl groups (e.g. heterocyclyl)) will refer to ring systems wherein at least two scissions would be required to convert such rings into a non-cyclic (i.e. straight or branched) chain, with the minimum number of such scissions corresponding to the number of rings defined (e.g. the term bicyclic may indicate that a minimum of two scissions would be required to convert the rings into a straight chain). For the avoidance of doubt, the term bicyclic (e.g. when employed in the context of alkyl groups) may refer to groups in which the second ring of a two-ring system is formed between two adjacent atoms of the first ring, to groups in which two non-adjacent atoms are linked by an alkyl (which, when linking two moieties, may be referred to as alkylene) group (optionally containing one or more heteroatoms), which later groups may be referred to as bridged, or to groups in which the second ring is attached to a single atom, which latter groups may be referred to as spiro compounds.

Particular heterocyclyl groups that may be mentioned include piperidinyl (e.g. piperidin-1-yl), octahydro-1H-isoindolyl (e.g. octahydro-1H-isoindol-2-yl), azetidinyl (e.g. azetidine-1-yl), oxetanyl (e.g. oxetan-3-yl), morpholinyl (e.g. morpholin-4-yl), piperazinyl (e.g. piperazin-1yl or piperazin-4-yl), azepanyl (e.g. azepan-1-yl), imidazolidinyl (e.g. imidazolidine-2-yl), pyrrolidinyl (e.g. pyrrolidine-1yl), and diazepanyl (e.g. 1,4-diazepan-1-yl).

As may be used herein, the term aryl may refer to $C_{6-14}$ (e.g. $C_{6-10}$) aromatic groups. Such groups may be monocyclic or bicyclic and, when bicyclic, be either wholly or partly aromatic. $C_{6-10}$ aryl groups that may be mentioned include phenyl, naphthyl, 1,2,3,4-tetrahydronaphthyl, indanyl, and the like (e.g. phenyl, naphthyl, and the like). For the avoidance of doubt, the point of attachment of substituents on aryl groups may be via any suitable carbon atom of the ring system.

For the avoidance of doubt, the skilled person will understand that aryl groups that may form part of compounds of the invention are those that are chemically obtainable, as known to those skilled in the art. Particular aryl groups that may be mentioned include phenyl and naphthyl, such as phenyl.

As may be used herein, references to heteroaryl (with may also be referred to as heteroaromatic) groups may refer to 5- to 14- (e.g. 5- to 10-) membered heteroaromatic groups containing one or more heteroatoms (such as one or more heteroatoms selected from oxygen, nitrogen and/or sulfur). Such heteroaryl groups may comprise one, two, or three rings, of which at least one is aromatic. Substituents on heteroaryl/heteroaromatic groups may, where appropriate, be located on any suitable atom in the ring system, including a heteroatom (e.g. on a suitable N atom).

The point of attachment of heteroaryl/heteroaromatic groups may be via any atom in the ring system including (where appropriate) a heteroatom. Bicyclic heteroaryl/heteroaromatic groups may comprise a benzene ring fused to one or more further aromatic or non-aromatic heterocyclic rings, in which instances, the point of attachment of the polycyclic heteroaryl/heteroaromatic group may be via any ring including the benzene ring or the heteroaryl/heteroaromatic or heterocyclyl ring.

For the avoidance of doubt, the skilled person will understand that heteroaryl groups that may form part of compounds of the invention are those that are chemically obtainable, as known to those skilled in the art. Various heteroaryl groups will be well-known to those skilled in the art, such as pyridinyl, pyrrolyl, furanyl, thiophenyl, oxadiazolyl, thiadiazolyl, thiazolyl, oxazolyl, pyrazolyl, triazolyl, tetrazolyl, isoxazolyl, isothiazolyl, imidazolyl, imidazopyrimidinyl, imidazothiazolyl, thienothiophenyl, pyrimidinyl, furopyridinyl, indolyl, azaindolyl, pyrazinyl, pyrazolopyrimidinyl, indazolyl, pyrimidinyl, quinolinyl, isoquinolinyl, quinazolinyl, benzofuranyl, benzothiophenyl, benzoimidazolyl, benzoxazolyl, benzothiazolyl, benzotriazolyl and purinyl.

For the avoidance of doubt, the oxides of heteroaryl/heteroaromatic groups are also embraced within the scope of the invention (e.g. the N-oxide).

As stated above, heteroaryl includes polycyclic (e.g. bicyclic) groups in which one ring is aromatic (and the other may or may not be aromatic). Hence, other heteroaryl groups that may be mentioned include groups such as benzo[1,3]dioxolyl, benzo[1,4]dioxinyl, dihydrobenzo[d]isothiazole, 3,4-dihydrobenz[1,4]oxazinyl, dihydrobenzothiophenyl, indolinyl, 5H,6H,7H-pyrrolo[1,2-b]pyrimidinyl, 1,2,3,4-tetrahydroquinolinyl, thiochromanyl and the like.

For the avoidance of doubt, where a ring is depicted as having circle therein, its presence shall indicate that the relevant ring is aromatic. Alternatively, aromatic groups may be depicted as cyclic groups comprising therein a suitable number of double bonds to allow for aromaticity.

The present invention also embraces isotopically-labelled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Hence, the compounds of the invention also include deuterated compounds, i.e. compounds of the invention in which one or more hydrogen atoms are replaced by the hydrogen isotope deuterium.

For the avoidance of doubt, in cases in which the identity of two or more substituents in a compound of the invention may be the same, the actual identities of the respective substituents are not in any way interdependent. For example, in the situation in which two or more $R^4$ groups are present, those $R^4$ groups may be the same or different. Similarly, where two or more $R^4$ groups are present and each represents $C_{1-2}$ alkyl optionally substituted by one or more fluoro groups, these groups may also be the same or different.

Further for the avoidance of doubt, when it is specified that a substituent is itself optionally substituted by one or more substituents (e.g. $C_{1-3}$ alkyl optionally substituted by one or more fluoro groups), these substituents where possible may be positioned on the same or different atoms. Such optional substituents may be present in any suitable number thereof (e.g. the relevant group may be substituted with one or more such substituents, such as one such substituent).

For the avoidance of doubt, where groups are referred to herein as being optionally substituted it is specifically contemplated that such optional substituents may be not present (i.e. references to such optional substituents may be removed), in which case the optionally substituted group may be referred to as being unsubstituted.

For the avoidance of doubt, the skilled person will appreciate that compounds of the invention that are the subject of this invention include those that are obtainable, i.e. those that may be prepared in a stable form. That is, compounds of the invention include those that are sufficiently robust to survive isolation, e.g. from a reaction mixture, to a useful degree of purity.

Compounds of the invention that may be mentioned include those in which $R^1$ represents methyl; phenyl optionally substituted by one or more (e.g. one) groups selected from halogen, —CN, —C(O)NR$^{a1}$R$^{a2}$, —NR$^{a3}$R$^{a4}$, a 5-membered heteroaryl group (e.g. pyrrolyl or pyrazolyl), $C_{1-4}$ alkyl, $C_{1-4}$ alkoxy, $C_{1-4}$ alkoxy-$C_{1-4}$ alkyl or methylenedioxy, wherein the latter four groups are optionally substituted by one or more (e.g. one) fluoro groups; or a 5-9-membered heteroaryl group (e.g. thiophenyl, pyrazolyl, thiazolyl, pyridinyl, benzofuranyl or indolyl) optionally substituted by one or more (e.g. one) groups selected from halogen, —CN, $C_{1-4}$ alkyl, $C_{1-4}$ alkoxy, $C_{1-4}$ alkoxy-$C_{1-4}$ alkyl or phenyl, which latter four groups are optionally substituted by one or more fluoro groups, wherein R$^{a1}$, R$^{a2}$, R$^{a3}$ and R$^{a4}$ are as defined herein, Compounds of the invention that may be mentioned include those in which $R^1$ represents phenyl optionally substituted by one or more (e.g. one) groups selected from halogen, —CN, —C(O)NR$^{a1}$R$^{a2}$, —NR$^{a3}$R$^{a4}$, a 5-membered heteroaryl group (e.g. pyrrolyl or pyrazolyl), $C_{1-4}$ alkyl, $C_{1-4}$ alkoxy, $C_{1-4}$ alkoxy-$C_{1-4}$ alkyl or methylenedioxy, wherein the latter four groups are optionally substituted by one or more (e.g. one) fluoro groups; or a 5-9-membered heteroaryl group (e.g. thiophenyl, pyrazolyl, thiazolyl, pyridinyl, benzofuranyl or indolyl) optionally substituted by one or more (e.g. one) groups selected from halogen, —CN, $C_{1-4}$ alkyl, $C_{1-4}$ alkoxy, $C_{1-4}$ alkoxy-$C_{1-4}$ alkyl or phenyl, which latter four groups are optionally substituted by one or more fluoro groups, wherein R$^{a1}$, R$^{a2}$, R$^{a3}$ and R$^{a4}$ are as defined herein.

Compounds of the invention that may be mentioned include those in which $R^1$ represents methyl; phenyl optionally substituted by one or more (e.g. one) groups selected from halogen, —CN, —C(O)NR$^{a1}$R$^{a2}$, —NR$^{a3}$R$^{a4}$, $C_{1-4}$ alkyl, $C_{1-4}$ alkoxy, $C_{1-4}$ alkoxy-$C_{1-4}$ alkyl or methylenedioxy, wherein the latter four groups are optionally substituted by one or more (e.g. one) fluoro groups; or a 5-9-membered heteroaryl group (e.g. thiophenyl, pyrazolyl, thiazolyl, pyridinyl, benzofuranyl or indolyl) optionally substituted by one or more (e.g. one) groups selected from halogen, —CN, $C_{1-4}$ alkyl, $C_{1-4}$ alkoxy or phenyl, which latter three groups are optionally substituted by one or more (e.g. one) fluoro groups, wherein R$^{a1}$, R$^{a2}$, R$^{a3}$ and R$^{a4}$ are as defined herein.

Compounds of the invention that may be mentioned include those in which $R^1$ represents phenyl optionally substituted by one or more (e.g. one) groups selected from halogen, —CN, —C(O)NR$^{a1}$R$^{a2}$, —NR$^{a3}$R$^{a4}$, $C_{1-4}$ alkyl, $C_{1-4}$ alkoxy, $C_{1-4}$ alkoxy-$C_{1-4}$ alkyl or methylenedioxy, wherein the latter four groups are optionally substituted by one or more (e.g. one) fluoro groups; or a 5-9-membered heteroaryl group (e.g. thiophenyl, pyrazolyl, thiazolyl, pyridinyl, benzofuranyl or indolyl) optionally substituted by one or more (e.g. one) groups selected from halogen, —CN, $C_{1-4}$ alkyl, $C_{1-4}$ alkoxy or phenyl, which latter three groups are optionally substituted by one or more (e.g. one) fluoro groups, wherein R$^{a1}$, R$^{a2}$, R$^{a3}$ and R$^{a4}$ are as defined herein.

Compounds of the invention that may be mentioned include those in which $R^1$ represents methyl; or, preferably, phenyl optionally substituted by one or more (e.g. one) groups selected from halogen, —CN, —C(O)NR$^{a1}$R$^{a2}$, —NR$^{a3}$R$^{a4}$, $C_{1-4}$ alkyl, $C_{1-4}$ alkoxy, $C_{1-4}$ alkoxy-$C_{1-4}$ alkyl or methylenedioxy, wherein the latter four groups are optionally substituted by one or more (e.g. one) fluoro groups.

Compounds of the invention that may be mentioned include those in which $R^1$ represents methyl; phenyl optionally substituted by one or more (e.g. one) groups selected from halogen, $C_{1-4}$ alkyl, $C_{1-4}$ alkoxy, or methylenedioxy, wherein the latter three groups are optionally substituted by one or more (e.g. one) fluoro groups; or a 5-9-membered heteroaryl group optionally substituted by one or more (e.g. one) groups selected from $C_{1-4}$ alkyl, $C_{1-4}$ alkoxy and phenyl, each of which groups is optionally substituted by one or more fluoro groups.

Compounds of the invention that may be mentioned include those in which $R^1$ represents methyl; phenyl optionally substituted by one or more (e.g. one) groups selected from fluoro, chloro, bromo, $C_{1-2}$ alkyl, $C_{1-2}$ alkoxy, wherein the latter two groups are optionally substituted by one or more (e.g. one) fluoro groups, thiophenyl, thiazolyl, pyrazolyl, pyridinyl, benzofuranyl or indolyl each of which is optionally substituted by one or more groups selected from $C_{1-2}$ alkyl, $C_{1-2}$ alkoxy and phenyl each of which may be optionally substituted by one or more (e.g. one) fluoro groups.

Compounds of the invention that may be mentioned include those in which $R^1$ represents methyl; phenyl optionally substituted by one or more (e.g. one) groups selected from fluoro, chloro, bromo, $C_{1-2}$ alkyl, $C_{1-2}$ alkoxy, wherein the latter two groups are optionally substituted by one or more (e.g. one) fluoro groups; thiophenyl, thiazolyl, pyrazolyl or pyridinyl each of which is optionally substituted by one or more groups selected from $C_{1-2}$ alkyl (e.g. methyl), $C_{1-2}$ alkoxy (e.g. methoxy) and phenyl; benzofuranyl or indolyl each of which is optionally substituted by one or more groups selected from $C_{1-2}$ alkyl (e.g methyl) and $C_{1-2}$ alkoxy (e.g. methoxy).

Compounds of the invention that may be mentioned include those in which $R^1$ represents methyl; phenyl optionally substituted by one or more (e.g. one) groups selected from fluoro, chloro, bromo, $C_{1-2}$ alkyl, $C_{1-2}$ alkoxy, wherein the latter two groups are optionally substituted by one or more F (e.g. unsubstituted); thiophenyl optionally substituted by one or more (e.g. one) methyl groups; pyrazolyl optionally substituted by one or more (e.g. one) methyl or phenyl groups; thiazolyl, pyridinyl, benzofuranyl or indolyl.

Other compounds of the invention that may be mentioned include those in which $R^1$ represents methyl; phenyl optionally substituted by one or more (e.g. one) groups selected from fluoro, chloro, methyl, ethyl, methoxy, ethoxy, —$CF_3$, —$OCF_3$ or methylenedioxy; thiophenyl optionally substituted by one or more (e.g. one) methyl group (e.g. thiophen-2-yl, thiophen-3-yl or 5-methylthiophen-2-yl); pyrazolyl optionally substituted by one or more (e.g. one) methyl or phenyl groups (e.g. pyrazol-3-yl, pyrazol-4-yl, pyrazol-5-yl or, particularly, 1-phenylpyrazol-4-yl); thiazolyl (e.g. thiazol-2-yl, thiazol-4-yl or thiazol-5-yl); pyridinyl (e.g. pyridine-2-yl, pyridine-3-yl or pyridin-4-yl); benzofuranyl (e.g. benzofuran-5-yl; benzofuran-4-yl); or indolyl (e.g. indol-5-yl or indol-4-yl).

Other compounds of the invention that may be mentioned include those in which $R^1$ represents phenyl optionally substituted by one or more (e.g. one) groups selected from fluoro, chloro, methyl, ethyl, methoxy, ethoxy, —$CF_3$, —$OCF_3$ or methylenedioxy; thiophenyl optionally substituted by one or more (e.g. one) methyl group (e.g. thiophen-2-yl, thiophen-3-yl or 5-methylthiophen-2-yl); pyrazolyl optionally substituted by one or more (e.g. one) methyl or phenyl groups (e.g. pyrazol-3-yl, pyrazol-4-yl, pyrazol-5-yl or, particularly, 1-phenylpyrazol-4-yl); thiazolyl (e.g. thiazol-2-yl, thiazol-4-yl or thiazol-5-yl); pyridinyl (e.g. pyridine-2-yl, pyridine-3-yl or pyridin-4-yl); benzofuranyl (e.g. benzofuran-5-yl; benzofuran-4-yl); or indolyl (e.g. indol-5-yl or indol-4-yl).

Compounds of the invention that may be mentioned include those in which $R^1$ represents methyl; or phenyl optionally substituted by one group selected from methyl, methoxy, chloro, fluoro and —$OCF_3$ and methylenedioxy.

Compounds of the invention that may be mentioned include those in which $R^1$ represents phenyl optionally substituted by one group selected from methyl, methoxy, chloro, fluoro and —$OCF_3$ and methylenedioxy.

Further compounds of the invention that may be mentioned include those in which $R^1$ represents methyl, phenyl or tolyl (o-tolyl, p-tolyl or, preferably, m-tolyl).

For the avoidance of doubt, the terms o-tolyl, m-tolyl and p-tolyl may be understood to refer to 2-methylphenyl, 3-methylphenyl and 4-methylphenyl groups, respectively.

Further compounds of the invention that may be mentioned include those in which $R^1$ represents methyl, phenyl, m-tolyl or p-tolyl.

Further compounds of the invention that may be mentioned include those in which $R^1$ represents methyl, phenyl or p-tolyl.

Further compounds that may be mentioned include those in which $R^1$ represents phenyl or tolyl (e.g. m-tolyl).

Further compounds of the invention that may be mentioned include those in which $R^1$ represents methyl or phenyl (particularly phenyl).

Further compounds that may be mentioned include those in which $R^1$ represents m-tolyl.

Compounds of the invention that may be mentioned include those in which $R^2$ represents halogen; hydroxy; cyano; $C_{1-4}$ alkyl or $C_{1-4}$ alkoxy, wherein each alkyl group or alkoxy group is optionally substituted by one or more (e.g. one) fluoro groups.

Compounds of the invention that may be mentioned include those in which $R^2$ represents fluoro, chloro, bromo, hydroxy, $C_{1-3}$ alkyl or $C_{1-3}$ alkoxy, wherein the latter two groups are each optionally substituted by one or more fluoro groups (e.g. methyl, ethyl, propyl, iso-propyl, —$CF_3$, —$CHF_2$, —$CH_2F$, —$CH_2CF_3$, —$CH_2CH_2CF_3$, —OMe, —OEt, —OPr, —OiPr, —$OCF_3$, —$OCHF_2$, —$OCH_2F$, —$OCH_2CF_3$, —$OCH_2CH_2CF_3$).

Compounds of the invention that may be mentioned include those in which $R^2$ represents fluoro, $C_{1-2}$ alkyl or $C_{1-2}$ alkoxy each of which groups are optionally substituted by one or more fluoro groups (e.g. methyl, ethyl, —$CF_3$, —$CHF_2$, —$CH_2F$, —$CH_2CF_3$, —OMe, —OEt, —$OCF_3$, —$OCHF_2$, —$OCH_2F$, —$OCH_2CF_3$).

Compounds of the invention that may be mentioned include those in which $R^2$ represents $C_{1-2}$ alkyl or $C_{1-2}$ alkoxy each of which groups are optionally substituted by one or more fluoro groups (e.g. methyl, ethyl, —$CF_3$, —$CHF_2$, —$CH_2F$, —$CH_2CF_3$, —OMe, —OEt, —$OCF_3$, —$OCHF_2$, —$OCH_2F$, —$OCH_2CF_3$).

Compounds of the invention that may be mentioned include those in which $R^2$ represents fluoro, chloro or $C_{1-2}$alkyl (methyl or, particularly, ethyl).

Compounds of the invention that may be mentioned include those in which $R^2$ represents fluoro or ethyl.

Compounds of the invention that may be mentioned include those in which n represents 0 or 1 (particularly 0).

Compounds of the invention that may be mentioned include those in which n represents 1 and $R^2$ is in the para-position (i.e. 4-position) relative to the point of attachment of the phenyl ring to the X group.

Compounds of the invention that may be mentioned include those in which n represents 1, $R^2$ represents $C_{1-2}$ alkyl (e.g. methyl or, particularly ethyl) or fluoro and $R^2$ is in the para-position (i.e. 4-position) relative to the point of attachment of the phenyl ring to the X group.

Compounds of the invention that may be mentioned include those in which n represents 1, $R^2$ represents $C_{1-2}$ alkyl (e.g. methyl or, particularly ethyl) and $R^2$ is in the para-position (i.e. 4-position) relative to the point of attachment of the phenyl ring to the X group.

Compounds of the invention that may be mentioned include those in which one of $Q^1$, $Q^2$ and $Q^3$ represents —N— and the others represent —$C(R^4)$—. In particular, $Q^3$ may represent —N— and $Q^1$ and $Q^2$ each represent —$C(R^4)$—.

Compounds of the invention that may be mentioned include those in which $Q^1$, $Q^2$ and $Q^3$ each represent —$C(R^4)$—.

Compounds of the invention that may be mentioned include those in which each $R^4$ group independently represents H, chloro, bromo, $C_{1-2}$ alkyl (e.g. methyl) or $C_{1-2}$ alkoxy (e.g methoxy), which latter two groups are optionally substituted by one or more fluoro groups (e.g. methyl, ethyl, —$CF_3$, —$CHF_2$, $CH_2F$, —$CH_2CF_3$ —Omethyl, —Oethyl, —$OCF_3$, —$OCHF_2$, —$OCH_2F$ or —$OCH_2CF_3$ (particularly methyl or —Omethyl)).

Further compounds of the invention that may be mentioned include those in which one $R^4$ group represents chloro, bromo, $C_{1-2}$ alkyl or $C_{1-2}$ alkoxy, which latter two groups are optionally substituted by one or more fluoro groups (e.g. methyl, ethyl, —$CF_3$, —$CHF_2$, $CH_2F$, —$CH_2CF_3$ —Omethyl, —Oethyl, —$OCF_3$, —$OCHF_2$, —$OCH_2F$ or —$OCH_2CF_3$ (particularly methyl or —Omethyl)). and the remaining $R^4$ groups represent H.

Further compounds of the invention include those in which each $R^4$ group represents H (i.e. $Q^1$, $Q^2$ and $Q^3$ independently represent —N— or —CH—, wherein a maximum of two (e.g. one) of $Q^1$ to $Q^3$ may represent —N—).

Further compounds of the invention that may be mentioned include those in which $Q^1$, $Q^2$ and $Q^3$ each represent —CH—.

Compounds of the invention that may be mentioned include those in which A represents a direct bond, —O—, $C_{1-2}$ alkylene, -methyleneO—, —Omethylene-, —N(H)methylene- or -methyleneN(H)—, which latter five groups are optionally substituted by one or more halo or $C_{1-2}$ alkyl groups.

Compounds of the invention that may be mentioned include those in which A represents —O— or $C_{1-2}$ alkylene, -methyleneO—, —Omethylene-, —N(H)methylene- or -methyleneN(H)—, which latter five groups are optionally substituted by one or more chloro, fluoro (e.g. fluoro) or $C_{1-2}$ alkyl groups (e.g. methyl). (e.g. $C_{1-2}$ alkylene optionally substituted by one or more fluoro group).

Further compounds of the invention that may be mentioned include those in which A represents —O— or $C_{1-2}$ alkylene, -methyleneO—, —Omethylene-, which latter three groups are optionally substituted by one or more fluoro of $C_{1-2}$ alkyl groups (e.g. methyl groups).

When A represents an asymmetric group (such as —Omethylene- or -methyleneN(H)—) the it may be understood that the left-hand side of the group is attached to the $Q^1$ to $Q^3$-containing ring and the right-hand side of the group is attached to $R^3$.

Further compounds of the invention that may be mentioned include those in which A represents a direct bond, —O—, $C_{1-2}$ alkylene, —$C_{1-2}$alkyleneO—, —O$C_{1-2}$alkylene-, —N(H)$C_{1-2}$alkylene- or —$C_{1-2}$alkyleneN(H)—, which latter five groups are optionally substituted by one or more halo, $C_{1-2}$ alkyl or groups.

Further compounds of the invention that may be mentioned include those in which A represents a direct bond, —$CH_2$—, —$OCH_2$— or —$OCH_2C(O)$—, which latter three groups are optionally substituted by one or more fluoro groups (e.g unsubstituted).

Further compounds of the invention that may be mentioned include those in which A represents a direct bond, —$CH_2$— or —$OCH_2$— which latter two groups are optionally substituted by one or more fluoro groups (e.g unsubstituted).

Further compounds of the invention that may be mentioned include those in which A represents —O— or $C_{1-2}$alkylene optionally substituted by one ore more fluoro groups.

Further compounds of the invention that may be mentioned include those in which A represents methylene optionally substituted by one or more F (i.e. —$CF_2$—, —CHF— or, particularly —$CH_2$—).

Compounds of the invention that may be mentioned include those in which $R^3$ represents a 5-6-membered heteroaryl group (e.g. pyridinyl, pyridazinyl, pyrimidinyl, pyridazinyl, triazinyl, pyrrolyl, pyrazolyl, imidazolyl, triazolyl, tetrazolyl, oxazolyl, thiazolyl, isoxazolyl, isothiazolyl, oxadiazolyl or thiadiazolyl) optionally substituted by one or more (e.g. one) groups selected from halo, —CN, —$NR^{a9}R^{a10}$, —$C(O)NR^{a11}R^{a12}$, $C_{1-4}$ alkyl, $C_{1-4}$ alkoxy or which latter two groups are optionally substituted by one or more fluoro groups, wherein $R^{a9}$, $R^{a10}$, $R^{a11}$ and $R^{a12}$ are as defined herein.

Compounds of the invention that may be mentioned include those in which $R^3$ represents a 5-membered heteroaryl group (e.g. pyrrolyl (e.g. pyrrol-1-yl), pyazolyl (e.g. pyrazol-1-yl, pyrazol-4-yl), imidazolyl (e.g. imidazol-1-yl, imidazol-2-yl or imidazol-5-yl), triazolyl (e.g. triazol-1-yl) or tetrazolyl (e.g. tetrazol-1-yl)) optionally substituted by one or more (e.g. one) groups selected from halo, —CN, —$NR^{a9}R^{a10}$, —$C(O)NR^{a11}R^{a12}$, $C_{1-4}$ alkyl, $C_{1-4}$ alkoxy or which latter two groups are optionally substituted by one or more fluoro groups, wherein $R^{a9}$, $R^{a10}$, $R^{a11}$ and $R^{a12}$ are as defined herein.

Compounds of the invention that may be mentioned include those in which $R^3$ represents a 5-membered heteroaryl group (e.g. pyrrolyl (e.g. pyrrol-1-yl), pyazolyl (e.g. pyrazol-1-yl, pyrazol-4-yl), imidazolyl (e.g. imidazol-1-yl, imidazol-2-yl, imidazol-5-yl), triazolyl (e.g. triazol-1-yl)) optionally substituted by one or more (e.g. one) groups selected from halo, —CN, —$NR^{a9}R^{a10}$, —$C(O)NR^{a11}R^{a12}$, $C_{1-4}$ alkyl, $C_{1-4}$ alkoxy or which latter two groups are optionally substituted by one or more fluoro groups, wherein $R^{a9}$, $R^{a10}$, $R^{a11}$ and $R^{a12}$ are as defined herein.

Compounds of the invention that may be mentioned include those in which $R^3$ represents a 5-6-membered heteroaryl group, optionally substituted by one or more (e.g. one) groups selected from halo, $C_{1-4}$ alkyl, $C_{1-4}$ alkoxy or —$N(C_{1-4}$ alkyl$)(C_{1-4}$ alkyl$)$, which latter three groups are optionally substituted by one or more fluoro groups.

Compounds of the invention that may be mentioned include those in which $R^3$ represents a 5-6 membered heteroaryl group comprising at least one nitrogen atom (for example one to three nitrogen atoms, such as one or two nitrogen atoms).

Compounds of the invention that may be mentioned include those in which $R^3$ represents a 5-6-membered heteroaryl group selected from pyridinyl, pyridazinyl, pyrimidinyl, pyridazinyl, triazinyl, pyrrolyl, pyrazolyl, imidazolyl, triazolyl (e.g. triazol-1-yl), tetrazolyl, oxazolyl, thiazolyl, isoxazolyl, isothiazolyl, oxadiazolyl and thiadiazolyl, wherein each 5-6-membered heteroaryl group is optionally substituted by one or more (e.g. one) fluoro, chloro, bromo, $C_{1-2}$ alkyl groups (e.g. methyl), $C_{1-2}$ alkoxy (e.g. methoxy) or —$N(C_{1-2}$ alkyl$)(C_{1-2}$ alkyl$)$ (e.g. —$NMe_2$) groups, which latter three groups are optionally substituted by one or more fluoro groups.

Compounds of the invention that may be mentioned include those in which $R^3$ represents a 5-6-membered heteroaryl group selected from pyridinyl, pyridazinyl, pyrimidinyl, pyridazinyl, triazinyl, pyrrolyl, pyrazolyl, imidazolyl, triazolyl (e.g. triazol-1-yl), tetrazolyl, oxazolyl, thiazolyl, isoxazolyl, isothiazolyl, oxadiazolyl and thiadiazolyl, wherein each 5-6-membered heteroaryl group is optionally substituted by one or more (e.g. one) fluoro, chloro, bromo, $C_{1-2}$ alkyl groups (e.g. methyl), $C_{1-2}$ alkoxy (e.g. methoxy) or —$N(C_{1-2}$ alkyl$)(C_{1-2}$ alkyl$)$ (e.g. —$NMe_2$) groups.

Compounds of the invention that may be mentioned include those in which $R^3$ represents a 5-6-membered heteroaryl group selected from pyridinyl (e.g., pyridin-2-yl, pyridin-3-yl or pyridin-4-yl), pyridazinyl (e.g. pyridazin-3-yl, pyridazin-4-yl, pyridazin-5-yl or pyridazine-6-yl), pyrimidinyl (e.g. pyrimidin-2-yl, pyrimidin-4-yl or pyrimidin-5-yl), pyridazinyl (e.g. pyridazin-2-yl or pyridazin-3-yl), triazinyl (.e.g. triazin-2-yl), pyrrolyl (e.g. pyrrol-1-yl), pyazolyl (e.g. pyrazol-1-yl, pyrazol-4-yl), imidazolyl (e.g. imidazol-1-yl, imidazol-2-yl, imidazol-5-yl), triazolyl (e.g. triazol-1-yl), tetrazolyl (e.g. tetrazol-1-yl), wherein each 5-6-membered heteroaryl group is optionally substituted by one or more (e.g. one) fluoro, chloro, bromo, $C_{1-2}$ alkyl groups (e.g. methyl), $C_{1-2}$ alkoxy (e.g. methoxy) or —$N(C_{1-2}$ alkyl$)(C_{1-2}$ alkyl$)$ (e.g. —$NMe_2$) groups, which latter three groups are optionally substituted by one or more fluoro groups.

Compounds of the invention that may be mentioned include those in which $R^3$ represents a 5-6-membered heteroaryl group selected from pyridinyl (e.g., pyridin-2-yl, pyridin-3-yl or pyridin-4-yl), pyridazinyl (e.g. pyridazin-3-yl, pyridazin-4-yl, pyridazin-5-yl or pyridazine-6-yl), pyrimidinyl (e.g. pyrimidin-2-yl, pyrimidin-4-yl or pyrimidin-5-yl), pyridazinyl (e.g. pyridazin-2-yl or pyridazin-3-yl), triazinyl (.e.g. triazin-2-yl) pyrrolyl (e.g. pyrrol-1-yl), pyazolyl (e.g. pyrazol-1-yl), imidazolyl (e.g. imidazol-1-yl), triazolyl (e.g. triazol-1-yl), tetrazolyl (e.g. tetrazol-1-yl), wherein each 5-6-membered heteroaryl group is optionally substituted by one or more (e.g. one) fluoro, chloro, bromo, $C_{1-2}$ alkyl groups (e.g. methyl), $C_{1-2}$ alkoxy (e.g. methoxy) or —N($C_{1-2}$ alkyl)($C_{1-2}$ alkyl) (e.g. —NMe$_2$) groups.

Compounds of the invention that may be mentioned include those in which $R^3$ represents a 5-membered heteroaryl group selected from pyrrolyl (e.g. pyrrol-1-yl), pyazolyl (e.g. pyrazol-1-yl, pyrazol-4-yl), imidazolyl (e.g. imidazol-1-yl, imidazol-2-yl or imidazol-5-yl), triazolyl (e.g. triazol-1-yl), tetrazolyl (e.g. tetrazol-1-yl), wherein each 5-membered heteroaryl group is optionally substituted by one or more (e.g. one) fluoro, chloro, bromo or $C_{1-2}$ alkyl groups (e.g. methyl), which $C_{1-2}$ alkyl groups are optionally substituted by one or more fluoro groups.

Compounds of the invention that may be mentioned include those in which $R^3$ represents a 5-membered heteroaryl group selected from pyrrolyl (e.g. pyrrol-1-yl), pyazolyl (e.g. pyrazol-1-yl), imidazolyl (e.g. imidazol-1-yl), triazolyl (e.g. triazol-1-yl), tetrazolyl (e.g. tetrazol-1-yl), wherein each 5-membered heteroaryl group is optionally substituted by one or more (e.g. one) fluoro, chloro, bromo or $C_{1-2}$ alkyl groups (e.g. methyl).

Further compounds of the invention that may be mentioned include those in which $R^3$ represents a 5-membered heteroaryl group selected from pyrrolyl (e.g. pyrrol-1-yl), pyazolyl (e.g. pyrazol-1-yl, pyrazol-4-yl), imidazolyl (e.g. imidazol-1-yl, imidazole-2-yl, imidazole-5-yl), triazolyl (e.g. triazol-1-yl), tetrazolyl (e.g. tetrazol-1-yl), wherein each 5-membered heteroaryl group is optionally substituted by one or more (e.g. one) fluoro, methyl or ethyl group, wherein each methyl or ethyl group is optionally substituted by one or more F (e.g. —CF$_3$, —CF$_2$H, —CFH$_2$ or —CH$_2$CF$_3$).

Further compounds of the invention that may be mentioned include those in which $R^3$ represents a 5-membered heteroaryl group selected from pyrrolyl (e.g. pyrrol-1-yl), pyazolyl (e.g. pyrazol-1-yl, pyrazol-4-yl), imidazolyl (e.g. imidazol-1-yl, imidazol-2-yl, imidazol-5-yl), triazolyl (e.g. triazol-1-yl), wherein each 5-membered heteroaryl group is optionally substituted by one or more (e.g. one) fluoro, methyl or ethyl group, wherein each methyl or ethyl group is optionally substituted by one or more F (e.g. —CF$_3$, —CF$_2$H, —CFH$_2$ or —CH$_2$CF$_3$).

Further compounds of the invention that may be mentioned include those in which $R^3$ represents a 5-membered heteroaryl group selected from pyrrolyl (e.g. pyrrol-1-yl), pyazolyl (e.g. pyrazol-1-yl), imidazolyl (e.g. imidazol-1-yl), triazolyl (e.g. triazol-1-yl), tetrazolyl (e.g. tetrazol-1-yl).

For the avoidance of doubt, the terms pyrrol-1-yl, pyrazol-1-yl, pyrazol-4-yl, imidazol-1-yl, imidazol-2-yl, imidazol-5-yl and tetrazol-1-yl respectively refer to the following substituents

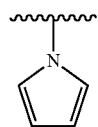 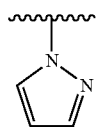 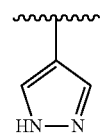 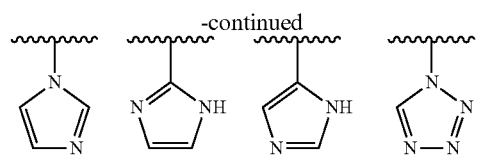

wherein ∿∿ indicates the point of attachment to the rest of the molecule.

The term triazolyl may refer to a 1,2,4-triazole substituent or a 1,2,3-triazole substituent (e.g. a 1,2,4-triazole substituent). Similarly, the term triazol-1-yl may refer to a 1,2,4-triazol-1-yl or a 1,2,3-triazol-1-yl substituent as shown below

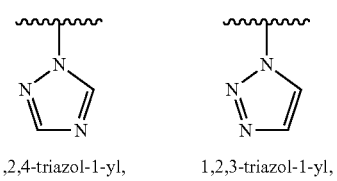

1,2,4-triazol-1-yl,    1,2,3-triazol-1-yl, wherein ∿∿ indicates the point of attachment to the rest of the molecule.

Further compounds of the invention that may be mentioned include those in which $R^3$ represents pyrrol-1-yl, pyrazol-1-yl, pyrazol-4-yl, imidazol-1-yl, imidazol-2-yl, imidazol-5-yl or 1,2,4-triazol-1-yl, wherein each 5-membered heteroaryl group is optionally substituted by one or more fluoro, methyl, or ethyl groups, which latter two groups are optionally substituted by one or more fluoro groups (e.g. —CF$_3$, —CF$_2$H, —CFH$_2$ or —CH$_2$CF$_3$).

Further compounds of the invention that may be mentioned include those in which $R^3$ represents pyrrol-1-yl, pyrazol-1-yl, pyrazol-4-yl, 4-ethylpyrazol-1-yl, 4-fluoropyrazol-1-yl, 1-ethylpyrazol-4-yl, imidazol-1-yl, imidazol-2-yl, imidazol-5-yl, 4-methylimidazol-1-yl, 5-methylimidazol-4-yl, 4-fluoroimidazol-1-yl, 4-difluoromethylimidazol-1-yl or 1,2,4-triazol-1-yl.

Further compounds of the invention that may be mentioned include those in which $R^3$ represents pyrazol-1-yl or imidazol-1-yl, each of which is optionally substituted by one (e.g. one) or more fluoro groups (e.g. 4-fluoropyrazol-1-yl, 4-fluoroimidazol-1-yl)

Further compounds of the invention that may be mentioned include those in which $R^3$ represents pyrazol-1-yl, imidazol-1-yl or 1,2,4-triazol-1-yl.

Further compounds of the invention that may be mentioned include those in which $R^3$ represents pyrazolyl (e.g. pyrazol-4-yl or, preferably, pyrazol-1-yl), which pyrazolyl groups is optionally substituted by one or more (e.g. one) fluoro groups.

Compounds of the invention that may be mentioned include those in which X represents —CH$_2$—, —NH—, —O—, —S— or a direct bond.

Compounds of the invention that may be mentioned include those in which X represents —CH$_2$—, —NH—, —O— or a direct bond.

Compounds of the invention that may be mentioned include those in which X represents —O—, —S— or a direct bond.

Further compounds of the invention that may be mentioned include those in which X represents —O— or a direct bond (particularly —O—).

Compounds of the invention that may be mentioned include those in which when X represents —C(R$^5$)R$^6$—, R$^5$ and R$^6$ each independently represent H or methyl (i.e. X represents —C(CH$_3$)$_2$—, —C(CH$_3$)H— or, particularly, —CH$_2$—).

Compounds of the invention that may be mentioned include those in which when X represents —N(R$^7$)—, R$^7$ represents methyl or H (i.e. X represents —N(CH$_3$)— or particularly —NH—).

Compounds of the invention that may be mentioned include those in which R$^{a1}$, R$^{a2}$, R$^{a3}$, R$^{a4}$, R$^{a5}$, R$^{a6}$, R$^{a7}$, R$^{a8}$, R$^{a9}$, R$^{a10}$, R$^{a11}$ and R$^{a12}$ each independently represent H or C$_{1-2}$ alkyl, which C$_{1-2}$ alkyl groups are optionally substituted by one or more fluoro groups; or R$^{a1}$ and R$^{a2}$, R$^{a3}$ and R$^{a4}$, R$^{a5}$ and R$^{a6}$, R$^{a7}$ and R$^{a8}$, R$^{a9}$ and R$^{a10}$ and R$^{a11}$ and R$^{a12}$ may independently be joined together to form, together with the atom to which they are attached, a 4- to 7-membered heterocyclyl ring, which heterocyclyl ring optionally contains one further heteroatom selected from N, O and S (e.g. N or O).

Further compounds of the invention that may be mentioned include those in which R$^{a1}$, R$^{a2}$, R$^{a3}$, R$^{a4}$, R$^{a5}$, R$^{a6}$, R$^{a7}$, R$^{a8}$, R$^{a9}$, R$^{a10}$, R$^{a11}$ and R$^{a12}$ each independently represent H or C$_{1-2}$ alkyl, which C$_{1-2}$ alkyl groups are optionally substituted by one or more fluoro groups.

Particular compounds of the invention that may be mentioned include those in which:

R$^1$ represents methyl; phenyl optionally substituted by one or more (e.g. one) groups selected from fluoro, chloro, bromo, C$_{1-2}$ alkyl, C$_{1-2}$ alkoxy, wherein the latter two groups are optionally substituted by one or more (e.g. one) fluoro groups; thiophenyl, thiazolyl, pyrazolyl, pyridinyl, benzofuranyl or indolyl each of which is optionally substituted by one or more groups selected from C$_{1-2}$ alkyl, C$_{1-2}$ alkoxy and phenyl each of which may be optionally substituted by one or more (e.g. one) fluoro groups;

R$^2$ represents fluoro, chloro, bromo, hydroxy, C$_{1-3}$ alkyl or C$_{1-3}$ alkoxy, wherein the latter two groups are each optionally substituted by one or more fluoro groups (e.g. methyl, ethyl, propyl, iso-propyl, —CF$_3$, —CHF$_2$, —CH$_2$F, —CH$_2$CF$_3$, —CH$_2$CH$_2$CF$_3$, —OMe, —OEt, —OPr, —OiPr, —OCF$_3$, —OCHF$_2$, —OCH$_2$F, —OCH$_2$CF$_3$, —OCH$_2$CH$_2$CF$_3$);

n represents 0 or 1 (particularly 0), and when n represents 1R$^2$ is preferably located in the para-position (i.e. 4-position) relative to the point of attachment of the phenyl ring to the X group;

Q$^1$, Q$^2$ and Q$^3$ each represent —C(R$^4$)—;

Each R$^4$ group independently represents H, chloro, bromo, C$_{1-2}$ alkyl (e.g. methyl) or C$_{1-2}$ alkoxy (e.g methoxy), which latter two groups are optionally substituted by one or more fluoro groups (e.g. methyl, ethyl, —CF$_3$, —CHF$_2$, CH$_2$F, —CH$_2$CF$_3$ —Omethyl, —Oethyl, —OCF$_3$, —OCHF$_2$, —OCH$_2$F or —OCH$_2$CF$_3$ (particularly methyl or —Omethyl));

A represents —O— or C$_{1-2}$ alkylene, -methyleneO—, —Omethylene-, which latter three groups are optionally substituted by one or more fluoro of C$_{1-2}$ alkyl groups (e.g. methyl groups);

R$^3$ represents a 5-membered heteroaryl group selected from pyrrolyl (e.g. pyrrol-1-yl), pyazolyl (e.g. pyrazol-1-yl), imidazolyl (e.g. imidazol-1-yl), triazolyl (e.g. triazol-1-yl), tetrazolyl (e.g. tetrazol-1-yl), wherein each 5-membered heteroaryl group is optionally substituted by one or more (e.g. one) fluoro, chloro, bromo or C$_{1-2}$ alkyl groups (e.g. methyl);

X represents —CH$_2$—, —NH—, —O—, —S— or a direct bond.

Further compounds of the invention that may be mentioned include those in which:

R$^1$ represents methyl; phenyl optionally substituted by one or more (e.g. one) groups selected from fluoro, chloro, methyl, ethyl, methoxy, ethoxy, —CF$_3$, —OCF$_3$ or methylenedioxy; thiophenyl optionally substituted by one or more (e.g. one) methyl group (e.g. thiophen-2-yl, thiophen-3-yl or 5-methylthiophen-2-yl); pyrazolyl optionally substituted by one or more (e.g. one) methyl or phenyl groups (e.g. pyrazol-3-yl, pyrazol-4-yl, pyrazol-5-yl or, particularly, 1-phenylpyrazol-4-yl); thiazolyl (e.g. thiazol-2-yl, thiazol-4-yl or thiazol-5-yl); pyridinyl (e.g. pyridine-2-yl, pyridine-3-yl or pyridin-4-yl); benzofuranyl (e.g. benzofuran-5-yl; benzofuran-4-yl); or indolyl (e.g. indol-5-yl or indol-4-yl);

R$^2$ represents C$_{1-2}$ alkyl or C$_{1-2}$ alkoxy each of which groups are optionally substituted by one or more fluoro groups (e.g. methyl, ethyl, —CF$_3$, —CHF$_2$, —CH$_2$F, —CH$_2$CF$_3$, —OMe, —OEt, —OCF$_3$, —OCHF$_2$, —OCH$_2$F, —OCH$_2$CF$_3$);

n represents 0 or 1 (particularly 0), and when n represents 1R$^2$ is preferably located in the para-position (i.e. 4-position) relative to the point of attachment of the phenyl ring to the X group;

one of Q$^1$, Q$^2$ and Q$^3$ represents —N— and the others represent —C(R$^4$)—; or Q$^1$, Q$^2$ and Q$^3$ each represent —C(R$^4$)—;

one R$^4$ group represents chloro, bromo, C$_{1-2}$ alkyl or C$_{1-2}$ alkoxy, which latter two groups are optionally substituted by one or more fluoro groups (e.g. methyl, ethyl, —CF$_3$, —CHF$_2$, CH$_2$F, —CH$_2$CF$_3$ —Omethyl, —Oethyl, —OCF$_3$, —OCHF$_2$, —OCH$_2$F or —OCH$_2$CF$_3$ (particularly methyl or —Omethyl)). and the remaining R$^4$ groups represent H; or all R$^4$ groups represent H;

A represents a direct bond, —CH$_2$—, —OCH$_2$— or —OCH$_2$C(O)—, which latter three groups are optionally substituted by one or more fluoro groups (e.g unsubstituted);

R$^3$ represents a 5-membered heteroaryl group selected from pyrrolyl (e.g. pyrrol-1-yl), pyazolyl (e.g. pyrazol-1-yl, pyrazol-4-yl), imidazolyl (e.g. imidazol-1-yl, imidazol-2-yl, imidazol-5-yl), triazolyl (e.g. triazol-1-yl), wherein each 5-membered heteroaryl group is optionally substituted by one or more (e.g. one) fluoro, methyl or ethyl group, wherein each methyl or ethyl group is optionally substituted by one or more F (e.g. —CF$_3$, —CF$_2$H, —CFH$_2$ or —CH$_2$CF$_3$);

X represents —O—, —S— or a direct bond.

Further compounds of the invention that may be mentioned include those in which;

R$^1$ represents methyl; or, preferably, phenyl optionally substituted by one group selected from methyl, methoxy, chloro, fluoro and —OCF$_3$ and methylenedioxy;

R$^2$ represents fluoro, chloro or C$_{1-2}$alkyl (methyl or, particularly, ethyl);

n represents 0 or 1 (particularly 0), and when n represents 1R$^2$ is preferably located in the para-position (i.e. 4-position) relative to the point of attachment of the phenyl ring to the X group;

Q$^1$, Q$^2$ and Q$^3$ each represent —C(R$^4$)—;

one R$^4$ group represents chloro, bromo, C$_{1-2}$ alkyl or C$_{1-2}$ alkoxy, which latter two groups are optionally substituted by one or more fluoro groups (e.g. methyl, ethyl, —CF$_3$, —CHF$_2$, CH$_2$F, —CH$_2$CF$_3$ —Omethyl, —Oethyl, —OCF$_3$, —OCHF$_2$, —OCH$_2$F or —OCH$_2$CF$_3$ (particularly methyl or —Omethyl)). and the remaining R$^4$ groups represent H; or, preferably, all R$^4$ groups represent H;

A represents a direct bond, —CH₂— or —OCH₂— which latter two groups are optionally substituted by one or more fluoro groups (e.g unsubstituted);

R³ represents a 5-membered heteroaryl group selected from pyrrolyl (e.g. pyrrol-1-yl), pyazolyl (e.g. pyrazol-1-yl, pyrazol-4-yl), imidazolyl (e.g. imidazol-1-yl, imidazol-2-yl, imidazol-5-yl), triazolyl (e.g. triazol-1-yl) (preferably pyazolyl (e.g. pyrazol-1-yl, pyrazol-4-yl) or imidazolyl (e.g. imidazol-1-yl, imidazol-2-yl, imidazol-5-yl), more preferably pyrazolyl (e.g. pyrazol-1-yl)), wherein each 5-membered heteroaryl group is optionally substituted by one or more (e.g. one) fluoro, methyl or ethyl group, wherein each methyl or ethyl group is optionally substituted by one or more F (e.g. methyl, ethyl, —CF₃, —CF₂H, —CFH₂ or —CH₂CF₃);

X represents —O— or a direct bond (particularly —O—).

Medical Uses

As indicated herein, the compounds of the invention, and therefore compositions and kits comprising the same, are useful as pharmaceuticals.

Although compounds of the invention may possess pharmacological activity as such, certain pharmaceutically-acceptable (e.g. "protected") derivatives of compounds of the invention may exist or be prepared which may not possess such activity, but may be administered parenterally or orally and thereafter be metabolised in the body to form compounds of the invention. Such compounds (which may possess some pharmacological activity, provided that such activity is appreciably lower than that of the active compounds to which they are metabolised) may therefore be described as "prodrugs" of compounds of the invention.

As used herein, references to prodrugs will include compounds that form a compound of the invention, in an experimentally-detectable amount, within a predetermined time, following enteral (e.g. oral) or parenteral administration. All prodrugs of the compounds of the invention are included within the scope of the invention.

Furthermore, certain compounds of the invention may possess no or minimal pharmacological activity as such, but may be administered parenterally or orally, and thereafter be metabolised in the body to form compounds of the invention that possess pharmacological activity as such. Such compounds (which also includes compounds that may possess some pharmacological activity, but that activity is appreciably lower than that of the active compounds of the invention to which they are metabolised), may also be described as "prodrugs".

For the avoidance of doubt, compounds of the invention are therefore useful because they possess pharmacological activity, and/or are metabolised in the body following oral or parenteral administration to form compounds that possess pharmacological activity.

As described herein, compounds of the invention may be particularly useful in the treatment of diseases characterised by impaired signalling of neurotrophins and/or other trophic factors. Due to their mode of action, compounds of the invention may have particular utility in the treatment of such diseases in patients with the Val66Met mutation in the BDNF gene.

The compounds of the invention may also have particular utility in the treatment of diseases characterised by impaired signalling of neurotrophins and/or other trophic factors in patients having other genetic variations, including deletions, that directly or indirectly affect the BDNF gene. For example, the compounds of the invention may have particular utility in treating diseases in patients having the r512291063 minor C allele, which is known to be associated with lower BDNF expression, and/or in patients having the deletions associated with WAGR syndrome, such as the deletions in chromosome 11.

Accordingly, in particular embodiments of the invention, there is provided the compounds of the invention for use in the treatment of the diseases described herein in a patient having the Val66Met mutation in the BDNF gene, and/or in a patient having the r512291063 minor C allele, and/or in a patient having the genetic deletions associated with WAGR syndrome.

The skilled person will understand that trophic factors refer to a class of molecules that promote the growth and maintenance of cellular tissues. Neurotrophins may be understood to refer to a class of molecules associated with promoting the growth and survival of neurons, which are also referred to as neurotrophic factors. Examples of neurotrophins include NGF, BDNF, NT3 and NT4/5. Other trophic factors include insulin-like growth factor (IGF-1), fibroblast growth factors (FGFs), hepatocyte growth factor (HGF) and glial cell line-derived neurotrophic factors such as glial cell-derived neurotrophic factor (GDNF), Neurturin (NRTN), artemin (ARTN) and persephin (PSPN).

As used herein, the phrase diseases characterised by impaired signalling of neurotrophins and other trophic factors may be understood to indicate diseases and disorders that involve reduced signalling of trophic factors, such as those listed above. Such disorders may be treated through the positive modulation of neurotrophin receptors, such as TrKA, TrKB and TrkC and/or their signalling, and receptor tyrosine kinases such as FGFR1 and IGF1R and/or their signalling and/or the positive modulation of other trophic factor receptors.

The Val66Met mutation in the BDNF gene refers to a common single-nucleotide polymorphism in the brain-derived neurotrophic factor (BDNF) gene, resulting in a methionine (Met) substitution for valine (Val) at codon 66 (Val66Met).

The skilled person will understand that references to the treatment of a particular condition (or, similarly, to treating that condition) will take their normal meanings in the field of medicine. In particular, the terms may refer to achieving a reduction in the severity and/or frequency of occurrence of one or more clinical symptom associated with the condition, as adjudged by a physician attending a patient having or being susceptible to such symptoms. For example, in the case of Alzheimer's disease, the term may refer to achieving an improvement in cognition in the patient being treated.

As used herein, the term prevention (and, similarly, preventing) will include references to the prophylaxis of the disease or disorder (and vice versa). As such, references to prevention may also be references to prophylaxis, and vice versa. In particular, such terms may refer to achieving a reduction (for example, at least a 10% reduction, such as at least a 20%, 30% or 40% reduction, e.g. at least a 50% reduction) in the likelihood of the patient (or healthy subject) developing the condition (which may be understood as meaning that the condition of the patient changes such that patient is diagnosed by a physician as having, e.g. requiring treatment for, the relevant disease or disorder).

As used herein, references to a patient (or to patients) will refer to a living subject being treated, including mammalian (e.g. human) patients.

For the avoidance of doubt, the skilled person will understand that such treatment or prevention will be performed in a patient (or subject) in need thereof. The need of a patient (or subject) for such treatment or prevention may be assessed by those skilled the art using routine techniques.

As used herein, the terms disease and disorder (and, similarly, the terms condition, illness, medical problem, and the like) may be used interchangeably.

Compounds of the invention are modulators of neurotrophin receptors, such as TrkA, TrkB, TrkC and/or their signalling and receptor tyrosine kinases, such as FGFR1 and IGF1R and/or their signalling. The compounds are believed to have an improved potency for the modulation of neurotrophin receptors, such as TrkA, TrkB, TrkC and/or their signalling and receptor tyrosine kinases, such as FGFR1 and IGF1R and/or their signalling. It is believed that the compounds of the invention would have a reduced potential for side effects associated with conventional agonists for TrkA and TrkB.

Another indication includes setting in which there is a goal for enhancing plasticity of the nervous system, such as during rehabilitation or acquisition of a new learned physical or intellectual skill. Moreover, it also includes facilitation of neuronal or non-neuronal or stem cell survival or promoting neural function by treating a neural or non-neuronal or stem cell with a compound of the invention having the ability to have a positive modulatory effect, either directly or indirectly, on the signalling mediated by the TrkA, TrkB and TrkC receptors, optionally in combination with a modulatory effect, either directly or indirectly, on on the signalling mediated by receptor tyrosine kinases such as IGF1R and/or FGFR1 receptor.

The invention relates to the compounds of the invention and pharmaceutically-acceptable salts thereof, as defined above, for use in medicine (e.g. human medicine). Without being bound to theory regarding the mode of action of the compounds defined above, it is believed that the compounds can be used for treatment and/or prevention of the diseases mentioned herein.

In particular embodiments, the diseases that may be treated by compounds of the invention include Alzheimer's disease, depression, Parkinson's disease, other Parkinsonian disorders and/or other tauopathies, Lewy body dementia, multiple sclerosis, Huntington's disease, mild cognitive impairment, brain injuries (including traumatic brain injuries), stroke, other dementia disorders, motorneurone diseases, Pick disease, spinal chord injury, hypoxic ischemia injury, cognitive dysfunction, coronary artery disease, obesity, metabolic syndrome, diabetes, Charcot-Marie-Tooth disease, diabetic neuropathy (including complications thereof such as osteoporosis, painful connective tissue disorders and tendon ruptures), tissue regeneration, motor function, nerve injury, hearing loss, blindness, posterior eye diseases, dry eye disease, neurotrophic keratitis, glaucoma, high intraocular pressure (IOP), retinitis pigmentosa, post-traumatic stress disorders, WAGR syndrome, diseases of the olfactory tract, olfactory decline, olfactory dysfunction, anxiety, fragile X syndrome, congenital central hypoventilation syndrome, obsessive-compulsive disorder, generalized anxiety disorder, eating disorders, bipolar disorder, chronic fatigue syndrome, neuromyelitis optica, Rett syndrome, Friedrich's ataxia, obstructive sleep apnea-hypopnea syndrome and constipation (including, particularly, constipation in Parkinson's disease, slow-transit constipation and opioid-induced constipation).

In particular embodiments, the diseases that may be treated by compounds of the invention include Alzheimer's disease, depression, Parkinson's disease, other Parkinsonian disorders and/or other tauopathies, Lewy body dementia, multiple sclerosis, Huntington's disease, mild cognitive impairment, brain injuries (including traumatic brain injuries), stroke, other dementia disorders, motorneurone diseases, Pick disease, spinal chord injury, hypoxic ischemia injury, cognitive dysfunction, coronary artery disease, obesity, metabolic syndrome, diabetes, Charcot-Marie-Tooth disease, diabetic neuropathy (including complications thereof such as osteoporosis (diabetes-induced osteoporosis), painful connective tissue disorders and tendon ruptures), tissue regeneration, motor function, nerve injury, hearing loss (including genetic or acquired hearing loss), blindness, posterior eye diseases, anterior eye diseases, dry eye disease, neurotrophic keratitis, glaucoma, high intraocular pressure (IOP), retinitis pigmentosa, post-traumatic stress disorders, WAGR syndrome, Prader-Willi syndrome, diseases of the olfactory tract, olfactory decline, olfactory dysfunction, anxiety, fragile X syndrome, congenital central hypoventilation syndrome, obsessive-compulsive disorder, generalized anxiety disorder, eating disorders, bipolar disorder, chronic fatigue syndrome, neuromyelitis optica, Rett syndrome, Friedrich's ataxia, obstructive sleep apnea-hypopnea syndrome and constipation (including, particularly, constipation in Parkinson's disease, slow-transit constipation and opioid-induced constipation).

In particular embodiments, the diseases that may be treated by compounds of the invention include Alzheimer's disease, depression, Parkinson's disease, other Parkinsonian disorders and/or other tauopathies, Lewy body dementia, multiple sclerosis, Huntington's disease, mild cognitive impairment, brain injuries (including traumatic brain injuries), stroke, other dementia disorders, motorneurone diseases, Pick disease, spinal chord injury, hypoxic ischemia injury, cognitive dysfunction, coronary artery disease, obesity, metabolic syndrome, diabetes, Charcot-Marie-Tooth disease, diabetic neuropathy (including complications thereof such as osteoporosis, painful connective tissue disorders and tendon ruptures), tissue regeneration, motor function, nerve injury, hearing loss, blindness, posterior eye diseases, dry eye disease, neurotrophic keratitis, glaucoma, high intraocular pressure (IOP), retinitis pigmentosa, post-traumatic stress disorders, WAGR syndrome, diseases of the olfactory tract, olfactory decline, olfactory dysfunction, anxiety, fragile X syndrome, congenital central hypoventilation syndrome, obsessive-compulsive disorder, generalized anxiety disorder, eating disorders, bipolar disorder, chronic fatigue syndrome, neuromyelitis optica, Rett syndrome, Friedrich's ataxia and obstructive sleep apnea-hypopnea syndrome.

As used herein, the phrase "other Parkinsonian disorders" may be understood to refer to disorders that have symptoms similar to Parkinson's disease, such as bradykinesia, tremors and postural instability. Examples of such disorders include progressive supranuclear palsy (PSP), multiple system atrophy (MSA), and corticobasal degeneration (CBD).

The phrase "other tauopathies" may be understood to refer to neurodegenerative diseases other than Alzheimer's disease that are associated with the pathological misfolding of tau protein in the brain. Examples of such disorders include primary age-related tauopathy, progressive supranuclear palsy, Pick's disease, corticobasal degeneration and post-encephalitic parkinsonism. The skilled person will understand that certain disorders such as progressive supranuclear palsy may be described as both a Parkinsonian disorder and a tauopathy.

The phrase "other dementia disorders" may be understood to include vascular dementia, mixed vascular dementia, incident dementia, post-operative dementia, presenile dementia, dementia associated with Parkinson's disease and dementia due to HIV infection. Progressive supranuclear palsy and corticobasal degeneration may also be classed as dementia disorders.

Motor neurone dieseases include amyotrophic lateral sclerosis (ALS), hereditary spastic paraplegia (HSP), primary lateral sclerosis (PLS), progressive muscular atrophy (PMA), progressive bulbar palsy (PBP) and pseudobulbar palsy.

Cognitive dysfunction may be understood to refer to reduced cognitive abilities in a patient including reduced ability in learning, memory loss, perception, and problem solving. Cognitive dysfunction is associated with a range of conditions, such as Alzheimer's disease, Parkinson's disease, progressive supranuclear palsy, corticobasal degeneration and schizophrenia. Accordingly, in particular embodiments, the compounds of the invention may be used in the treatment of cognitive dysfunction in Alzheimer's disease, Parkinson's disease, progressive supranuclear palsy, corticobasal degeneration or schizophrenia. Cognitive dysfunction also includes post-operative cognitive dysfunction and impaired cognition associated with preterm delivery.

Similarly, in other particular embodiments, the compounds of the invention may be used in improving cognition in a patient with Alzheimer's disease, Parkinson's disease, progressive supranuclear palsy, corticobasal degeneration or schizophrenia. As used herein, the phrase "improving cognition" may be understood to indicate enhancing a patient's learning, memory, perception, and/or problem-solving ability. Improving cognition may also refer to slowing or arresting the rate of decline in cognition in a patient suffering from cognitive dysfunction (e.g. associated with the disorders listed above).

Cognitive function may be assessed using standard tests known to the person skilled in the art. Examples of such tests include the Alzheimer's Disease Assessment Scale-Cognitive subscale test (ADAS-COG) the Mini-Mental State Examination (MMSE), the Clinical Dementia Rating (CDR) the Clinical Dementia Rating-Sum of Boxes (CDR-SB), the Alzheimer's Disease Cooperative Study—Preclinical Alzheimer Cognitive Composite (ADCS-PACC) and the Repeatable Battery for the Assessment of Neuropsychological Status (RBANS) test.

As used herein, "eating disorders" may be understood to include hyperphagia, anorexia nervosa, restricting anorexia nervosa and bulimia nervosa.

In accordance with a further aspect of the invention, there is provided the compounds of the invention, or a pharmaceutically acceptable salt thereof, for use in treatment and/or prevention of one or more disease selected from the group comprising or containing Alzheimer's disease, Lewy body dementia, frontotemporal dementia, HIV dementia, Huntington's disease, amyotrophic lateral sclerosis and other motor neurone diseases, Rett syndrome, epilepsy, Parkinson's disease and other parkinsonian disorders, disorders in which enhancement of nerve regeneration is beneficial, such as demyelinating diseases including multiple sclerosis, spinal cord injury, stroke, hypoxia, ischemia, brain injury including traumatic brain injury, mild cognitive impairment, dementia disorders (including dementia of mixed vascular and degenerative origin, presenile dementia, senile dementia and dementia associated with Parkinson's disease, progressive supranuclear palsy or corticobasal degeneration) and cognitive dysfunction in schizophrenia, obesity, diabetes and metabolic syndrome, diabetic neuropathy including associated disorders such as osteoporosis, painful connective tissue disorders and tendon ruptures, Charcot Marie Tooth disease and its variants, nerve transplantation and its complications, motor neurone disease, peripheral nerve injury, genetic, acquired or traumatic hearing loss, blindness and posterior eye diseases, depression, obesity, metabolic syndrome, pain, depression, schizophrenia, anxiety and constipation, particularly, constipation in Parkinson's disease, slow-transit constipation and opioid-induced constipation.

In accordance with a further aspect of the invention, there is provided the compounds of the invention, or a pharmaceutically acceptable salt thereof, for use in treatment and/or prevention of one or more disease selected from the group comprising or containing Alzheimer's disease, Lewy body dementia, frontotemporal dementia, HIV dementia, Huntington's disease, amyotrophic lateral sclerosis and other motor neurone diseases, Rett syndrome, epilepsy, Parkinson's disease and other parkinsonian disorders, disorders in which enhancement of nerve regeneration is beneficial, such as demyelinating diseases including multiple sclerosis, spinal cord injury, stroke, hypoxia, ischemia, brain injury including traumatic brain injury, mild cognitive impairment, dementia disorders (including dementia of mixed vascular and degenerative origin, presenile dementia, senile dementia and dementia associated with Parkinson's disease, progressive supranuclear palsy or corticobasal degeneration) and cognitive dysfunction in schizophrenia, obesity, diabetes and metabolic syndrome, diabetic neuropathy including associated disorders such as osteoporosis, (diabetes-induced osteoporosis), painful connective tissue disorders and tendon ruptures, Charcot Marie Tooth disease and its variants, nerve transplantation and its complications, motor neurone disease, peripheral nerve injury, genetic or acquired or traumatic hearing loss, blindness and posterior eye diseases, anterior eye diseases, depression, obesity, metabolic syndrome, pain, depression, schizophrenia, anxiety and constipation, particularly, constipation in Parkinson's disease, slow-transit constipation and opioid-induced constipation.

In accordance with a further aspect of the invention, there is provided the compounds of the invention, or a pharmaceutically acceptable salt thereof, for use in treatment and/or prevention of one or more disease selected from the group comprising or containing Alzheimer's disease, Lewy body dementia, frontotemporal dementia, HIV dementia, Huntington's disease, amyotrophic lateral sclerosis and other motor neurone diseases, Rett syndrome, epilepsy, Parkinson's disease and other parkinsonian disorders, disorders in which enhancement of nerve regeneration is beneficial, such as demyelinating diseases including multiple sclerosis, spinal cord injury, stroke, hypoxia, ischemia, brain injury including traumatic brain injury, mild cognitive impairment, dementia disorders (including dementia of mixed vascular and degenerative origin, presenile dementia, senile dementia and dementia associated with Parkinson's disease, progressive supranuclear palsy or corticobasal degeneration) and cognitive dysfunction in schizophrenia, obesity, diabetes and metabolic syndrome, diabetic neuropathy including associated disorders such as osteoporosis, painful connective tissue disorders and tendon ruptures, Charcot Marie Tooth disease and its variants, nerve transplantation and its complications, motor neurone disease, peripheral nerve injury, genetic, acquired or traumatic hearing loss, blindness and posterior eye diseases, depression, obesity, metabolic syndrome, pain, depression, schizophrenia and anxiety.

In more particular embodiments, the disease characterised by impaired signalling of neurotrophins and/or other trophic factors is selected from the group consisting of Alzheimer's disease, Parkinson's disease, other Parkinsonian diseases, other tauopathies, Lewy body dementia, motor neurone disease, Pick disease, obesity, metabolic syndrome, diabetes, diabetic neuropathy, constipation and Rett syndrome.

In more particular embodiments, the disease characterised by impaired signalling of neurotrophins and/or other trophic factors is selected from the group consisting of Alzheimer's disease, Parkinson's disease, other Parkinsonian diseases, other tauopathies, Lewy body dementia, motor neurone disease, Pick disease, obesity, metabolic syndrome, diabetes, diabetic neuropathy and Rett syndrome.

In more particular embodiments, the disease characterised by impaired signalling of neurotrophins and/or other trophic factors is selected from the group consisting of Alzheimer's disease, Parkinson's disease, other Parkinsonian diseases, other tauopathies, Lewy body dementia, motor neurone disease, Pick disease, obesity, metabolic syndrome, diabetes and Rett syndrome. The treatment of this group of disorders may be particularly effective in patients having the Val66Met mutation in the BDNF gene.

In yet more particular embodiments, the disease characterised by impaired signalling of neurotrophins and/or other trophic factors is an eye disorder.

In yet more particular embodiments, the disease characterised by impaired signalling of neurotrophins and/or other trophic factors is an eye disorder selected from the group consisting of blindness, posterior eye diseases, anterior eye diseases, dry eye disease, neurotrophic keratitis, glaucoma, high intraocular pressure and retinitis pigmentosa. More particularly, the eye disorder is selected from the group consisting of dry eye disease, neurotrophic keratitis and glaucoma.

In yet more particular embodiments, the disease characterised by impaired signalling of neurotrophins and/or other trophic factors is selected from the group consisting of Alzheimer's disease, Parkinson's disease, Cognitive dysfunction, depression, diabetic neuropathy, constipation and Rett Syndrome.

In yet more particular embodiments, the disease characterised by impaired signalling of neurotrophins and/or other trophic factors is selected from the group consisting of Alzheimer's disease, Parkinson's disease, Cognitive dysfunction, depression, diabetic neuropathy and Rett Syndrome.

In yet more particular embodiments, the disease characterised by impaired signalling of neurotrophins and/or other trophic factors is selected from the group consisting of Alzheimer's disease, Parkinson's disease, Cognitive dysfunction, depression and Rett Syndrome.

A further embodiment of the invention relates to a compound of the invention, or a pharmaceutically acceptable salt thereof, for use in treatment and/or prevention of Alzheimer's disease, Lewy body dementia, frontotemporal dementia, HIV dementia, Huntington's disease, amyotrophic lateral sclerosis and other motor neuron diseases, Rett syndrome, epilepsy, Parkinson's disease and/or other Parkinsonian disorders.

A further embodiment of the invention relates to a compound of the invention, or a pharmaceutically acceptable salt thereof, for use in treatment and/or prevention of Alzheimer's disease, Parkinson's disease, Cognitive dysfunction in Schizophrenia, Rett's Syndrome and/or depression.

A further embodiment of the invention relates to a compound of the invention, or a pharmaceutically acceptable salt thereof, for use in treatment and/or prevention of Alzheimer's disease.

A further embodiment of the invention relates to a compound of the invention, or a pharmaceutically acceptable salt thereof, for use in treatment and/or prevention of depression.

A further embodiment of the invention relates to a compound of the invention, or a pharmaceutically acceptable salt thereof, for use in treatment and/or prevention of a disease where enhancement of nerve regeneration is beneficial, such as demyelinating diseases.

A further embodiment of the invention relates to a compound of the invention, or a pharmaceutically acceptable salt thereof, for use in treatment and/or prevention of multiple sclerosis.

A further embodiment of the invention relates to a compound of the invention, or a pharmaceutically acceptable salt thereof, for use in treatment and/or prevention of Rett syndrome.

A further embodiment of the invention relates to a compound of the invention, or a pharmaceutically acceptable salt thereof, for use in treatment and/or prevention spinal cord injury, stroke, hypoxia, ischemia and/or brain injury including traumatic brain injury.

A further embodiment of the invention relates to a compound of the invention, or a pharmaceutically acceptable salt thereof, for use in the treatment and/or prevention of mild cognitive impairment, dementia disorders (including dementia of mixed vascular and degenerative origin, presenile dementia, senile dementia and dementia associated with Parkinson's disease, progressive supranuclear palsy, corticobasal degeneration, post-operative dementia) and/or cognitive dysfunction in schizophrenia.

A further embodiment of the invention relates to a compound of the invention, or a pharmaceutically acceptable salt thereof, for use in the treatment and/or prevention of atherosclerosis, obesity, diabetes and metabolic syndrome, diabetic neuropathy including complications thereof such as osteoporosis, painful connective tissue disorders and tendon ruptures, Charcot Marie Tooth disease and its variants, nerve transplantation and its complications, diabetes induced osteoporosis, motor neurone disease, peripheral nerve injury, genetic or acquired or traumatic hearing loss, blindness and posterior eye diseases, depression, obesity, metabolic syndrome, WAGR syndrome, Prader Willi syndrome and/or pain.

A further embodiment of the invention relates to a compound of the invention, or a pharmaceutically acceptable salt thereof, for use in the treatment and/or prevention of atherosclerosis, obesity, diabetes and metabolic syndrome, diabetic neuropathy including complications thereof such as osteoporosis, painful connective tissue disorders and tendon ruptures, Charcot Marie Tooth disease and its variants, nerve transplantation and its complications, motor neurone disease, peripheral nerve injury, genetic or acquired or traumatic hearing loss, blindness and posterior eye diseases, depression, obesity, metabolic syndrome and/or pain.

A further embodiment of the invention relates to a compound of the invention, or a pharmaceutically acceptable salt thereof, for use in the treatment and/or prevention of depression, schizophrenia and/or anxiety.

Another embodiment relates to a use of a compound of the invention, or a pharmaceutically acceptable salt thereof, for the treatment and/or prevention of a disease in which modulators of neurotrophin receptors, such as TrkA, TrkB, TrkC and/or their signalling and receptor tyrosine kinases, such as FGFR1 and IGF1R and/or their signalling are beneficial, such as for the treatment and/or prevention of both non-neurological and neurological diseases, including one or more of the conditions mentioned hereinbefore.

The invention further relates to the use of a compound of the invention in a method of treating, preventing or reducing the risk of a disease in which modulators of neurotrophin receptors, such as TrkA, TrkB, TrkC and/or their signalling and receptor tyrosine kinases, such as FGFR1 and IGF1R and/or their signalling, are beneficial, such as in the treatment and/or prevention of both non-neurological and neurological diseases.

One embodiment relates to the use of a compound of the invention (for example in the manufacture of a pharmaceutical medicament) for use in a method of treating, preventing or reducing the risk of, one or more disease mentioned hereinbefore, which comprises administering to a mammal, such as a human, in need thereof, a therapeutically effective amount of a compound of the invention, or a pharmaceutically acceptable salt thereof.

Another embodiment relates to such a use of a compound of the invention in a method of treating, preventing or reducing the risk of Alzheimer's disease, Lewy body dementia, frontotemporal dementia, HIV dementia, Huntington's disease, amyotrophic lateral sclerosis and other motor neuron diseases, Rett syndrome, epilepsy, Parkinson's disease and/or other parkinsonian disorders.

A further embodiment relates to such a use of a compound of the invention in a method of treating, preventing or reducing the risk of Alzheimer's disease, Parkinson's disease, Cognitive dysfunction in Schizophrenia, Rett's Syndrome and/or Depression.

A further embodiment relates to such a use of a compound of the invention in a method of treating, preventing or reducing the risk of a disease where enhancement of nerve regeneration is beneficial such as demyelinating diseases, such as multiple sclerosis.

A further embodiment relates to such a use of a compound of the invention in a method of treating, preventing or reducing the risk of spinal cord injury, stroke, hypoxia, ischemia and/or brain injury including traumatic brain injury.

A further embodiment relates to such a use of a compound of the invention in a method of treating or preventing constipation, particularly constipation in Parkinson's disease, slow-transit constipation and opioid-induced constipation.

Another embodiment relates to such a use of a compound of the invention in a method of treating, preventing or reducing the risk of mild cognitive impairment, dementia disorders (including dementia of mixed vascular and degenerative origin, presenile dementia, senile dementia and dementia associated with Parkinson's disease, progressive supranuclear palsy or corticobasal degeneration) and/or cognitive dysfunction in schizophrenia.

A further embodiment relates to such a use of a compound of the invention in a method of treating, obesity, diabetes and metabolic syndrome, diabetic neuropathy including complications thereof such as osteoporosis, painful connective tissue disorders and tendon ruptures, Charcot Marie Tooth disease and its variants, nerve transplantation and its complications, diabetes-induced osteoporosis, motor neuron disease, peripheral nerve injury, genetic or acquired or traumatic hearing loss, blindness and posterior eye diseases, depression, obesity, metabolic syndrome and/or pain.

A further embodiment relates to such a use of a compound of the invention in a method of treating, obesity, diabetes and metabolic syndrome, diabetic neuropathy including complications thereof such as osteoporosis, painful connective tissue disorders and tendon ruptures, Charcot Marie Tooth disease and its variants, nerve transplantation and its complications, motor neuron disease, peripheral nerve injury, genetic or acquired or traumatic hearing loss, blindness and posterior eye diseases, depression, obesity, metabolic syndrome and/or pain.

Yet another embodiment relates to such a use of a compound of the invention in a method of treating, preventing or reducing the risk of depression, schizophrenia and/or anxiety.

As described above, treatment of the disorders described herein with the compounds of the invention may be particularly effective in patients with the Val66Met mutation in the BDNF gene. Accordingly, in particular embodiments, the treatment of the disorders characterised by impaired signalling of neurotrophins and/or other trophic factors as defined herein (including the various embodiments described herein) is in a patient with the Val66Met mutation in the BDNF gene.

Pharmaceutical Compositions

As described herein, compounds of the invention are useful as pharmaceuticals. Such compounds may be administered alone or may be administered by way of known pharmaceutical compositions/formulations.

In a further aspect of the invention, there is provided a pharmaceutical composition comprising a compound of the invention, or a pharmaceutically-acceptable salt thereof, and a pharmaceutically-acceptable excipient, such as a pharmaceutically-acceptable adjuvant, diluent or carrier, for use in the treatment of a disease characterised by impaired signalling of neurotrophins and/or other trophic factors (including the various diseases and disorders listed herein), optionally in a patient with the Val66Met mutation in the BDNF gene.

As used herein, the term pharmaceutically-acceptable excipients includes references to vehicles, adjuvants, carriers, diluents, pH adjusting and buffering agents, tonicity adjusting agents, stabilizers, wetting agents and the like. In particular, such excipients may include adjuvants, diluents or carriers.

The skilled person will understand that compounds of the invention may act systemically and/or locally (i.e. at a particular site), and may therefore be administered accordingly using suitable techniques known to those skilled in the art.

The skilled person will understand that compounds and compositions as described herein will normally be administered orally, intravenously, subcutaneously, buccally, rectally, dermally, nasally, tracheally, bronchially, sublingually, intranasally, topically (including topical administration to the eyes), by any other parenteral route or via inhalation, in a pharmaceutically acceptable dosage form.

Conventional procedures for the selection and preparation of suitable pharmaceutical formulations are described in, for example, "Pharmaceuticals—The Science of Dosage Form Designs", M. E. Aulton, Churchill Livingstone, 1988. For preparing pharmaceutical compositions from the compounds of the invention, inert, pharmaceutically acceptable carriers can be either solid or liquid. Solid form preparations include powders, tablets, dispersible granules, capsules, cachets, and suppositories.

Pharmaceutical compositions as described herein will include formulations in the form of tablets, capsules or elixirs for oral administration, suppositories for rectal administration, sterile solutions or suspensions for parenteral or intramuscular administration, and the like. Alternatively, particularly where such compounds of the invention act locally, pharmaceutical compositions may be formulated for topical administration. In particular, compounds may be formulated for local delivery to the CNS, for example in the form of artificial cerebrospinal fluid (CSF).

Thus, in particular embodiments, the pharmaceutical composition is provided in a pharmaceutically acceptable dosage form, including tablets or capsules, liquid forms to be taken orally or by injection, suppositories, creams, gels, foams, inhalants (e.g. to be applied intranasally), or forms suitable for topical administration. For the avoidance of doubt, in such embodiments, compounds of the invention may be present as a solid (e.g. a solid dispersion), liquid (e.g. in solution) or in other forms, such as in the form of micelles.

Thus, compounds, of the present invention, and compositions comprising the same, may be administered orally, parenterally, buccally, vaginally, rectally, by inhalation, by insufflation, sublingually, intramuscularly, subcutaneously, topically (including topical administration to the eyes), intranasally, intraperitoneally, intrathoracically, intravenously, epidurally, intrathecally, intracerebroventricularly and by injection into the joints.

Depending on the mode of administration, pharmaceutical compositions will preferably comprise from 0.05 to 99% wt (percent by weight), more preferably from 0.05 to 80% wt, still more preferably from 0.10 to 70% wt, and even more preferably from 0.10 to 50% wt, of a compounds of the invention (calculated as a non-salt form), all percentages by weight being based on total composition.

Depending on e.g. potency and physical characteristics of the compound of the invention (i.e. active ingredient), pharmaceutical formulations that may be mentioned include those in which the active ingredient is present in an amount that is at least 1% (or at least 10%, at least 30% or at least 50%) by weight. That is, the ratio of active ingredient to the other components (i.e. the addition of adjuvant, diluent and carrier) of the pharmaceutical composition is at least 1:99 (or at least 10:90, at least 30:70 or at least 50:50) by weight.

The quantity of the compound to be administered will vary for the patient being treated and will vary from about 100 ng/kg of body weight to 100 mg/kg of body weight per day. For instance, dosages can be readily ascertained by those skilled in the art from this disclosure and the knowledge in the art. Thus, the skilled artisan can readily determine the amount of compound and optional additives, vehicles, and/or carrier in compositions and to be administered in uses or methods of the invention.

More, particularly, the skilled person will understand that compounds of the invention may be administered (for example, as formulations as described hereinbefore) at varying doses, with suitable doses being readily determined by one of skill in the art. Oral, pulmonary and topical dosages (and subcutaneous dosages, although these dosages may be relatively lower) may range from between about 0.01 µg/kg of body weight per day (µg/kg/day) to about 14 mg/kg/day, preferably about 0.01 µg/kg/day to about 10 mg/kg/day, and more preferably about 0.1 µg/kg/day to about 5.0 mg/kg/day. For example, when administered orally, treatment with such compounds may comprise administration of a formulations typically containing between about 0.01 µg to about 1000 mg, for example between about 0.1 µg to about 500 mg, or between 1 µg to about 100 mg (e.g. about 20 µg to about 80 mg), of the active ingredient(s). When administered intravenously, the most preferred doses will range from about 0.001 to about 10 µg/kg/hour during constant rate infusion. Advantageously, treatment may comprise administration of such compounds and compositions in a single daily dose, or the total daily dosage may be administered in divided doses of two, three or four times daily (e.g. twice daily with reference to the doses described herein, such as a dose of 1 mg, 5 mg, 10 mg, 25 mg, 50 mg, 100 mg or 200 mg twice daily).

For the avoidance of doubt, the skilled person (e.g. the physician) will be able to determine the actual dosage which will be most suitable for an individual patient, which is likely to vary with the route of administration, the type of formulation, the type and severity of the condition that is to be treated, other medication the patient may be taking, as well as the species, age, weight, size, sex, diet, renal function, hepatic function, general physical condition, genetic factors and response of the particular patient to be treated. Although the above-mentioned dosages are exemplary of the average case, there can, of course, be individual instances where higher or lower dosage ranges are merited, and such doses are within the scope of the invention.

Thus, in a further aspect of the invention, there is provided a use of a pharmaceutical composition, as defined above, in therapy, or for the treatment and/or prevention of a disease characterised by impaired signalling of neurotrophins and/or other trophic factors.

Combinations and Kits-of-Parts

The treatment and/or prevention of diseases of the nervous system and related pathologies defined herein may comprise administration of a compound of the invention as a sole therapy or may involve, in addition to the compound of the invention, conjoint treatment with conventional therapy of value in treating one or more disease conditions referred to herein. Such conventional therapy may include one or more agents such as acetyl cholinesterase inhibitors, anti-inflammatory agents, cognitive and/or memory enhancing agents, atypical antipsychotic agents, dopamine agonists and/or L-DOPA.

Such conjoint treatment and/or prevention may be achieved by way of the simultaneous, sequential or separate dosing of the individual compounds of the invention or additional agents of the treatment and/or prevention. Such combination products employ the compounds, or pharmaceutically-acceptable salts thereof, of the invention.

Accordingly, the skilled person will understand that treatment with compounds of the invention may further comprise (i.e. be combined with) further treatment(s) or preventative methods for the same condition. In particular, treatment with compounds of the invention may be combined with means for the treatment of diseases characterised by impaired signalling of neurotrophins and/or other trophic factors (such as Alzheimer's disease, Parkinson's disease, cognitive dysfunction and depression as described herein, e.g. Alzheimer's disease) such as treatment with one or more other therapeutic agent that is useful in the in the treatment the various diseases characterised by impaired signalling of neurotrophins and/or other trophic factors described herein, and/or one or more physical method used in the treatment (such as treatment through surgery), as known to those skilled in the art.

As described herein, compounds of the invention may also be combined with one or more other (i.e. different) therapeutic agents (i.e. agents that are not compounds of the invention) that are useful in the treatment and/or prevention of diseases characterised by impaired signalling of neurotrophins and/or other trophic factors. Such combination products that provide for the administration of a compound of the invention in conjunction with one or more other therapeutic agent may be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the one or more other therapeutic agent).

Thus, according to a further aspect of the invention, there is provided a combination product comprising:

(I) a compound of the invention as hereinbefore defined, or a pharmaceutically acceptable salt thereof; and (II) one or more other therapeutic agent that is useful in the treatment or prevention of a disease characterised by impaired signalling of neurotrophins and/or other trophic factors, wherein each of components (I) and (II) is formulated in admixture, optionally with a pharmaceutically-acceptable excipient, such as a pharmaceutically-acceptable adjuvant diluent or carrier.

According to a further aspect of the invention there is provided a pharmaceutical composition comprising a compound of the invention as hereinbefore defined, or a pharmaceutically acceptable salt thereof and one or more other therapeutic agent that is useful in the treatment or prevention of a disease characterised by impaired signalling of neurotrophins and/or other trophic factors, fomulated together in admixture, optionally with a pharmaceutically-acceptable excipient, such as a pharmaceutically-acceptable adjuvant diluent or carrier.

According to a further aspect of the invention, there is provided a kit-of-parts comprising:

(a) a pharmaceutical composition comprising a compound of the invention as hereinbefore defined, or a pharmaceutically acceptable salt thereof, formulated in admixture, optionally with a pharmaceutically-acceptable excipient, such as a pharmaceutically-acceptable adjuvant diluent or carrier; and (b) a pharmaceutical composition comprising one or more other therapeutic agent that is useful in the treatment or prevention of a disease characterised by impaired signalling of neurotrophins and/or other trophic factors, formulated in admixture, optionally with a pharmaceutically-acceptable excipient, such as a pharmaceutically-acceptable adjuvant diluent or carrier, which components (a) and (b) are each provided in a form that is suitable for administration in conjunction with the other.

With respect to the kits-of-parts as described herein, by "administration in conjunction with" (and similarly "administered in conjunction with") we include that respective formulations are administered, sequentially, separately or simultaneously, as part of a medical intervention directed towards treatment of the relevant condition.

Thus, in relation to the present invention, the term "administration in conjunction with" (and similarly "administered in conjunction with") includes that the two active ingredients are administered (optionally repeatedly) either together, or sufficiently closely in time, to enable a beneficial effect for the patient, that is greater, over the course of the treatment and/or prevention of the relevant condition, than if either agent is administered (optionally repeatedly) alone, in the absence of the other component, over the same course of treatment and/or prevention. Determination of whether a combination provides a greater beneficial effect in respect of, and over the course of, treatment or prevention of a particular condition will depend upon the condition to be treated or prevented, but may be achieved routinely by the skilled person.

Further, in the context of the present invention, the term "in conjunction with" includes that one or other of the two formulations may be administered (optionally repeatedly) prior to, after, and/or at the same time as, administration of the other component. When used in this context, the terms "administered simultaneously" and "administered at the same time as" includes instances where the individual doses of the compound of the invention and the additional compound for the treatment of a disease characterised by impaired signalling of neurotrophins and/or other trophic factors, or pharmaceutically acceptable salts thereof, are administered within 48 hours (e.g. within 24 hours, 12 hours, 6 hours, 3 hours, 2 hours, 1 hour, 45 minutes, 30 minutes, 20 minutes or 10 minutes) of each other.

Other therapeutic agents useful in the treatment or prevention of diseases characterised by impaired signalling of neurotrophins and/or other trophic factors will be well-known to those skilled in the art. For example, such other therapeutic agents may include: acetyl cholinesterase inhibitors, anti-inflammatory agents, cognitive enhancing agents, memory enhancing agents, and atypical antipsychotic agents, anti-depressive agents, anti-Alzheimer's agents, beta-secretase inhibitors, gamma-secretase modulators, agents modifying tau function, amyloid-beta production inhibitors, antibodies directed at amyloid-beta, antibodies directed at tau, antibodies directed at alpha-synuclein, anti-Parkinson agents, anti-diabetic agents, anti-multiple sclerosis agents, anti-obesity agents, agents used for treatment of auditory dysfunction, agents used for treatment of ocular disease, agents used for the treatment of olfactory dysfunction, agents used for the treatment of gustatory dysfunction, anti-Huntington agents, anti-Rett syndrome agents, anti-stroke agents. Particular therapeutic agents that may be mentioned include acetyl cholinesterase inhibitors, anti-Alzheimer's agents, anti-Parkinson agents, cognitive enhancing agents, antibodies directed at amyloid-beta, antibodies directed at tau, antibodies directed at alpha-synuclein, beta-secretase inhibitors and gamma-secretase modulators, anti-constipation agents (such as laxatives, serotonin agonists and chloride channel activators).

Preparation of Compositions

Pharmaceutical compositions/formulations, combination products and kits as described herein may be prepared in accordance with standard and/or accepted pharmaceutical practice.

Thus, in a further aspect of the invention there is provided a process for the preparation of a pharmaceutical composition/formulation, as hereinbefore defined, which process comprises bringing into association a compound of the invention, as hereinbefore defined, with one or more pharmaceutically-acceptable excipient.

In further aspects of the invention, there is provided a process for the preparation of a combination product or kit-of-parts as hereinbefore defined, which process comprises bringing into association a compound of the invention, as hereinbefore defined, with the other therapeutic agent that is useful in the treatment of the relevant disease or disorder, and at least one pharmaceutically-acceptable excipient.

As used herein, references to bringing into association will mean that the two components are rendered suitable for administration in conjunction with each other.

Thus, in relation to the process for the preparation of a kit-of-parts as hereinbefore defined, by bringing the two components "into association with" each other, we include that the two components of the kit-of-parts may be:

(i) provided as separate formulations (i.e. independently of one another), which are subsequently brought together for use in conjunction with each other in combination therapy; or (ii) packaged and presented together as separate components of a "combination pack" for use in conjunction with each other in combination therapy.

Preparation of Compounds of the Invention

Compounds of the invention as described herein may be prepared either as a free base or as a pharmaceutically acceptable salt in accordance with techniques that are well known to those skilled in the art, such as those described in the examples provided hereinafter.

According to a further aspect of the invention there is provided a process for the preparation of a compound of the invention, which comprises the step of reaction of a compound of formula II,

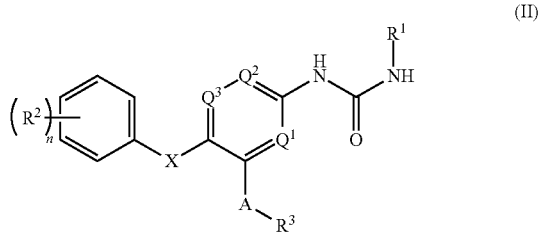

(II)

wherein $R^1$, $R^2$, $R^3$, $Q^1$, $Q^2$, $Q^3$, A, X and n are as hereinbefore defined, with ethoxycarbonyl isocyanate.

This reaction may be performed for example:

a. in a sealed microwave vial in a suitable solvent (such as toluene or bromobenzene), at a suitable reaction temperature (e.g. between room temperature and reflux temperature); or b. by first treating the compound of formula II with a suitable base, such as sodium hydride, at a suitable reaction temperature (e.g. between 0° C. and room temperature) for between about 1 and about 60 minutes in a suitable solvent, such as DMF, followed by the addition of the ethoxycarbonyl isocyanate at approximately the same, with stirring, for a suitable time, such as between about 1 and about 60 minutes.

Compounds of formula II may be obtained by reacting a compound of formula III,

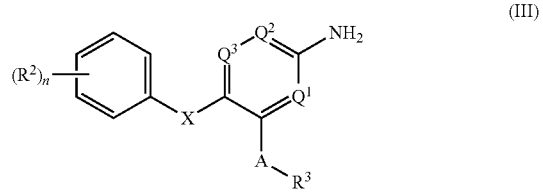

(III)

wherein $R^2$, $R^3$, $Q^1$, $Q^2$, $Q^3$, A, X and n are as hereinbefore defined, with either:

a. a compound of formula IV,

$R^1$—N=C=O     (IV)

wherein $R^1$ is as hereinbefore defined; or b. a compound of formula V,

$R^1$—N(H)C(O)Cl     (V)

wherein $R^1$ is as hereinbefore defined, for example (in both cases) in the presence of a suitable base, such as TEA, in a suitable solvent, such as DCM, THF or, pyridine, at a suitable reaction temperature (for example between room temperature and reflux temperature).

Compounds of formula II may alternatively be obtained by reacting a compound of formula VI,

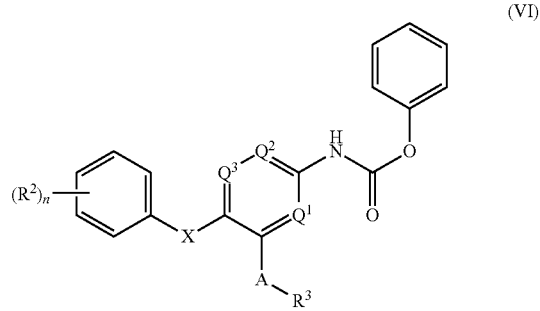

(VI)

wherein $R^2$, $R^3$, $Q^1$, $Q^2$, $Q^3$, X, A and n are as hereinbefore defined, with an amine of formula VII,

$R^1$—NH$_2$     (VII)

wherein $R^1$ is as hereinbefore defined, for example in the presence of a suitable base, such as TEA, in a suitable solvent, such as THF, and at a suitable reaction temperature (e.g. between room temperature and reflux temperature).

Compounds of formula II may alternatively be prepared by reacting a compound of formula III as hereinbefore defined with triphosgene or phosgene in the presence of a suitable base, such as NaHCO$_3$ or TEA, in a suitable solvent, such as DCM, and at a suitable reaction temperature (e.g. between 0° C. and room temperature). After a suitable period of time, such as between about 1 and about 6 hours, a compound of formula VII may be added, together with an additional amount of a suitable (e.g. the above-mentioned) base, which reaction mixture is then allowed to react at a suitable temperature, such as room temperature, for a suitable period of time, such as between about 1 and about 24 hours. Alternatively, the sequence of this reaction may be altered by first reacting a compound of formula IV with triphosgene or phosgene, followed by the addition of the compound of formula VII, under substantially the same reaction conditions as described above.

Compounds of formula III may be obtained by reducing a compound of formula VIII,

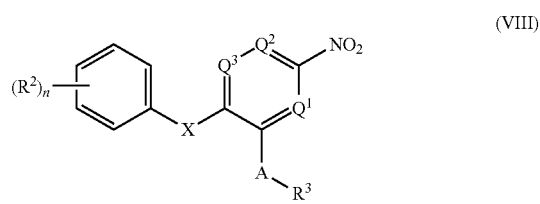

(VIII)

wherein $R^2$, $R^3$, $Q^1$, $Q^2$, $Q^3$, X, A and n are as hereinbefore defined, in the presence of a suitable reducing agent such as SnCl$_2$·2H$_2$O, for example in the presence of HCl, or using Pd/C in the presence of H$_2$(g). This reaction may be performed in a suitable solvent, such as ethanol, and at a suitable temperature (for example between room temperature and reflux temperature).

In a further embodiment of the invention, there is provided a process for the preparation of a compound of the invention from a compound of formula IX,

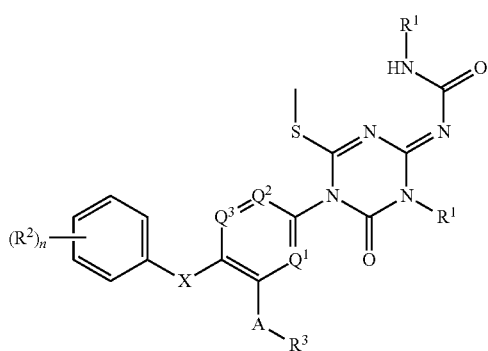

(IX)

wherein $R^1$, $R^2$, $R^3$, $Q^1$, $Q^2$, $Q^3$, X, A and n are as hereinbefore defined, particularly wherein $R^1$ represents a phenyl or heteroaryl group as defined herein (more particularly wherein $R^1$ represents phenyl or tolyl), in the presence of a suitable acid (such as HCl (e.g. 2M HCl)) and optionally an organic co-solvent (e.g. 1,4-dioxane), and at a suitable temperature (for example at between room temperature and reflux temperature).

Compounds of formula IX may be obtained by reacting a compound of formula X

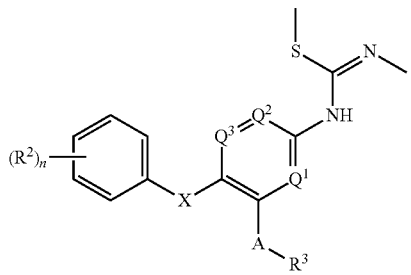

(X)

wherein wherein $R^2$, $R^3$, $Q^1$, $Q^2$, $Q^3$, X, A and n are as hereinbefore defined, particularly wherein $R^1$ represents an phenyl or heteroaryl group as defined herein (more particularly wherein $R^1$ represents phenyl or tolyl), with an excess (e.g. 2 equivalents) of a compound of formula XI,

$R^1$—N=C=O    (XI)

wherein $R^1$ is as hereinbefore defined, particularly wherein $R^1$ represents an aryl or heteroaryl group as defined herein (more particularly wherein $R^1$ represents phenyl), in the presence of a suitable base (e.g triethylamine), a suitable solvent (e.g. acetonitrile), and a suitable reagent (e.g. 1,1′-carbonyldiimidazole (CDI)) at a suitable temperature (e.g, room temperature).

Compounds of formulae IV, V, VI, VII, VIII and XI are either commercially available, are known in the literature, or may be obtained either by analogy with the processes described herein, or by conventional synthetic procedures, in accordance with standard techniques, from available starting materials using appropriate reagents and reaction conditions. In this respect, the skilled person may refer to inter alia "Comprehensive Organic Synthesis" by B. M. Trost and I. Fleming, Pergamon Press, 1991. Further references that may be employed include "Heterocyclic Chemistry" by J. A. Joule, K. Mills and G. F. Smith, 3rd edition, published by Chapman & Hall, "Comprehensive Heterocyclic Chemistry II" by A. R. Katritzky, C. W. Rees and E. F. V. Scriven, Pergamon Press, 1996 and "Science of Synthesis", Volumes 9-17 (Hetarenes and Related Ring Systems), Georg Thieme Verlag, 2006.

The skilled person will understand that the substituents as defined herein, and substituents thereon, may be modified one or more times, after or during the processes described above for the preparation of compounds of the invention by way of methods that are well known to those skilled in the art. Examples of such methods include substitutions, reductions, oxidations, dehydrogenations, alkylations, dealkylations, acylations, hydrolyses, esterifications, etherifications, halogenations and nitrations. The precursor groups can be changed to a different such group, or to the groups defined in formula I, at any time during the reaction sequence. The skilled person may also refer to "Comprehensive Organic Functional Group Transformations" by A. R. Katritzky, O. Meth-Cohn and C. W. Rees, Pergamon Press, 1995 and/or "Comprehensive Organic Transformations" by R. C. Larock, Wiley-VCH, 1999.

Compounds of the invention may be isolated from their reaction mixtures and, if necessary, purified using conventional techniques as known to those skilled in the art. Thus, processes for preparation of compounds of the invention as described herein may include, as a final step, isolation and optionally purification of the compound of the invention.

It will be appreciated by those skilled in the art that, in the processes described above and hereinafter, the functional groups of intermediate compounds may need to be protected by protecting groups. The protection and deprotection of functional groups may take place before or after a reaction in the above-mentioned schemes.

Protecting groups may be applied and removed in accordance with techniques that are well-known to those skilled in the art and as described hereinafter. For example, protected compounds/intermediates described herein may be converted chemically to unprotected compounds using standard deprotection techniques. The type of chemistry involved will dictate the need, and type, of protecting groups as well as the sequence for accomplishing the synthesis. The use of protecting groups is fully described in "Protective Groups in Organic Synthesis", 3rd edition, T. W. Greene & P. G. M. Wutz, Wiley-Interscience (1999), the contents of which are incorporated herein by reference.

When used herein in relation to a specific value (such as an amount), the term "about" (or similar terms, such as "approximately") will be understood as indicating that such values may vary by up to 10% (particularly, up to 5%, such as up to 1%) of the value defined. It is contemplated that, at each instance, such terms may be replaced with the notation "±10%", or the like (or by indicating a variance of a specific amount calculated based on the relevant value). It is also contemplated that, at each instance, such terms may be deleted.

Compounds of the invention may have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise. In particular, compounds of the invention may have the advantage that they are more efficacious and/or exhibit advantageous properties in vivo.

EXAMPLES

The present invention will be further described by reference to the following examples, which are not intended to limit the scope of the invention.

Experimental Procedures

Starting materials and intermediates used in the synthesis of compounds described herein are commercially available or can be prepared by the methods described herein or by methods known in the art.

Experiments were generally carried out under inert atmosphere (nitrogen or argon), particularly in cases where oxygen- or moisture-sensitive reagents or intermediates were used.

Mass spectrometry data are reported from liquid chromatography-mass spectrometry (LC-MS) using electrospray ionization. Chemical shifts for NMR data are expressed in parts per million (ppm, δ) referenced to residual peaks from the deuterated solvent used.

For syntheses referencing general procedures, reaction conditions (such as length of reaction or temperature) may vary. In general, reactions were followed by thin layer chromatography or LC-MS, and subjected to work-up when appropriate. Purifications may vary between experiments: in general, solvents and the solvent ratios used for eluents/gradients were chosen to provide an appropriate $R_f$ and/or retention time.

General Methods

All solvents were of analytical grade and commercially available anhydrous solvents were routinely used for reactions. Starting materials used were available from commercial sources or prepared according to literature procedures, Room temperature refers to 20-25° C. Solvent mixture compositions are given as volume percentages or volume ratios.

MW heating was performed in a standard MW reactor producing continuous irradiation at 2450 MHz. It is understood that MWs can be used for the heating of reaction mixtures. Typically, an Anton paar microwave synthesizer 300 was used as a microwave synthesizer.

Thin layer chromatography (TLC) was performed on Merck TLC-plates (Silica gel 60 $F_{254}$) and spots were UV visualized. TLC was generally used to monitor reaction progression and solvents used were for example: ethyl acetate or acetonitrile or DCM with 1-10% of MeOH, ethyl acetate with 0-95% hexane. Straight phase flash column chromatography ("flash chromatography"/"column chromatography") was manually performed on Merck Silica gel 60 (0.040-0.063 mm) or basic aluminum oxide or neutral aluminum oxide, or automatically using ISCO Combiflash® Companion™ system using RediSep™ normal-phase flash columns ("Combiflash") using the solvent system indicated.

NMR spectra was recorded on a 400 MHz NMR spectrometer (Bruker 400 MHz Avance-III) fitted with a probe of suitable configuration. Spectra were recorded at ambient temperature unless otherwise stated. Chemical fields are given in ppm down- and upfield from TMS (0.00 ppm). The following reference signals were used in $^1$H-NMR: TMS δ 0.00, or residual solvent signal of DMSO-d6 δ 2.49, CDCl$_3$ δ 7.25 (unless otherwise indicated). Resonance multiplicities are denoted s, d, t, q, m, dd, tt, dt br and app for singlet, doublet, triplet, quartet, doublet of doublet, triplet of triplet, doublet of triplet, multiplet, broad and apparent, respectively. In some cases only diagnostic signals are reported.

High pressure liquid chromatography (HPLC) was performed on a reversed phase (RP) column. A gradient was applied using for example mobile phase A (5 mM Ammonium acetate+0.1% Formic acid in water) and B (0.1% Formic acid in Acetonitrile) or A (0.1% NH3 in water) and B (0.1% NH3 in acetonitrile) or A (10 mM Ammonium actetate in water) and B (Acetonitrile).

Reversed phase columns used were for example: BEH C18 (50*2.1 mm), 1.7 μm; X-Bridge C18 (50*4.6 mm), 3.5 μm; X-Bridge/YMCC18 (150*4.6 mm), 5 μm; BEH C18 (50*2.1 mm), 1.7 μm; X-Bridge C8 (250*19) mm, 5 μm. The flowrate used was for example 0.55 ml/min or 1.00 ml/min Mass spectrometry (MS) analysis were performed in positive and/or negative ion mode using electrospray ionization (ESI+/−).

Preparative HPLC chromatography was run on a Waters e2695 Separation Module with a PDA Detector or on a Shimadzu LC-20AP with an UV detector. Column; X-BRIDGE C18, 150*4.6 mm, 5 μm or X-Bridge C18 (250*19 mm) 5 μm or GEMINI C18 (250*21.2 mm) 5 μm or sunfire c18(150*19)mm, 5 micron or x-bridge c18 (150*19)mm, 5 micron or ymc actus triart c18(150*20)mm, 5 micron or kromasil eternity c18 (250*21.2)mm, 5 micron. The flowrate used was for example 10-15 ml/min. The UV spectra were typically recorded at 202 nm & between 214 and 260 nm Lambda max.

A gradient was applied using for example mobile phase A (0.1% NH$_3$ in water) and B (0.1% NH3 in acetonitrile); A (0.1% TFA in water) and B (Acetonitrile); A (5 mM ammonium bicarbonate+0.05% ammonia in water) and B (Acetonitrile); A (5 mM ammonium bicarbonate) and B (acetonitrile) for LC-separation at a flow rate 1 ml/min.

High pressure liquid chromatography (HPLC) was performed on a straight phase column. A linear gradient or isocratic flow was applied using for example phase A (Hexane) and B (XX)

Compounds have been named using CDD vault from Collaborative Drug Discovery Inc. Burlingame Calif., USA or ChemDoodle 8.1.0/9.02 from iChemLabs LLC, USA or ACD/ChemSketch 2012 (14.01) from Advanced Chemistry Development (ACD/labs) Ontario, Canada. In case of inconsistency between a name of a compound and the structural formula of the same compound, it is the structural formula that is decisive for the molecular structure of the compound.

In the event that there is a discrepancy between nomenclature and any compounds depicted graphically, then it is the latter that presides (unless contradicted by any experimental details that may be given or unless it is clear from the context).

Intermediate 1

1-(5-nitro-2-phenoxybenzyl)-1H-pyrazole

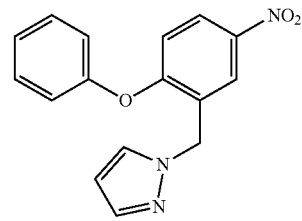 [SMILES: O=[N+]([O-])c1ccc(Oc2ccccc2)c(Cn2cccn2)c1]

In a RBF previously equipped with a magnetic stirrer and nitrogen balloon was taken pyrazole (0.24 g, 3.5 mmol) and acetonitrile. The resultant solution was cooled to 0° C. and K$_2$CO$_3$ (0.49 g, 3.5 mmol) was added and reaction mixture was stirred for 10 min. 2-(Bromomethyl)-4-nitro-1-phenoxybenzene (commercially available, 0.50 g, 1.6 mmol) was added drop wise to the reaction mixture and stirred at room temperature for 16 h. The solvent was evaporated and reaction mixture was quenched with ice-water (30 ml) and product was extracted with ethyl Acetate (3×30 ml). The combined organic layer was washed with brine (20 ml). The organic layer was dried over sodium sulphate and the solvent removed under reduced pressure. The crude product was purified by column chromatography using silica gel (60-120 mesh) and 7% ethyl acetate in hexanes as an eluent to obtain 0.40 g (83%) of the title compound. $^1$H NMR (400 MHz, DMSO-$d_6$) δ 8.16 (dd, J=8.8, 2.8 Hz, 1H), 7.91 (d, J=1.6 Hz, 1H), 7.84 (d, J=2.4 Hz, 1H), 7.56-7.49 (m, 3H), 7.32 (t, J=7.2 Hz, 1H), 7.15 (d, J=7.6 Hz, 2H), 6.86 (d, J=9.2 Hz, 1H), 6.34 (t, J=2.0 Hz, 1H), 5.58 (s, 2H); MS (ES+) m/z 296 [M+H]$^+$.

Intermediate 2

4-phenoxy-3-(1H-pyrazol-1-ylmethyl)aniline

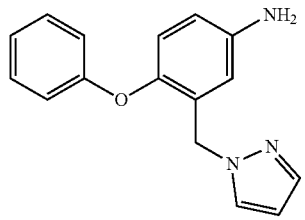 [SMILES: Nc1ccc(Oc2ccccc2)c(Cn2cccn2)c1]

In a RBF previously equipped with a magnetic stirrer and nitrogen balloon was taken 1-(5-nitro-2-phenoxybenzyl)-1H-pyrazole (Intermediate 1, 0.250 g, 12 mmol) and methanol (10 ml). 10% Pd/C (50% wet) (0.05 g) was added to stirred solution under $N_2$ atmosphere. The mixture was stirred for 3 h under $H_2$ (g). The reaction mixture was filtered through celite bed, washed with methanol and the solvent was removed under reduced pressure to obtain 0.210 g (93% yield) of the title compound. $^1$H NMR (400 MHz, DMSO-$d_6$): δ 7.61 (d, J=2.0 Hz, 1H), 7.43 (d, J=1.2 Hz, 1H), 7.31 (t, J=7.6 Hz, 2H), 7.02 (t, J=7.6 Hz, 1H), 6.85 (d, J=8.0 Hz, 2H), 6.71 (d, J=8.8 Hz, 1H), 6.52 (dd, J=8.4, 2.8 Hz, 1H), 6.25-6.22 (m, 2H), 5.11 (s, 2H), 5.05 (s, 2H); MS (ES+) m/z 266 [M+H]$^+$.

Intermediate 3

1-[4-phenoxy-3-(1H-pyrazol-1-ylmethyl)phenyl]-3-phenylurea

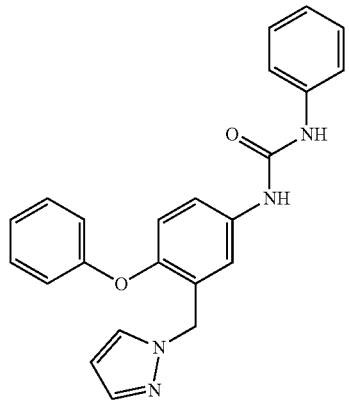 [SMILES: O=C(Nc1ccccc1)Nc1ccc(Oc2ccccc2)c(Cn2cccn2)c1]

In a RBF previously equipped with a magnetic stirrer was taken 4-phenoxy-3-(1H-pyrazol-1-ylmethyl)aniline (Intermediate 2, 0.21 g, 0.7 mmol) and TEA (0.22 ml) in DCM (2 ml) and the mixture was cooled to 0° C. To the mixture, phenyl isocyanate (0.11 g, 0.9 mmol) was added and reaction mixture was allowed to reach 25° C. and stirred for 16 h. The reaction mixture was quenched with ice-water (10 ml). The product was extracted with DCM (3×20 ml) and the combined organic layer was washed with brine (10 ml), dried over sodium sulphate and the solvent evaporated under reduced pressure. The crude product was purified by column chromatography on silica gel (100-200 mesh) using 12% ethyl acetate in hexanes as an eluent to obtain 0.16 g (52% yield) of the title compound. $^1$H NMR (400 MHz, DMSO-$d_6$) δ 8.70 (s, 1H), 8.58 (s, 1H), 7.72 (d, J=2.0 Hz, 1H), 7.52-7.32 (m, 6H), 7.27 (t, J=7.6 Hz, 2H), 7.12-7.05 (m, 2H), 6.98-6.88 (m, 4H), 6.26 (t, J=2.0 Hz, 1H), 5.30 (s, 2H); MS (ES+) m/z 385 [M+H]$^+$.

Intermediate 4

1-(5-nitro-2-phenoxybenzyl)-1H-imidazole

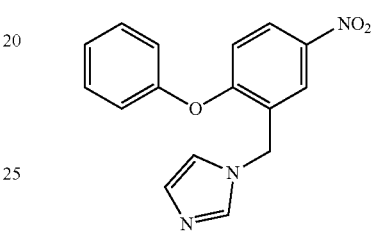

In a RBF previously equipped with a magnetic stirrer and nitrogen balloon was taken imidazole (0.09 g, 1.4 mmol) and Acetonitrile (12 ml). The mixture was cooled to 0° C. and $K_2CO_3$ (0.19 g, 1.4 mmol) was added and reaction mixture was stirred for 10 min. 2-(bromomethyl)-4-nitro-1-phenoxybenzene (commercially available, 0.20 g, 0.6 mmol) was added drop wise to the reaction mixture and stirred at room temperature for 16 h. The solvent was evaporated under reduced pressure and the crude reaction mixture was quenched with ice-water (20 ml). The product was extracted with ethyl Acetate (3×20 ml). The combined organic layer was washed with brine (20 ml). The organic layer was dried over sodium sulphate and the solvent removed under reduced pressure. The crude product was purified by column chromatography using silica gel (100-200 mesh) and 80% ethyl acetate in hexanes as an eluent to obtain 0.19 g (99%) of the title compound. $^1$H NMR (400 MHz, DMSO-$d_6$): δ 8.18 (dd, J=9.2, 2.8 Hz, 1H), 8.10 (d, J=2.8 Hz, 1H), 7.80 (s, 1H), 7.52 (t, J=7.6 Hz, 2H), 7.34 (t, J=7.2 Hz, 1H), 7.27 (s, 1H), 7.15 (d, J=7.6 Hz, 2H), 6.96 (s, 1H), 6.86 (d, J=9.2 Hz, 1H), 5.44 (s, 2H); MS (ES+) m/z 296 [M+H]$^+$.

Intermediate 5

3-(1H-imidazol-1-ylmethyl)-4-phenoxyaniline

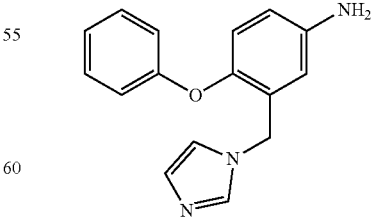

In a RBF previously equipped with a magnetic stirrer was taken 1-(5-nitro-2-phenoxybenzyl)-1H-imidazole (Intermediate 4, 0.17 g, 0.5 mmol) and $SnCl_2 \cdot 2H_2O$ (0.51 g, 2.3 mmol) in Ethanol (1.7 ml) and the mixture was cooled to 0°

C. 35% aq. HCl (0.17 ml) was added and the reaction mixture was heated to 50° C. and stirred for 5 h. The reaction mixture was diluted with ethyl acetate (30 ml) and basified with ammonia to maintain pH 7-8. The precipitates were removed by filtration via Celite® bed and the bed washed with ethyl acetate (2×20 ml). The combined filtrate was washed with water (3×15 ml) and brine (15 ml), dried over sodium sulphate and the solvent removed under reduce pressure to obtain 0.15 g (98% yield) of the title compound. $^1$H NMR (400 MHz, DMSO-d$_6$) δ 7.59 (s, 1H), 7.32 (t, J=7.6 Hz, 2H), 7.04-7.01 (m, 2H), 6.87-6.84 (m, 3H), 6.73 (d, J=8.4 Hz, 1H), 6.54 (dd, J=8.4, 2.8 Hz, 1H), 6.34 (d, J=2.8 Hz, 1H), 5.10 (s, 2H), 4.98 (s, 2H); MS (ES+) m/z 266 [M+H]$^+$.

Intermediate 6

1-[3-(1H-imidazol-1-ylmethyl)-4-phenoxyphenyl]-3-phenylurea

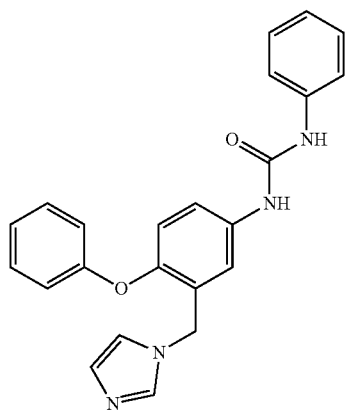 [SMILES: O=C(Nc1ccccc1)Nc1ccc(Oc2ccccc2)c(Cn2ccnc2)c1]

In a RBF previously equipped with a magnetic stirrer was taken 3-(1H-imidazol-1-ylmethyl)-4-phenoxyaniline (Intermediate 5, 0.15 g, 0.5 mmol) and TEA (0.15 ml, 1.1 mmol) in DCM (1.5 ml) and the mixture was cooled to 0° C. Phenyl isocyanate (0.08 g, 0.6 mmol) was added and the reaction mixture was allowed to reach 25° C. and stirred for 16 h. The reaction mixture was quenched with mixture of ice-water (10 ml). The product was extracted with DCM (3×20 ml) and the combined organic layer was washed with brine (10 ml, dried over sodium sulphate and the solvent removed under reduced pressure. The crude product was purified by column chromatography on silica gel (100-200 mesh) using 90% ethyl acetate in hexanes as an eluent to obtain 0.2 g (92% yield) of the title compound. MS (ES+) m/z 385 [M+H]$^+$.

Intermediate 7

1-(5-nitro-2-phenoxybenzyl)-1H-1,2,4-triazole

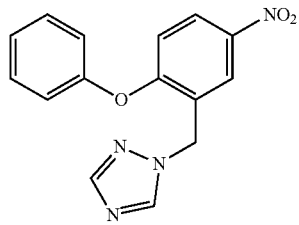 [SMILES: O=[N+]([O-])c1ccc(Oc2ccccc2)c(Cn2cncn2)c1]

In a RBF previously equipped with a magnetic stirrer and nitrogen balloon was taken 1,2,4-triazole (0.53 g, 7.7 mmol) in DMF (12 ml). The solution was cooled to 0° C. and NaH (95%, 0.18 g, 7.7 mmol) was added portion wise. The reaction mixture was stirred at 0° C. for 1 h. 2-(bromomethyl)-4-nitro-1-phenoxybenzene (commercially available, 1.2 g, 3.8 mmol) was added drop wise to the reaction mixture at 0° C. and reaction mixture was stirred at room temperature for 30 min. The solvent was evaporated under reduced pressure and the reaction mixture was quenched with ice-water (30 ml) and product was extracted with ethyl acetate (3×30 ml). The combined organic layer was washed with brine (20 ml), dried over sodium sulphate and the solvent removed under reduced pressure. The crude product was purified by combi-flash column chromatography and 50% ethyl acetate in hexanes as an eluent to obtain 0.570 g (49% yield) of the title compound. $^1$H NMR (400 MHz, DMSO-d$_6$): δ 8.70 (s, 1H), 8.22-7.19 (m, 2H), 8.05 (s, 1H), 7.51 (t, J=8.0 Hz, 2H), 7.33 (t, J=7.6 Hz, 1H), 7.11 (d, J=8.0 Hz, 2H), 6.87 (d, J=9.2 Hz, 1H), 5.68 (s, 2H); MS (ES+) m/z 297 [M+H]$^+$ Intermediate 8

4-phenoxy-3-(1H-1,2,4-triazol-1-ylmethyl)aniline

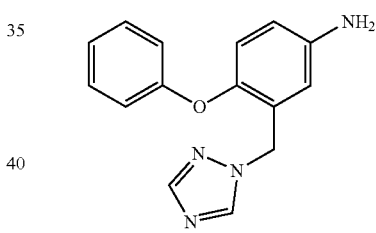

In a RBF previously equipped with a magnetic stirrer and nitrogen balloon was taken 1-(5-nitro-2-phenoxybenzyl)-1H-1,2,4-triazole (Intermediate 7, 0.54 g, 1.8 mmol) and SnCl$_2$·2H$_2$O (1.64 g, 7.2 mmol) in Ethanol (5.4 ml) and the mixture was cooled to 0° C. 35% aq. HCl (0.54 ml) was added and the reaction mixture was stirred at 70° C. for 3 h. The reaction mixture was diluted with ethyl acetate (25 ml) and basified with aq. ammonia to maintain pH 7-8. The mixture was filtered through a Celite® bed and the bed was washed with ethyl acetate (2×25 ml). The combined filtrate was washed with water (3×25 ml) followed by the washing with brine (25 ml), dried over sodium sulphate and the solvent removed under reduce pressure to obtain 0.430 g (88% yield) of the title compound. $^1$H NMR (400 MHz, DMSO-d$_6$): δ 8.43 (s, 1H), 7.95 (s, 1H), 7.31 (t, J=7.6 Hz, 2H), 7.02 (t, J=7.2 Hz, 1H), 6.83 (d, J=8.0 Hz, 2H), 6.72 (d, J=8.8 Hz, 1H), 6.56 (dd, J=8.8, 2.4 Hz, 1H), 6.36 (d, J=2.0 Hz, 1H), 5.21 (s, 2H), 5.12 (s, 2H); MS (ES+) m/z 267 [M+H]$^+$ Intermediate 9
1-[4-phenoxy-3-(1H-1,2,4-triazol-1-ylmethyl)phenyl]-3-phenylurea

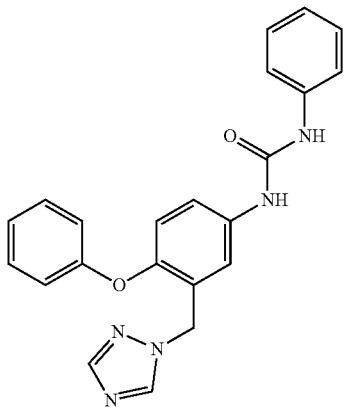 [SMILES: O=C(Nc1ccccc1)Nc1ccc(Oc2ccccc2)c(Cn2cncn2)c1]

In a RBF previously equipped with a magnetic stirrer was taken 4-phenoxy-3-(1H-1,2,4-triazol-1-ylmethyl)aniline (Intermediate 8, 0.28 g, 1.0 mmol) and TEA (0.29 ml, 2.1 mmol) in DCM (2.8 ml) and the mixture was cooled to 0° C. Phenyl isocyanate (0.12 g, 1.0 mmol) was added and the reaction mixture was allowed to reach 25° C. and stirred for 16 h. The obtained solid precipitates were filtered out and washed with n-pentane (30 ml) to yield 0.300 g, (74% yield) of the title compound. $^1$H NMR (400 MHz, DMSO-$d_6$): δ 8.74 (s, 1H), 8.61 (s, 1H), 8.53 (s, 1H), 7.99 (s, 1H), 7.48-7.43 (m, 3H), 7.37 (t, J=8.0 Hz, 2H), 7.28 (t, J=8.0 Hz, 3H), 7.11 (t, J=7.4 Hz, 1H), 6.98 (t, J=7.4 Hz, 1H), 6.92-6.89 (m, 3H), 5.40 (s, 2H); MS (ES+) m/z 386 [M+H]$^+$ Intermediate 10
1-[2-(4-ethylphenoxy)-5-nitrobenzyl]-1H-pyrazole

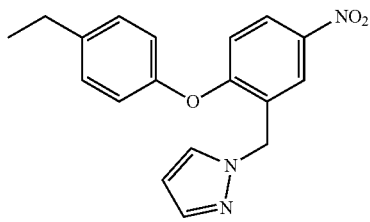 [SMILES: CCc1ccc(Oc2ccc([N+](=O)[O-])cc2Cn2cccn2)cc1]

In a RBF previously equipped with a magnetic stirrer and nitrogen balloon was taken pyrazole (0.36 g, 5.3 mmol) in DMF (6 ml). The solution was cooled to 0° C. and NaH (60%, 0.19 g, 5.3 mmol) was added portion wise and reaction mixture was stirred for 1 h. 2-(bromomethyl)-1-(4-ethylphenoxy)-4-nitrobenzene (commercially available, 0.90 g, 2.6 mmol) in DMF (3 ml) was added drop wise to the reaction mixture at 0° C. and reaction mixture was stirred at RT for 30 min. The reaction mixture was quenched with ice-water (20 ml) and product was extracted with ethyl acetate (3×20 ml). The combined organic layer was washed with brine (20 ml), dried over sodium sulphate and the solvent was evaporated under reduced. The crude product was purified by combi-flash column chromatography and 8% ethyl acetate in hexanes as an eluent to obtain 0.710 g (82% yield) of the title compound. $^1$H NMR (400 MHz, DMSO-$d_6$): δ 8.16 (dd, J=9.2, 2.8 Hz, 1H), 7.92 (d, J=2.0 Hz, 1H), 7.84 (d, J=2.8 Hz, 1H), 7.57 (d, J=1.2 Hz, 1H), 7.36 (d, J=8.4 Hz, 2H), 7.08 (d, J=8.4 Hz, 2H), 6.84 (d, J=8.8 Hz, 1H), 6.35 (t, J=2.1 Hz, 1H), 5.58 (s, 2H), 2.66 (q, J=7.6 Hz, 2H), 1.22 (t, J=7.6 Hz, 3H); MS (ES+) m/z 324 [M+H]$^+$ Intermediate 11
4-(4-ethylphenoxy)-3-(1H-pyrazol-1-ylmethyl)aniline

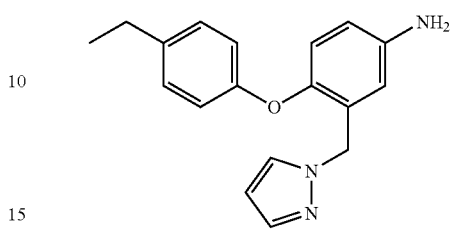

In a RBF previously equipped with a magnetic stirrer was taken 1-[2-(4-ethylphenoxy)-5-nitrobenzyl]-1H-pyrazole (Intermediate 10, 0.70 g, 2.1 mmol) and SnCl$_2$·2H$_2$O (1.95 g, 8.6 mmol) in Ethanol (7.0 ml) and the mixture was cooled to 0° C. 35% aq. HCl (0.70 ml) was added and the reaction mixture was stirred at 70° C. for 3 h. The reaction mixture was diluted with ethyl acetate (20 ml) and basified with ammonia to maintain pH 7-8. The mixture was filtered through a celite bed and washed with ethyl acetate (2×20 ml). The filtrate was washed with water (3×20 ml) followed brine (25 ml), dried over sodium sulphate and the solvent removed under reduce pressure to obtain 0.55 g (86% yield) of the title compound. $^1$H NMR (400 MHz, DMSO-$d_6$): δ 7.63 (d, J=2.0 Hz, 1H), 7.45 (d, J=1.2 Hz, 1H), 7.16 (d, J=8.4 Hz, 2H), 6.79 (d, J=8.8 Hz, 2H), 6.70 (d, J=8.4 Hz, 1H), 6.52 (dd, J=8.4, 2.8 Hz, 1H), 6.25 (d, J=2.0 Hz, 2H), 5.13 (s, 2H), 5.04 (s, 2H), 2.59 (q, J=7.6 Hz, 2H), 1.16 (t, J=7.6 Hz, 3H). MS (ES+) m/z 294 [M+H]$^+$ Intermediate 12
1-[4-(4-ethylphenoxy)-3-(1H-pyrazol-1-ylmethyl)phenyl]-3-methylurea

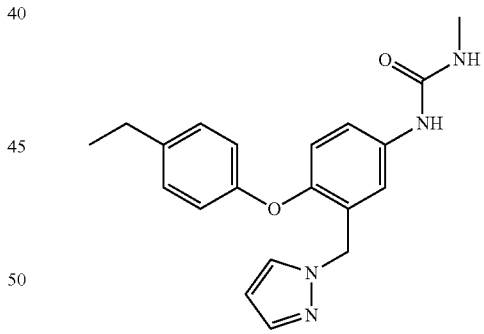

In a 25 ml RBF previously equipped with a magnetic stirrer and nitrogen balloon was taken 4-(4-ethylphenoxy)-3-(1H-pyrazol-1-ylmethyl)aniline (Intermediate 11, 0.50 g, 1.7 mmol) and TEA (0.71 ml, 5.1 mmol) in DCM (5.0 ml) and the mixture was cooled to 0° C. Methylaminoformyl chloride (0.25 g, 2.7 mmol) was added and the reaction mixture was allowed to reach 25° C. and stirred for 16 h. The solvent was evaporated and the reaction mixture was quenched with ice-water (20 ml) and extracted with ethyl Acetate (3×20 ml). The combined organic layer was washed with brine (20 ml), dried over sodium sulphate and solvent removed under reduced. The crude product was purified by combi-flash column chromatography and 35% ethyl acetate in hexanes as an eluent to obtain 0.300 g (50% yield) of the title compound. ¹H NMR (400 MHz, DMSO-d₆): δ 8.51 (s, 1H), 7.70 (d, J=1.6 Hz, 1H), 7.47 (d, J=1.2 Hz, 1H) 7.43 (dd, J=8.8, 2.4 Hz, 1H), 7.20 (m, 2H), 7.02 (d, J=2.0 Hz, 1H), 6.85-6.80 (m, 3H), 6.27 (s, 1H), 5.92 (d, J=4.4 Hz, 1H), 5.27 (s, 2H), 2.63 (s, 3H), 2.59 (q, J=7.6 Hz, 2H), 1.18 (t, J=7.6 Hz, 3H); MS (ES+) m/z 351 [M+H]⁺

Intermediate 13

1-[(4-nitrobiphenyl-2-yl)methyl]-1H-pyrazole

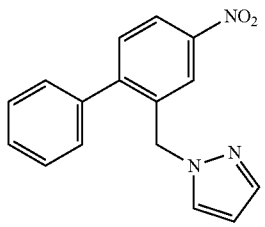

In a 50 ml RBF previously equipped with a magnetic stirrer and nitrogen balloon, pyrazole (0.60 g, 8.8 mmol) in DMF (10 ml) was added. The solution was cooled to 0° C. and NaH (60%, 0.32 g, 8.8 mmol) was added portion wise and the reaction mixture was stirred for 1 h. 2-(bromomethyl)-4-nitrobiphenyl (Iihama, T.; Fu, J. M.; Bourguignon, M.; Snieckus, V. Synthesis (1989), 3, 184-8)(1.30 g, 4.4 mmol) in DMF (3 ml) was added drop wise to the reaction mixture at 0° C. and stirred at RT for 30 min. The reaction mixture was quenched with ice-water (30 ml) and product was extracted with ethyl acetate (3×30 ml). The combined organic layer was washed with brine (20 ml), dried over sodium sulphate and the solvent evaporated under reduced pressure. The crude product was purified by combi-flash column chromatography using 50% ethyl acetate in hexanes as an eluent to obtain 1.1 g (88% yield) of the title compound. ¹H NMR (400 MHz, DMSO-d₆): δ 8.22 (dd, J=8.5, 2.5 Hz, 1H), 7.75 (dd, J=10.7, 2.4 Hz, 2H), 7.59-7.48 (m, 7H), 6.31 (s, 1H), 5.44 (s, 2H).

Intermediate 14

2-(1H-pyrazol-1-ylmethyl)biphenyl-4-amine

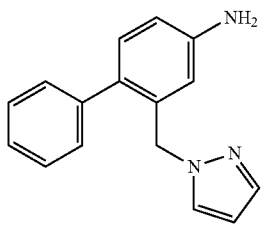 [SMILES: O=[N+]([O-])c1ccc(-c2ccccc2)c(Cn2cccn2)c1]

1-[(4-nitrobiphenyl-2-yl)methyl]-1H-pyrazole (Intermediate 8, 1.10 g, 3.9 mmol) and SnCl₂·2H₂O (3.55 g, 15.7 mmol) in ethanol (11.0 ml) were added to a RBF, previously equipped with a magnetic stirrer and nitrogen balloon, and the mixture was cooled to 0° C. To the resulting suspension, 35% aq. HCl (1.10 ml) was added and the reaction mixture was stirred at 70° C. for 3 h. The reaction mixture was diluted with ethyl acetate (25 ml) and basified with Aq. ammonia to maintain pH 7-8. The mixture was filtered through celite bed and washed with ethyl acetate (2×25 ml). The filtrate was washed with water (3×25 ml) and brine (25 ml), dried over sodium sulphate and the solvent evaporated under reduced pressure to obtain 1.2 g of the title compound. ¹H NMR (400 MHz, DMSO-d₆): δ 7.55 (d, J=2.2 Hz, 1H), 7.45-7.30 (m, 6H), 6.96 (d, J=8.2 Hz, 1H), 6.57 (dd, J=8.2, 2.4 Hz, 1H), 6.25 (d, J=2.0 Hz, 2H), 5.19 (s, 2H), 5.17 (s, 2H); MS (ES+) m/z 250 [M+H]⁺

Intermediate 15

1-methyl-3-[2-(1H-pyrazol-1-ylmethyl)biphenyl-4-yl]urea

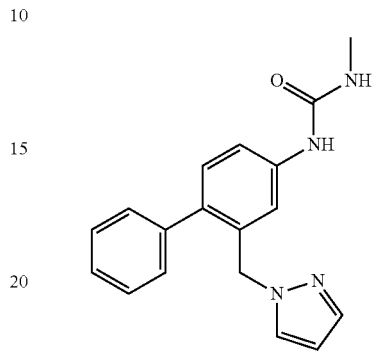

In a RBF previously equipped with a magnetic stirrer and nitrogen balloon was taken (Intermediate 9, 0.50 g, 2 mmol) and TEA (0.84 ml, 6 mmol) in DCM (5 ml) and the mixture was cooled to 0° C. Methylaminoformyl chloride (0.28 g, 3 mmol) was added and the resulting reaction mixture was allowed to reach 25° C. and stirred for 16 h. The solvent was evaporated and the reaction mixture was quenched with ice-water (20 ml) and product was extracted with ethyl acetate (3×20 ml). The combined organic layer was washed with brine (20 ml), dried over sodium sulphate and solvent removed under reduced pressure. The crude product was purified by combi-flash column chromatography using 40% ethyl acetate in hexanes as an eluent to obtain 0.250 g (40% yield) of the title compound. ¹H NMR (400 MHz, DMSO-d₆): δ 8.58 (s, 1H), 7.58-7.53 (m, 2H), 7.47-7.36 (m, 6H), 7.15 (d, J=8.4 Hz, 1H), 6.94 (d, J=1.6 Hz, 1H), 6.25 (t, J=2.0 Hz, 1H), 5.96 (q, J=4.8 Hz, 1H), 5.24 (s, 2H), 2.63 (d, J=4.6 Hz, 3H); MS (ES+) m/z 307 [M+H]⁺

Intermediate 16 methyl 5-{[(3-methylphenyl)carbamoyl]amino}-2-phenoxybenzoate

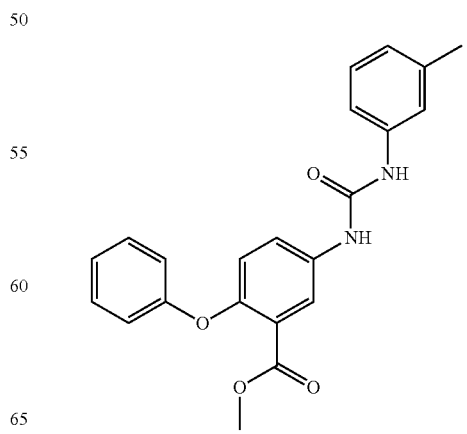

To a RBF previously equipped with a magnetic stirrer and nitrogen balloon was added, 3-methylaniline (1.35 g, 12.6 mmol), NaHCO$_3$ (3.17 g, 37.8 mmol) and DCM (17 ml). The mixture was cooled to 0° C., and triphosgene (1.23 g, 4.1 mmol) was added and reaction mixture was stirred for 2 h at 0° C. Methyl 5-amino-2-phenoxybenzoate (commercially available, 3.08 g, 12.6 mmol) and NaHCO$_3$ (3.17 g, 37.8 mmol) were added to the reaction mixture. The reaction mixture was allowed to reach to 25° C. and stirred for 2 h. The reaction mixture was quenched with water (50 ml) and the product was extracted with DCM (3×50 ml). The combined organic layer was washed with brine (50 ml), dried over sodium sulphate and the solvent removed under reduced pressure and the crude product was purified by column chromatography using silica gel (60-120 mesh) and 30% ethyl acetate in hexanes as an eluent to obtain 4.5 g (94% yield) of the title compound. MS (ES+) m/z 377 [M+H]$^+$ Intermediate 17
3-[3-(hydroxymethyl)-4-phenoxyphenyl]-1-(3-methylphenyl)urea

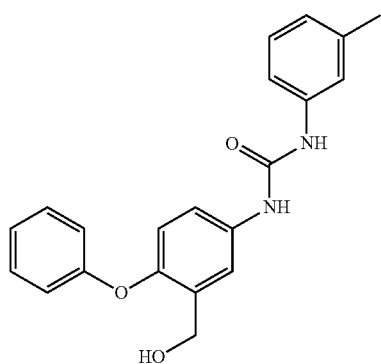

To a RBF previously equipped with a magnetic stirrer and nitrogen balloon was added, methyl 5-{[(3-methylphenyl)carbamoyl]amino}-2-phenoxybenzoate (Intermediate 16, 4.50 g, 11.9 mmol) in THF (45 ml) and the mixture was cooled to 0° C. LiBH$_4$ (1.56 g, 71.7 mmol) was added portion wise at 0° C. The reaction mixture was allowed to reach room temperature and stirred for 4 h. The reaction mixture was quenched with water (50 ml) and the product was extracted with ethylacetate (3×50 ml), dried over sodium sulphate and the solvent removed under reduced pressure. The crude product was triturated by DCM (2×15 ml) and the solid product was collected by filtration to yield 3.9 g (93%) of the title compound. $^1$H NMR (400 MHz, DMSO-d$_6$): δ 8.76 (s, 1H), 8.57 (s, 1H), 7.64 (s, 1H), 7.35-7.40 (m, 4H), 7.33-7.15 (m, 2H), 7.05-7.06 (m, 1H), 6.81-6.79 (m, 4H), 5.21 (d, J=4.80 Hz, 1H), 4.45 (d, J=4.80 Hz, 2H), 2.30 (s, 3H). MS (ES+) m/z 349 [M+H]$^+$ Intermediate 18
3-[3-(chloromethyl)-4-phenoxyphenyl]-1-(3-methylphenyl)urea

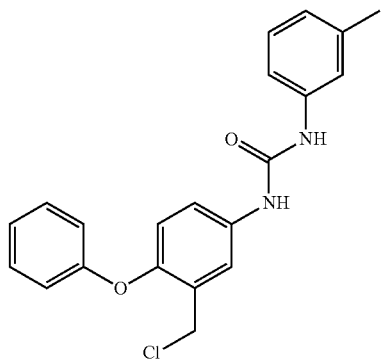 [SMILES: Cc1cccc(NC(=O)Nc2ccc(Oc3ccccc3)c(CCl)c2)c1]

To a RBF previously equipped with a magnetic stirrer and nitrogen balloon was added 3-[3-(hydroxymethyl)-4-phenoxyphenyl]-1-(3-methylphenyl)urea (Intermediate 17, 3.80 g, 10.9 mmol) in dichloromethane (38 ml). A catalytic amount of DMF (0.5 ml) was added and the mixture was cooled to 0° C. and stirred for 10 min at 0° C. Thionyl chloride (2.59 g, 21.8 mmol) was added drop wise and the resulting reaction mixture was allowed to reach room temperature and stirred for 2 h. The reaction mixture was quenched with water (30 ml) and the aqueous layer was extracted with dichloromethane (3×30 ml). The combined organic layer was dried over sodium sulphate and the solvent removed under reduced pressure. The crude product was purified by column chromatography using silica gel (100-200 mesh) and neat hexanes as an eluent to obtain 3.0 g (74% yield) of the title compound. MS (ES+) m/z 367 [M+H]$^+$ Intermediate 19
1-[3-(chloromethyl)-4-phenoxyphenyl]-3-(3-methylphenyl)-1,3,5-triazinane-2,4,6-trione

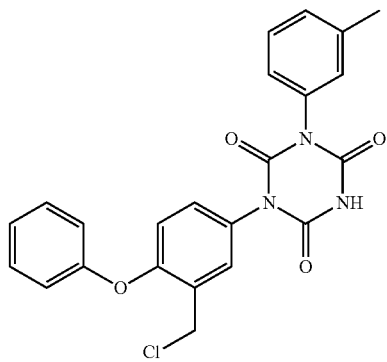 [SMILES: Cc1cccc(-n2c(=O)[nH]c(=O)n(-c3ccc(Oc4ccccc4)c(CCl)c3)c2=O)c1]

To a microwave vial previously equipped with a magnetic stirrer and nitrogen balloon was added 3-[3-(chloromethyl)-4-phenoxyphenyl]-1-(3-methylphenyl)urea (Intermediate 18, 1.00 g, 2.3 mmol) in bromobenzene (10 ml) and the mixture was cooled to 0° C. Ethoxy carbonyl isocyanate (0.53 g, 4.5 mmol) was added and resulting reaction mixture was allowed to reach 25° C. and heated at 150° C. for 3 h in an Anton par microwave synthesizer-300. The reaction mixture was quenched with water (10 ml) and aqueous layer was extracted with ethyl acetate (2×30 ml). The combined organic layer was dried over sodium sulphate and the solvent removed under reduced pressure. The crude product was purified by Combi-flash chromatography and 20% ethyl acetate in hexanes as an eluent to obtain 0.53 g of the crude title compound that was used in the next step without further purification. MS (ES−) m/z 434 [M−H]⁻

Intermediate 20

(5-amino-2-phenoxyphenyl)methanol

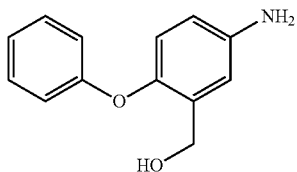 [SMILES: Nc1ccc(Oc2ccccc2)c(CO)c1]

To a RBF previously equipped with a magnetic stirrer and nitrogen balloon was added (5-Nitro-2-phenoxyphenyl) methanol (commercially available, 5.0 g, 20.4 mmol) in methanol (50 ml). Palladium on carbon (10% (50% wet), 1.0 g) was added under $N_2$ atmosphere and the mixture was stirred under $H_2$ (gas) for 4.5 h. The reaction mixture was filtered through a celite bed and washed with methanol. The combined filtrate was evaporated under reduced pressure to yield 4.1 g (93% yield) of the title compound. $^1$H NMR (400 MHz, DMSO-$d_6$): δ 7.27 (t, J=8.00 Hz, 2H), 6.96 (t, J=7.20 Hz, 1H), 6.77 (d, J=7.60 Hz, 3H), 6.65 (d, J=8.40 Hz, 1H), 6.45 (dd, J=2.40, 8.40 Hz, 1H), 5.01-4.98 (m, 3H), 4.29 (d, J=5.60 Hz, 2H); MS (ES+) m/z 216 [M+H]⁺

Intermediate 21

3-[3-(hydroxymethyl)-4-phenoxyphenyl]-1-(4-methoxyphenyl)urea

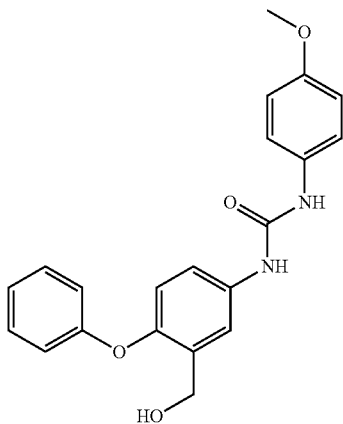 [SMILES: COc1ccc(NC(=O)Nc2ccc(Oc3ccccc3)c(CO)c2)cc1]

To a RBF previously equipped with a magnetic stirrer and nitrogen balloon was added, (5-amino-2-phenoxyphenyl) methanol (Intermediate 20, 1.00 g, 4.65 mmol), NaHCO₃ (1.17 g, 13.95 mmol) and dichloromethane (30 ml). The reaction mixture was cooled to 0° C. and Triphosgene (0.413 g, 1.395 mmol) was added and the reaction mixture was stirred for 2 h at 0° C. 4-methoxy-aniline (0.572 g, 4.65 mmol) and NaHCO₃ (1.17 g, 13.95 mmol) were added and the reaction mixture was allowed to reach room temperature and stirred for 4 h. The reaction mixture was quenched with water (50 ml) and the product was extracted with dichloromethane (3×50 ml). The combined organic layer was washed with brine (100 ml), dried over sodium sulphate and the solvent removed under reduced. The crude product was triturated with n-pentane to yield 2.1 g of the title compound. MS (ES+) m/z 365 [M+H]⁺

Intermediate 22

3-[3-(chloromethyl)-4-phenoxyphenyl]-1-(4-methoxyphenyl)urea

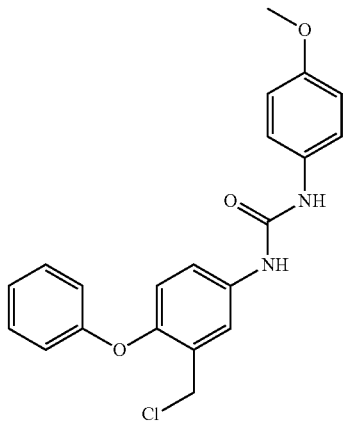 [SMILES: COc1ccc(NC(=O)Nc2ccc(Oc3ccccc3)c(CCl)c2)cc1]

In a RBF previously equipped with a magnetic stirrer and nitrogen balloon was added 3-[3-(hydroxymethyl)-4-phenoxyphenyl]-1-(4-methoxyphenyl)urea (Intermediate 21, 2.1 g, 5.76 mmol) in dichloromethane (21 ml). A catalytic amount of DMF (0.5 ml) was added and the mixture was cooled to 0° C. and stirred for 10 min. Thionyl chloride (0.83 ml, 1.15 mmol) was added drop-wise and the resulting reaction mixture was stirred for 2 h at 25° C. The reaction mixture was quenched with water (30 ml) and the aqueous layer was extracted with dichloromethane (3×30 ml). The combined organic layer was dried over sodium sulphate and the solvent removed under reduced pressure. The residual was purified by column chromatography using silica gel (100-200 mesh) and 9% ethyl acetate in hexane as an eluent to obtain 1.0 g of the crude title compound that was used in the next step without further purification. MS (ES+) m/z 383 [M+H]⁺

Intermediate 23

1-[3-(chloromethyl)-4-phenoxyphenyl]-3-(4-methoxyphenyl)-1,3,5-triazinane-2,4,6-trione

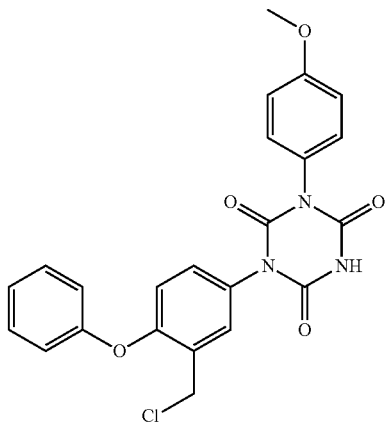 [SMILES: COc1ccc(-n2c(=O)[nH]c(=O)n(-c3ccc(Oc4ccccc4)c(CCl)c3)c2=O)cc1]

To a microwave vial previously equipped with a magnetic stirrer and nitrogen balloon was added 3-[3-(chloromethyl)-

4-phenoxyphenyl]-1-(4-methoxyphenyl)urea (Intermediate 22, 0.500 g, 1.3 mmol) in bromobenzene (5 ml). Ethoxy carbonyl isocyanate (0.603 g, 5.23 mmol) was added and resulting reaction mixture was heated at 150° C. for 3 h in an Anton par microwave synthesizer-300. The solvent was removed under reduced pressure and residual was purified by column chromatography using silica gel (100-200 mesh) and 75% ethyl acetate in hexane as an eluent to obtain 0.1 g of the crude title compound that was used in the next step without further purification. MS (ES−) m/z 450 [M−H]⁻

Intermediate 24

1-{[2-(4-fluorophenoxy)-5-nitrophenyl]methyl}-1H-imidazole

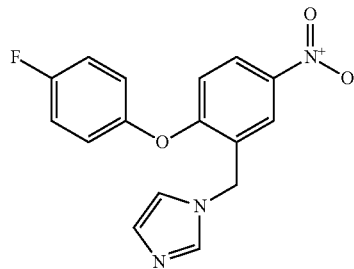

To a RBF previously equipped with a magnetic stirrer and nitrogen balloon was added imidazole (0.50 g, 7.4 mmol) in ACN (33 ml) and the mixture was cooled to 0° C. $K_2CO_3$ (1.02 g, 7.4 mmol) was added and the reaction mixture was stirred for 10 min at 0° C. 2-(Bromomethyl)-1-(4-fluorophenoxy)-4-nitrobenzene (commercially available, 1.1 g, 3.3 mmol)) was added and the reaction mixture was allowed to reach room temperature and stirred for 3 h. The reaction mixture was quenched with water (10 ml) and the aqueous layer was extracted with ethyl acetate (2×20 ml). The combined organic layer was dried over sodium sulphate and the solvent removed under reduced pressure. The crude product was purified by Combi-flash chromatography using 8% MeOH in dichloromethane as an eluent to yield 0.810 g (76% yield) of the title compound. $^1$H NMR (400 MHz, DMSO-$d_6$): δ 8.17 (dd, J=2.80, 8.8 Hz, 1H), 8.09 (d, J=2.80 Hz, 1H), 7.79 (s, 1H), 7.36 (t, J=8.80 Hz, 2H), 7.27 (s, 1H), 7.22-7.18 (m, 2H), 6.95 (s, 1H), 6.86 (d, J=8.80 Hz, 1H), 5.43 (s, 2H); MS (ES+) m/z 315 [M+H]⁺

Intermediate 25

4-(4-fluorophenoxy)-3-[(1H-imidazol-1-yl)methyl]aniline

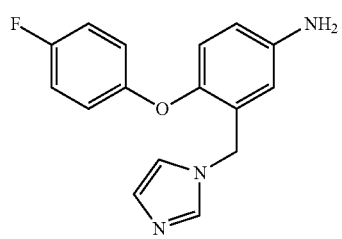 [SMILES: Nc1ccc(Oc2ccc(F)cc2)c(Cn2ccnc2)c1]

To a RBF previously equipped with a magnetic stirrer and nitrogen balloon was added 1-{[2-(4-fluorophenoxy)-5-nitrophenyl]methyl}-1H-imidazole (Intermediate 24, 0.81 g, 2.5 mmol) in Methanol (8.1 ml). Pd/C (10%, (50% wet), 0.08 g) was added under $N_2$ atmosphere and the mixture was stirred under $H_2$ (gas) bubbling. After completion of the reaction, the reaction mixture was filtered through a celite bed and washed with methanol. The solvent was removed under reduced pressure to yield 0.73 g (99% yield) of the title compound. $^1$H NMR (400 MHz, DMSO-$d_6$): δ 7.58 (s, 1H), 7.14 (t, J=8.8 Hz, 2H), 7.05 (s, 1H), 6.87-6.84 (m, 3H), 6.70 (d, J=8.80 Hz, 1H), 6.52 (dd, J=2.40, 8.80 Hz, 1H), 6.33 (d, J=2.40 Hz, 1H), 5.09 (s, 2H), 4.98 (s, 2H); MS (ES+) m/z 284 [M+H]⁺

Intermediate 26

3-[4-(4-fluorophenoxy)-3-[(1H-imidazol-1-yl)methyl]phenyl]-1-(3-methylphenyl)urea

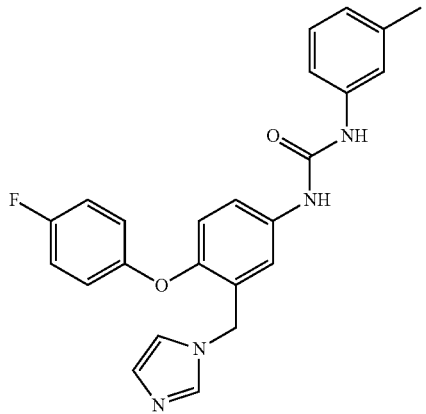 [SMILES: Cc1cccc(NC(=O)Nc2ccc(Oc3ccc(F)cc3)c(Cn3ccnc3)c2)c1]

To a vial previously equipped with a magnetic stirrer and nitrogen balloon was added, 4-(4-fluorophenoxy)-3-[(1H-imidazol-1-yl)methyl]aniline (Intermediate 25, 0.73 g, 2.5 mmol) NaHCO₃ (0.63 g, 7.5 mmol) and dichloromethane (7.3 ml). The mixture was cooled to 0° C. and triphosgene (0.22 g, 0.7 mmol) was added and reaction mixture was stirred for 2 h. 3-methyl-aniline (0.27 g, 2.5 mmol) and NaHCO₃ (0.63 g, 7.5 mmol) were added and the reaction mixture was allowed to reach room temperature and stirred for 3 h. The reaction mixture was diluted with water (25 ml) and extracted with ethyl acetate (3×20 ml). The combined organic layer was dried over sodium sulphate and the solvent was removed under reduced pressure. The crude product was purified by column chromatography using silica gel (100-200 mesh) and 30% ethyl acetate in hexanes as an eluent to obtain 0.43 g (40% yield) of the title compound. $^1$H NMR (400 MHz, DMSO-$d_6$): δ 9.35 (s, 1H), 9.19 (s, 2H), 7.71-7.63 (m, 3H), 7.53 (d, J=2.0 Hz, 1H), 7.30-7.14 (m, 5H), 6.97-6.94 (m, 2H), 6.9 (d, J=8.80 Hz, 1H), 6.80 (d, J=7.20 Hz, 1H), 5.45 (s, 2H), 2.34 (s, 3H). MS (ES+) m/z 417 [M+H]⁺

Intermediate 27
3-(3-hydroxy-4-phenoxyphenyl)-1-(3-methylphenyl)urea

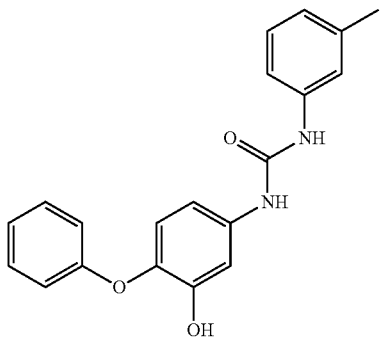 [SMILES: Cc1cccc(NC(=O)Nc2ccc(Oc3ccccc3)c(O)c2)c1]

To a RBF previously equipped with a magnetic stirrer and nitrogen balloon was added 5-Amino-2-phenoxyphenol (commercially available, 2.0 g, 9.9 mmol) in DMF (20 ml) and the mixture was cooled to 0° C. NaHCO$_3$ (2.49 g, 29.7 mmol) was added and the resulting mixture was stirred for 20. 3-Methyl-phenylisocyanate (1.32 g, 9.9 mmol) was added and reaction mixture was stirred at room temperature for 4 h. The reaction mixture was quenched with water (500 ml) and product was extracted with EtOAc (3×100 ml). The combined organic layer was washed with brine (100 ml), dried over sodium sulphate and the solvent removed under reduced pressure. The crude product was triturated with dichloromethane and hexane to obtain 3.5 g of the title compound. MS (ES+) m/z 335 [M+H]$^+$ Intermediate 28
3-[3-(benzyloxy)-4-phenoxyphenyl]-1-(3-methylphenyl)urea

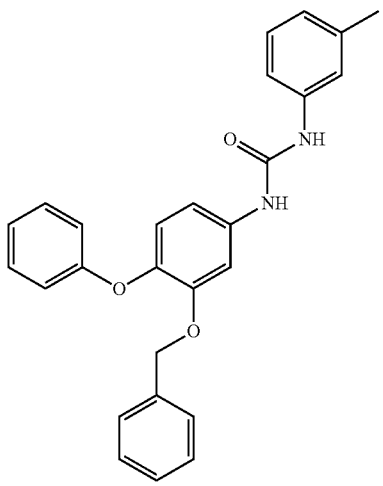 [SMILES: Cc1cccc(NC(=O)Nc2ccc(Oc3ccccc3)c(OCc3ccccc3)c2)c1]

To a RBF previously equipped with a magnetic stirrer and nitrogen balloon was added 3-(3-hydroxy-4-phenoxyphenyl)-1-(3-methylphenyl)urea (Intermediate 27, 3.5 g, 10.47 mmol) and K$_2$CO$_3$ (2.17 g, 15.70 mmol) in DMF (35 ml) and the mixture was cooled to 0° C. Benzyl bromide (2.15 g, 12.57 mmol) was added and the reaction mixture was allowed to reach 25° C. and stirred for 16 h. The reaction mixture was quenched with water (150 ml) and product was extracted with EtOAc (3×100 ml). The combined organic layer was washed with brine (100 ml), dried over sodium sulphate and the solvent removed under reduced pressure. The crude product was purified by column chromatography using silica gel (100-200 mesh) and 30% ethyl acetate in hexane as an eluent to obtain 3.8 g (quantitative) of the title compound. MS (ES+) m/z 425 [M+H]$^+$ Intermediate 29
1-[3-(benzyloxy)-4-phenoxyphenyl]-3-(3-methylphenyl)-1,3,5-triazinane-2,4,6-trione

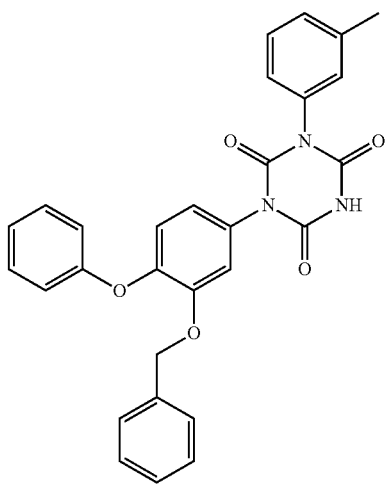 [SMILES: Cc1cccc(-n2c(=O)[nH]c(=O)n(-c3ccc(Oc4ccccc4)c(OCc4ccccc4)c3)c2=O)c1]

To a microwave vial previously equipped with a magnetic stirrer and nitrogen balloon was added 3-[3-(benzyloxy)-4-phenoxyphenyl]-1-(3-methylphenyl)urea (Intermediate 28, 1.0 g, 2.35 mmol) in Chlorobenzene (10 ml). Ethoxy carbonyl isocyanate (1.08 g, 9.4 mmol) was added and the reaction mixture was heated at 130° C. for 16 h. The solvent was evaporated under reduce pressure to obtain crude product. The crude product was purified by column chromatography using silica gel (100-200 mesh) and 50% ethyl acetate in hexanes as an eluent to obtain 1.2 g of the title compound. MS (ES−) m/z 492 [M−H]$^-$ Intermediate 30
1-(3-hydroxy-4-phenoxyphenyl)-3-(3-methylphenyl)-1,3,5-triazinane-2,4,6-trione

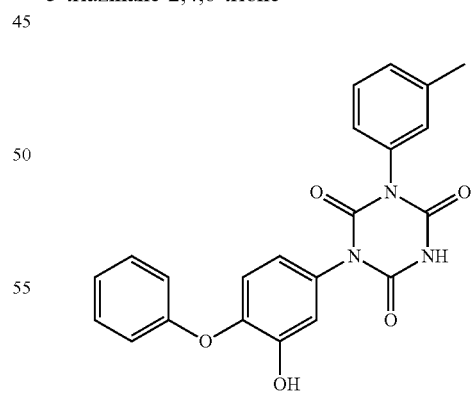

To a RBF previously equipped with a magnetic stirrer and nitrogen balloon was added 1-[3-(benzyloxy)-4-phenoxyphenyl]-3-(3-methylphenyl)-1,3,5-triazinane-2,4,6-trione (Intermediate 29, 1.2 g, 2.43 mmol) in Methanol (12 ml). Pd/C (10% (50% wet), 0.24 g) was added under N$_2$ atmosphere. The mixture was stirred under H$_2$ (gas). After completion of the reaction, reaction mixture was filtered through celite bed washed with methanol and solvent was removed under reduced pressure to obtain 0.271 g (27% yield) product. MS (ES+) m/z 404 [M+H]+

Intermediate 31

1-(2-fluoro-5-nitrophenyl)-4-methyl-1H-imidazole

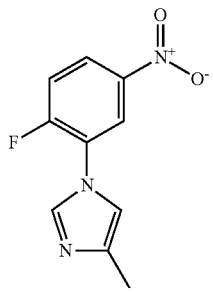 [SMILES: Cc1cn(-c2cc([N+](=O)[O-])ccc2F)cn1]

To a RBF previously equipped with a magnetic stirrer and nitrogen balloon was added, Formic Acid (46.0 g, 480 mmol) and cooled to 0° C. Acetic anhydride (12.42 g, 121 mmol) was added drop-wise at 0° C. and the mixture stirred for 30 min. In another RBF previously equipped with a magnetic stirrer and nitrogen balloon 2-Fluoro-5-nitroaniline (5.0 g, 32.0 mmol) was dissolved in THF (50 ml) and the solution was cooled to 0° C. To this mixture, above the Formic Acid/Acetic anhydride reaction mixture was added at 0° C. The resulting reaction mixture was allowed to reach room temperature and stirred at 60° C. for 16 h. The reaction mixture was quenched with water (100 ml) and product was extracted with EtOAc (3×100 ml). The combined organic layer was washed with brine (75 ml), dried over sodium sulphate and the solvent removed under reduce pressure to obtain 9.01 g of crude 2-Fluoro-1-(formylamino)-5-nitrobenzene. This crude 2-Fluoro-1-(formylamino)-5-nitrobenzene (8.2 g, 44.5 mmol), was added to a RBF previously equipped with a magnetic stirrer and nitrogen balloon together with 1-Chloro-2-propanone (10.3 g, 111.3 mmol), Potassium Carbonate (21.55 g, 155.8 mmol) and Potassium Iodide (0.702 g, 4.2 mmol) in DMF (82 ml) at room temperature. The resulting reaction mixture was stirred for 16 h at room temperature. The reaction mixture was quenched with water (250 ml) and product was extracted with EtOAc (3×150 ml). The combined organic layer was washed with brine (100 ml), dried over sodium sulphate and the solvent removed under reduced pressure to obtain 6.2 g of crude N-(2-fluoro-5-nitrophenyl)-N-(2-oxopropyl)formamide. This crude N-(2-fluoro-5-nitrophenyl)-N-(2-oxopropyl)formamide (6.0 g, 24.9 mmol) was added to a RBF previously equipped with a magnetic stirrer and nitrogen balloon together with ammonium acetate (9.6 g, 124.9 mmol) in Acetic Acid (60 ml) and the mixture was heated at 130° C. for 2 h. The reaction mixture was quenched with water (100 ml) and aqueous 50% NaOH solution was added until the pH was basic. The aqueous layer was extracted with EtOAc (3×75 ml). The combined organic layer was washed with brine (100 ml), dried over sodium sulphate and the solvent removed under reduce pressure. The crude product was purified by column chromatography using silica gel (100-200 mesh) and 45% ethyl acetate in hexanes as an eluent to obtain 2.0 g (28% yield) of the title compound. $^1$H NMR (400 MHz, DMSO-$d_6$): δ 8.51 (dd, J=2.80, 6.80 Hz, 1H), 8.31-8.32 (m, 1H), 8.08 (s, 1H), 7.80 (t, J=9.60 Hz, 1H), 7.43 (s, 1H), 2.20 (s, 3H).

Intermediate 32

4-methyl-1-(5-nitro-2-phenoxyphenyl)-1H-imidazole

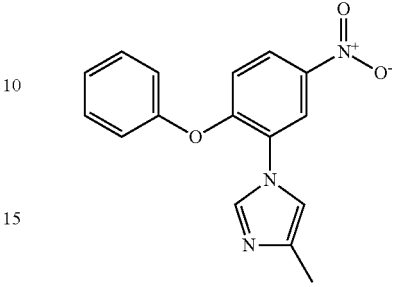

To a microwave vial previously equipped with a magnetic stirrer and nitrogen balloon was added Phenol (0.850 g, 9.0 mmol) and potassium carbonate (2.49 g, 18.0 mmol) in DMF (15 ml) and stirred for 30 min. at room temperature. A solution of 1-(2-fluoro-5-nitrophenyl)-4-methyl-1H-imidazole (Intermediate 31, 2.0 g, 9.0 mmol) in DMF (5 ml) was added drop-wise and the reaction mixture was heated at 100° C. for 16 h. The reaction mixture was quenched with water (100 ml) and extracted with EtOAc (2×150 ml). The combined organic layer was washed with brine (100 ml), dried over sodium sulphate and the solvent removed under reduced. The crude product was purified by column chromatography using silica gel (100-200 mesh) and 50% ethyl acetate in hexanes as an eluent to yield 1.64 g (61% yield) of the title compound. MS (ES+) m/z 296 [M+H]+

Intermediate 33

3-(4-methyl-1H-imidazol-1-yl)-4-phenoxyaniline

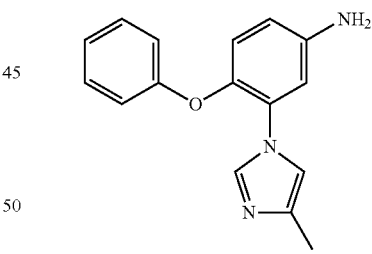

In a 100 ml RBF previously equipped with a magnetic stirrer and nitrogen balloon was taken 4-methyl-1-(5-nitro-2-phenoxyphenyl)-1H-imidazole (Intermediate 32, 1.6 g, 5.4 mmol) in Methanol (60 ml). Pd/C (10% (50% wet), 0.6 g) was added under $N_2$ atmosphere. The suspension was stirred under $H_2$ (gas) bubbling. The completion of reaction was confirmed by the TLC using DCM:MeOH (9:1) as mobile phase. The TLC was visualized using UV light. After completion of the reaction, reaction mixture was filtered through celite bed and washed with methanol. The combined filtrate was concentrated under reduced pressure to yield 1.034 g (71% yield) of the title compound. MS (ES+) m/z 266 [M+H]+

Intermediate 34

N-cyano-N'-[3-(4-methyl-1H-imidazol-1-yl)-4-phenoxyphenyl](methylsulfanyl)methanimidamide

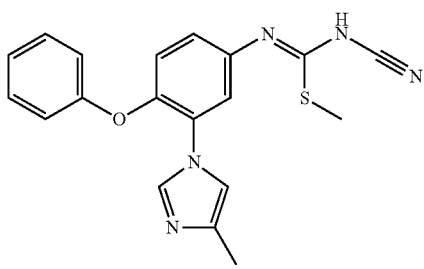 [SMILES: CS/C(=N\c1ccc(Oc2ccccc2)c(-n2cnc(C)c2)c1)NC#N]

In a microwave vial previously equipped with a magnetic stirrer and nitrogen balloon was added 3-(4-methyl-1H-imidazol-1-yl)-4-phenoxyaniline (Intermediate 33, 0.4 g, 1.508 mmol) in Ethanol (6 ml). To this solution [bis(methylsulfanyl)methylidene](cyano)amine (0.22, 1.508 mmol) was added at room temperature. The reaction mixture was heated to 80° C. for 2 days. The completion of reaction was confirmed by the TLC using DCM:MeOH (9:1) as mobile phase. The TLC was visualized using UV light. After completion of the reaction, reaction mixture was cooled to room temperature and the solvent was evaporated under reduced pressure. The crude product was purified by Combiflash chromatography using 8% MeOH in DCM as an eluent to obtain 0.2 g (36%) of the title compound. MS (ES+) m/z 364 [M+H]$^+$ Intermediate 35

3-[5-[3-(4-methyl-1H-imidazol-1-yl)-4-phenoxyphenyl]-1-(3-methylphenyl)-4-(methylsulfanyl)-6-oxo-1,2,5,6-tetrahydro-1,3,5-triazin-2-ylidene]-1-(3-methylphenyl)urea

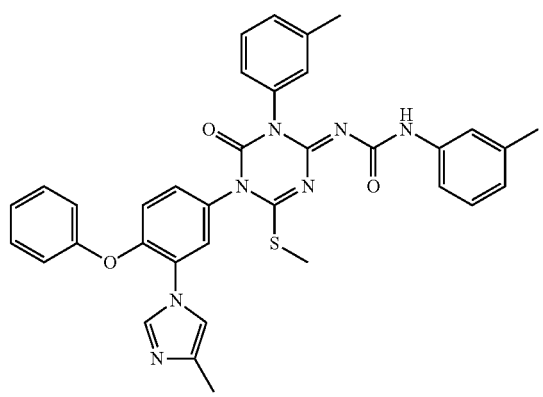 [SMILES: CSc1n/c(=N\C(=O)Nc2cccc(C)c2)n(-c2cccc(C)c2)c(=O)n1-c1ccc(Oc2ccccc2)c(-n2cnc(C)c2)c1]

To a RBF previously equipped with a magnetic stirrer nitrogen balloon was added N-cyano-N'-[3-(4-methyl-1H-imidazol-1-yl)-4-phenoxyphenyl](methylsulfanyl)methanimid amide (Intermediate 34, 0.180 g, 0.49 mmol) and 3-methyl-phenylisocyanate (0.131 g, 0.99 mmol) in DCM (6.0 ml). To the reaction mixture, triethylamine (0.501 g, 4.95 mmol) was added followed by addition of CDI (1,1'-Carbonyldiimidazole, 0.400 g, 2.47 mmol). The reaction mixture was stirred at room temperature for 6 h. The completion of reaction was confirmed by TLC using DCM:MeOH (9.5:0.5) as mobile phase. TLC was visualized using UV light. After completion of the reaction, the reaction mixture was quenched with water (30 ml) and extracted with dichloromethane (2×50 ml). The combined organic layer was washed with brine (30 ml), dried over sodium sulphate and the solvent removed under reduce pressure to obtain 0.140 g crude product which was used in the next step without further purification. MS (ES+) m/z 630 [M+H]$^+$ Intermediate 36 methyl 2-phenoxy-5-[(phenylcarbamoyl)amino]benzoate

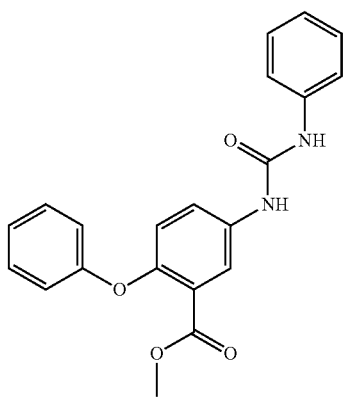 [SMILES: COC(=O)c1cc(NC(=O)Nc2ccccc2)ccc1Oc1ccccc1]

In a RBF previously equipped with a magnetic stirrer and nitrogen balloon was taken, methyl 5-amino-2-phenoxybenzoate (commercially available, 9 g, 37 mmol), NaHCO$_3$ (4.65 g, 0.555 mmol) and DMF (50 ml). The reaction mixture was cooled to 0° C., to it phenylisocyanate (4.05 ml, 37 mmol) was added drop wise and the reaction mixture was stirred for 1 h at room temperature. The reaction mixture was quenched with water (100 ml) and product was extracted with EtOAc (2×100 ml). The combined organic layer was washed with brine (150 ml), dried over sodium sulphate and evaporated under reduced. The crude product was purified by column chromatography using silica gel (60-120 mesh) and 40% ethyl acetate in hexane as an eluent to obtain 9 g (67%) of the title compound. $^1$H NMR (400 MHz, DMSO-d$_6$): δ 8.91 (s, 1H), 8.69 (s, 1H), 8.06 (s, 1H), 7.60 (d, J=8.80 Hz, 1H), 7.45-7.47 (m, 2H), 7.34-7.26 (m, 4H), 7.06-7.05 (m, 2H), 6.98 (t, J=6.80 Hz, 1H), 6.87 (m, 2H), 3.69 (s, 3H). MS (ES+) m/z 366 [M+H]$^+$ Intermediate 37

3-[3-(hydroxymethyl)-4-phenoxyphenyl]-1-phenylurea

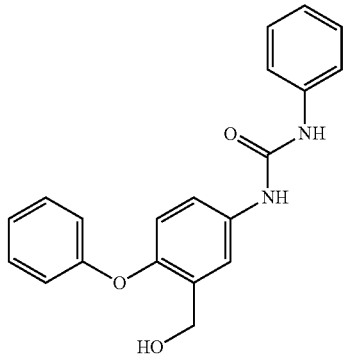 [SMILES: O=C(Nc1ccccc1)Nc1ccc(Oc2ccccc2)c(CO)c1]

In a RBF previously equipped with a magnetic stirrer and nitrogen balloon was taken, methyl 2-phenoxy-5-[(phenylcarbamoyl)amino]benzoate (Intermediate 36, 9 g, 24.8 mmol) in THF (90 ml) and the mixture was cooled to 0° C. To the reaction mixture, LiBH$_4$ (4.33 g, 198.9 mmol) was added portion-wise (4 portion) at 0° C. The reaction mixture was allowed to come to room temperature and stirred at room temperature for 16 h. The reaction mixture was quenched with water (100 ml) and product was extracted with EtOAc (3×100 ml). The combined organic layer was dried over sodium sulphate and evaporated under reduce. The crude product was triturated with 10% EtOAc in hexane (2×50 ml) and solid was collected by filtration to obtain 8.1 g (97%) of the title compound. $^1$H NMR (400 MHz, DMSO-d$_6$): δ 8.73 (s, 1H), 8.60 (s, 1H), 7.61 (s, 1H), 7.46 (d, J=8.0 Hz, 2H), 7.40 (d, J=8.8 Hz, 1H,), 7.34-7.25 (m, 4H), 7.04 (t, J=6.8 Hz, 1H), 6.97-6.96 (m, 1H), 6.87 (m, 3H), 5.20 (s, 1H), 4.43 (m, 2H). MS (ES+) m/z 333 [M+H]$^+$ Intermediate 38
3-[3-(chloromethyl)-4-phenoxyphenyl]-1-phenylurea

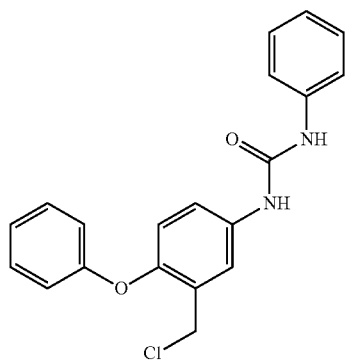 [SMILES: O=C(Nc1ccccc1)Nc1ccc(Oc2ccccc2)c(CCl)c1]

In a RBF previously equipped with a magnetic stirrer and nitrogen balloon was taken 3-[3-(hydroxymethyl)-4-phenoxyphenyl]-1-phenylurea (Intermediate 37, 7.0 g, 20.9 mmol) in DCM (70 ml). A catalytic amount of DMF (0.2 ml) was added and the mixture was cooled to 0° C. and the mixture stirred for 10 min at 0° C. Thionyl chloride (3 ml, 41.9 mmol) was added drop-wise and resulting reaction mixture was allowed to come to room temperature stirred for 2 h. The reaction mixture was quenched with water (70 ml) and aq. layer was extracted with DCM (3×70 ml). The combined organic layer was dried over sodium sulphate and evaporated under reduced pressure and the obtained material was purified by trituration using hexane to produce 7 g of crude title compound that was used in the next step without further purification. $^1$H NMR (400 MHz, DMSO-d$_6$): δ 8.76 (s, 1H), 8.68 (s, 1H), 7.71 (s, 1H), 7.44-7.28 (m, 7H), 7.10 (s, 1H), 6.96-6.87 (m, 4H), 4.70 (s, 2H). MS (ES+) m/z 353 [M+H]$^+$ Intermediate 39
1-[3-(chloromethyl)-4-phenoxyphenyl]-3-phenyl-1,3,5-triazinane-2,4,6-trione

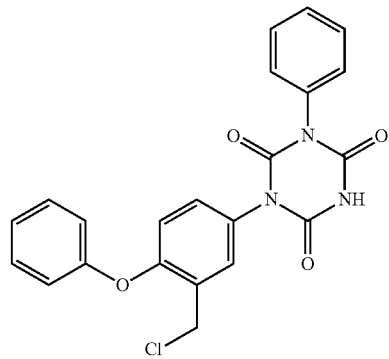 [SMILES: O=c1[nH]c(=O)n(-c2ccc(Oc3ccccc3)c(CCl)c2)c(=O)n1-c1ccccc1]

In a sealed vial previously equipped with a magnetic stirrer and nitrogen balloon was taken 3-[3-(chloromethyl)-4-phenoxyphenyl]-1-phenylurea (Intermediate 38, 3 g, 8.5 mmol) in Bromobenzene (30 ml). Ethoxy carbonyl isocyanate (2.93 g, 25.5 mmol) was added and resulting reaction mixture was heated at 150° C. for 16 h. The solvent was removed under reduced pressure and the crude product was purified by Combi-flash chromatography using silica gel (230-400 mesh) and 40% ethyl acetate in hexane as an eluent to obtain 0.6 g of the crude title compound that was used as without further purification in the next step. MS (ES−) m/z 420 [M−H]$^-$.

Intermediate 40
(1-ethyl-1H-pyrazol-4-yl)(5-nitro-2-phenoxyphenyl)methanol

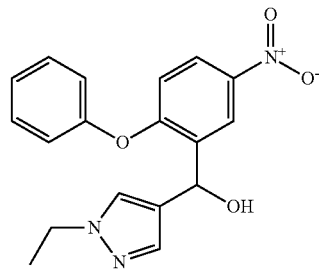 [SMILES: CCn1cc(C(O)c2cc([N+](=O)[O-])ccc2Oc2ccccc2)cn1]

In a RBF previously equipped with a magnetic stirrer and nitrogen balloon was taken 4-bromo-1-ethyl-1H-pyrazole (2.15 g, 12.33 mmol) in THF (15 ml) and the mixture was cooled at −78° C. n-BuLi (2.5 M in THF, 22.4 ml, 13.56 mmol) was added drop-wise to the reaction mixture and it was stirred at same temperature for 2 h. 5-nitro-2-phenoxybenzaldehyde (commercially available, 3.0 g 12.33 mmol) was dissolved in THF (5 ml) and the solution was added drop-wise in to reaction mixture at −78° C. The reaction mixture was stirred at −78° C. for 2 h and then allowed to reach room temperature and stirred for 12 h. The reaction mixture was quenched with ammonium chloride solution (50 ml) and extracted with EtOAc (2×100 ml). The combined organic layer was washed with brine (100 ml) and dried over sodium sulphate and the solvent removed under reduced pressure to obtain 2 g of the crude title compound that that was used in the next step without further purification. MS (ES+) m/z 340 [M+H]$^+$

Intermediate 41

1-ethyl-4-[(5-nitro-2-phenoxyphenyl)methyl]-1H-pyrazole

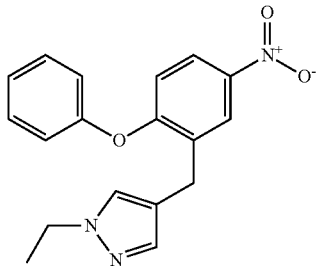 [SMILES: CCn1cc(Cc2cc([N+](=O)[O-])ccc2Oc2ccccc2)cn1]

In a RBF previously equipped with a magnetic stirrer and nitrogen balloon was taken, (1-ethyl-1H-pyrazol-4-yl)(5-nitro-2-phenoxyphenyl)methanol (Intermediate 40, 2.0 g, 5.9 mmol) in DCM (20 ml) and the mixture was cooled to 0° C. Triethyl silane (4.657 g, 40 mmol) was added followed by addition of TFA 18.15 g, 159.2 mmol) at 0° C. The reaction mixture was allowed to reach room temperature and stirred for 3 h. The reaction mixture was quenched with water (30 ml) and extracted with DCM (3×30 ml). The combined organic layer was washed with brine (30 ml), dried over sodium sulphate and the solvent removed under reduced pressure. The crude product was purified by column chromatography using silica gel (60-120 mesh) and 30% ethyl acetate in hexanes as an eluent to obtain 1 g of the title compound. $^1$H NMR (400 MHz, DMSO-$d_6$): δ 8.18 (d, J=2.40 Hz, 1H), 8.08 (dd, J=2.80, 9.00 Hz, 1H), 7.59 (s, 1H), 7.49 (m, 2H), 7.32-7.26 (m, 2H), 7.12 (m, 2H), 6.84 (d, J=8.80 Hz, 1H), 4.06 (m, 2H), 3.67 (s, 2H), 1.31 (m, 3H); MS (ES+) m/z 324 [M+H]$^+$

Intermediate 42

3-[(1-ethyl-1H-pyrazol-4-yl)methyl]-4-phenoxyaniline

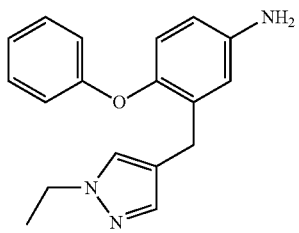 [SMILES: CCn1cc(Cc2cc(N)ccc2Oc2ccccc2)cn1]

In a RBF previously equipped with a magnetic stirrer and nitrogen balloon was taken 1-ethyl-4-[(5-nitro-2-phenoxyphenyl)methyl]-1H-pyrazole (Intermediate 41, 1.0 g, 3.0 mmol) in methanol (10 ml). To the mixture 10% Pd/C (50% wet, 0.2 g) was added under N$_2$ atmosphere. The mixture was stirred for 5 h under H$_2$ (gas) bubbling. The reaction mixture was filtered through celite bed and the bed was washed with Methanol (10 ml) and the combined filtrate was concentrated under reduce pressure to obtain 0.9 g (99%) of the title compound. MS (ES+) m/z 294 [M+H]$^+$

Intermediate 43

3-{3-[(1-ethyl-1H-pyrazol-4-yl)methyl]-4-phenoxyphenyl}-1-phenylurea

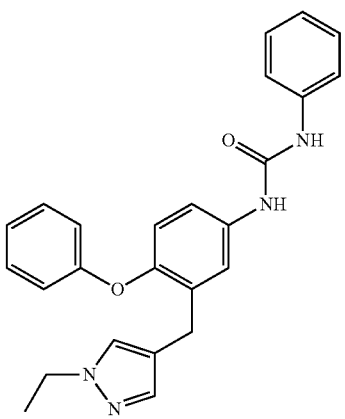 [SMILES: CCn1cc(Cc2cc(NC(=O)Nc3ccccc3)ccc2Oc2ccccc2)cn1]

In a RBF previously equipped with a magnetic stirrer and nitrogen balloon was taken, 3-[(1-ethyl-1H-pyrazol-4-yl)methyl]-4-phenoxyaniline (Intermediate 42, 0.40 g, 1.36 mmol) and NaHCO$_3$ (0.343 g, 4.08 mmol) in DMF (4 ml). The mixture was cooled to 0° C. and phenyl isocyanate (0.162 g, 1.36 mmol) was added drop-wise. The reaction mixture was allowed to reach room temperature and stirred for 2 h. The reaction mixture was quenched with water (30 ml) and aq. layer was extracted with EtOAc (3×30 ml). The combined organic layer was washed with brine (20 ml), the organic layer was dried over sodium sulphate and the solvent removed under reduced pressure. The crude product was triturated by 20% DCM in Hexanes (2×10 ml) and solid was collected by filtration to obtain 0.3 g (53%) of the title compound. MS (ES+) m/z 413 [M+H]$^+$

Intermediate 44 ethyl 2-(5-{[(3-methylphenyl)carbamoyl]amino}-2-phenoxyphenoxy)acetate

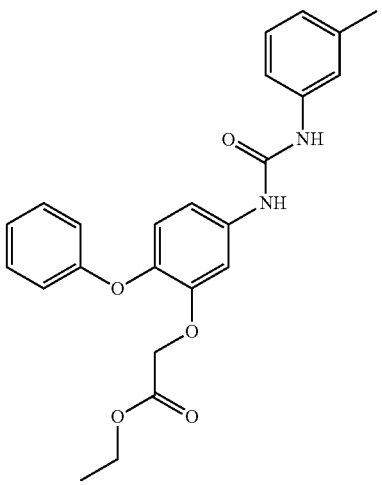 [SMILES: CCOC(=O)COc1cc(NC(=O)Nc2cccc(C)c2)ccc1Oc1ccccc1]

In a RBF previously equipped with a magnetic stirrer and nitrogen balloon was taken 3-(3-hydroxy-4-phenoxyphenyl)-1-(3-methylphenyl)urea (Intermediate 27, 3.00 g, 8.97 mmol) and K₂CO₃ (1.85 g, 13.46 mmol) in DMF (30 ml) and the mixture was cooled to 0° C. To the reaction mixture, BrCH₂COOEt (2.24 g, 13.46 mmol) was added and the resulting reaction mixture was stirred for 16 h at room temperature. The reaction mixture was diluted with ice cold water (100 ml) and extracted with EtOAc (3×50 ml). The combined organic layer was washed with brine (100 ml), dried over sodium sulphate and the solvent removed under reduced pressure. The crude product was purified by column chromatography using silica gel (60-120 mesh) and 20% ethyl acetate in hexane as an eluent to obtain 3.5 g of the title compound. MS (ES+) m/z 421 [M+H]⁺

Intermediate 45 ethyl 2-{5-[3-(3-methylphenyl)-2,4,6-trioxo-1,3,5-triazinan-1-yl]-2-phenoxyphenoxy}acetate

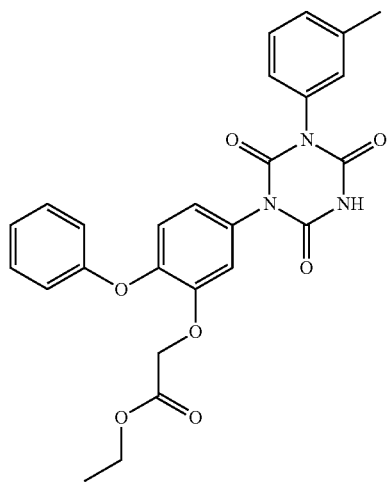 [SMILES: CCOC(=O)COc1cc(-n2c(=O)[nH]c(=O)n(-c3cccc(C)c3)c2=O)ccc1Oc1ccccc1]

In a sealed tube previously equipped with a magnetic stirrer and nitrogen balloon was taken ethyl 2-(5-{[(3-methylphenyl)carbamoyl]amino}-2-phenoxyphenoxy)acetate (Intermediate 44, 3.50 g, 8.32 mmol) in Chlorobenzene (35 ml) and the mixture was cooled to 0° C. Ethoxy carbonyl isocyanate (3.83 g, 33.3 mmol) was added drop-wise and the resulting reaction mixture was allowed to reach room temperature and heated at 150° C. for 16 h. The solvent was removed under reduced pressure and the crude product was purified by column chromatography using silica gel (100-200 mesh) and 70% ethyl acetate in hexanes as an eluent to obtain 1.071 g of the crude title compound that was used in the next step without further purification. MS (ES−) m/z 488 [M−H]⁻.

Intermediate 46

2-{5-[3-(3-methylphenyl)-2,4,6-trioxo-1,3,5-triazinan-1-yl]-2-phenoxyphenoxy}acetic acid

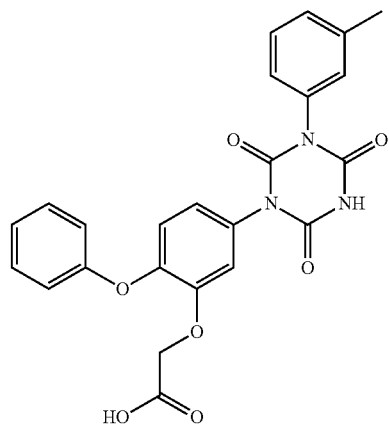 [SMILES: Cc1cccc(-n2c(=O)[nH]c(=O)n(-c3ccc(Oc4ccccc4)c(OCC(=O)O)c3)c2=O)c1]

In a RBF previously equipped with a magnetic stirrer was taken ethyl 2-{5-[3-(3-methylphenyl)-2,4,6-trioxo-1,3,5-triazinan-1-yl]-2-phenoxyphenoxy}acetate (Intermediate 45, 1.0 g) in THF:H₂O (8 ml: 2 ml). LiOH (1.85 g, 13.4 mmol) was added and the resulting reaction mixture was stirred for 1 h at RT. The reaction mixture was concentrated under reduced pressure and the crude mass was diluted with water (5 ml) and extracted with EtOAc (2×10 ml). The aqueous layer was acidified using 1M HCl to pH-3-4 and then again extracted with EtOAc (3×20 ml). The combined organic layer was dried over sodium sulphate and the solvent removed under reduced pressure. The crude product was triturated with DCM and Hexane to obtain the 0.8 g of the title compound. MS (ES−) m/z 460 [M−H]⁻.

Example 1

1-{4-phenoxy-3-[(1H-pyrazol-1-yl)methyl]phenyl}-3-phenyl-1,3,5-triazinane-2,4,6-trione

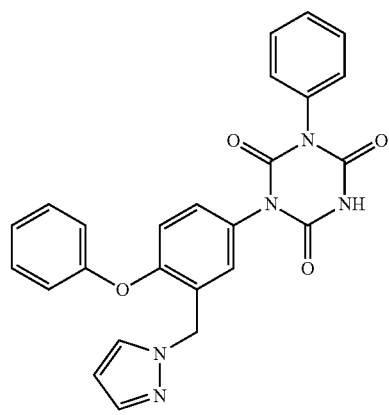 [SMILES: O=c1[nH]c(=O)n(-c2ccc(Oc3ccccc3)c(Cn3cccn3)c2)c(=O)n1-c1ccccc1]

In a microwave tube previously equipped with a magnetic stirrer was taken 1-[4-phenoxy-3-(1H-pyrazol-1-ylmethyl)phenyl]-3-phenylurea (Intermediate 3, 0.15 g, 0.3 mmol) and bromobenzene (1.5 ml). The solution was cooled to 0° C. and Ethoxy carbonyl isocyanate (0.17 g, 1.5 mmol) was added and the reaction mixture was heated at 150° C. for 3 h in a microwave synthesizer. The solvent was evaporated under reduced pressure and the crude product was purified by preparative HPLC (40-100% acetonitrile in water [0.1% formic acid] as mobile phase) to yield 0.015 g (8% yield) of the title compound. $^1$H NMR (400 MHz, DMSO-$d_6$) δ 11.99 (s, 1H), 7.78 (d, J=2.0 Hz, 1H), 7.48-7.35 (m, 8H), 7.30 (dd, J=8.8, 2.4 Hz, 1H), 7.21 (t, J=7.6 Hz, 1H), 7.09-7.05 (m, 3H), 6.88 (d, J=8.4 Hz, 1H), 6.28 (t, J=2.0 Hz, 1H), 5.43 (s, 2H); MS (ES−) m/z 452 [M−H]$^-$.

Example 2

1-{3-[(1H-imidazol-1-yl)methyl]-4-phenoxyphenyl}-3-phenyl-1,3,5-triazinane-2,4,6-trione

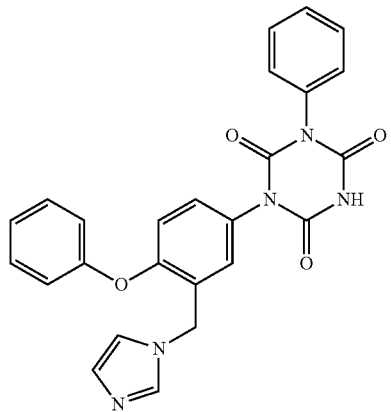 [SMILES: O=c1[nH]c(=O)n(-c2ccc(Oc3ccccc3)c(Cn3ccnc3)c2)c(=O)n1-c1ccccc1]

In a microwave vial previously equipped with a magnetic stirrer was taken 1-[3-(1H-imidazol-1-ylmethyl)-4-phenoxyphenyl]-3-phenylurea (Intermediate 6, 0.18 g, 0.4 mmol) and Bromobenzene (1.8 ml). The solution was cooled to 0° C. and Ethoxy carbonyl isocyanate (0.21 g, 1.8 mmol) was added. The reaction mixture was heated at 150° C. for 3 h in a microwave synthesizer. The solvent was evaporated under reduced pressure and the crude product was purified by preparative HPLC (0-100% acetonitrile in water [0.1% formic acid] as mobile phase) to yield 0.038 g (17% yield) of the title compound. $^1$H NMR (400 MHz, DMSO-$d_6$) δ 12.16 (s, 1H), 8.17 (s, 1H), 7.71 (s, 1H), 7.49-7.31 (m, 7H), 7.25-7.16 (m, 3H), 7.09 (d, J=7.6 Hz, 2H), 6.93-6.88 (m, 2H), 5.32 (s, 2H); MS (ES−) m/z 452 [M−H]$^-$.

Example 3

1-{4-phenoxy-3-[(1H-1,2,4-triazol-1-yl)methyl]phenyl}-3-phenyl-1,3,5-triazinane-2,4,6-trione

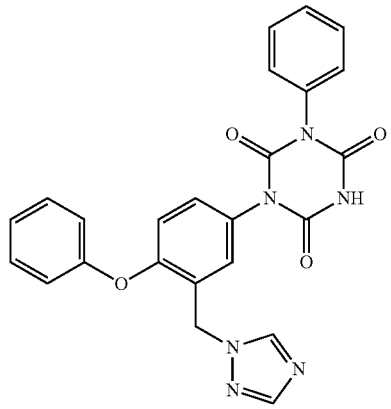 [SMILES: O=c1[nH]c(=O)n(-c2ccc(Oc3ccccc3)c(Cn3cncn3)c2)c(=O)n1-c1ccccc1]

In a microwave tube previously equipped with a magnetic stirrer and nitrogen balloon was taken 1-[4-phenoxy-3-(1H-1,2,4-triazol-1-ylmethyl)phenyl]-3-phenylurea (Intermediate 9, 0.30 g, 0.7 mmol) in Bromobenzene (6.0 ml). The solution was cooled to 0° C. and Ethoxy carbonyl isocyanate (0.35 g, 3.1 mmol) was added to the reaction mixture. The reaction mixture was heated at 150° C. for 3 h in a microwave synthesizer. The solvent was evaporated under reduced pressure to obtain crude product that was purified by preparative HPLC (25-100% acetonitrile in water [0.1% formic acid] as mobile phase) to yield 0.022 g (8% yield) of the title compound. $^1$H NMR (400 MHz, DMSO-$d_6$): δ 12.01 (s, 1H), 8.62 (s, 1H), 8.01 (s, 1H), 7.48-7.32 (m, 8H), 7.25-7.23 (m, 2H), 7.05 (d, J=7.6 Hz, 2H), 6.88 (d, J=8.8, 1H), 5.52 (s, 2H); MS (ES−) m/z 453 [M−H]$^-$.

Example 4

1-[4-(4-ethylphenoxy)-3-[(1H-pyrazol-1-yl)methyl]phenyl]-3-methyl-1,3,5-triazinane-2,4,6-trione

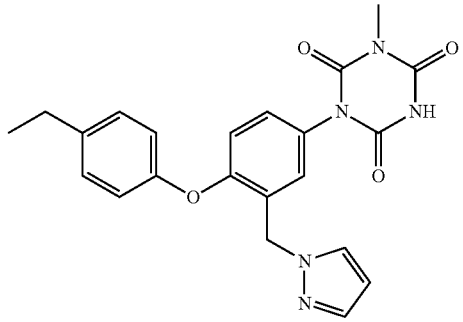 [SMILES: CCc1ccc(Oc2ccc(-n3c(=O)[nH]c(=O)n(C)c3=O)cc2Cn2cccn2)cc1]

In a microwave tube previously equipped with a magnetic stirrer and nitrogen balloon was taken 1-[4-(4-ethylphenoxy)-3-(1H-pyrazol-1-ylmethyl)phenyl]-3-methylurea (Intermediate 12, 0.30 g, 0.8 mmol) in bromobenzene (3.0 ml). The solution was cooled to 0° C. and ethoxy carbonyl isocyanate (0.39 g, 3.4 mmol) was added and the reaction mixture was allowed to reach room temperature and heated at 150° C. for 3 h in a microwave synthesizer. The solvent was evaporated under reduced pressure and the crude product was purified by preparative HPLC (using 40-100% acetonitrile in water [0.1% formic acid] as mobile phase) to yield 0.135 g (37% yield) of the title compound, $^1$H NMR (400 MHz, DMSO-$d_6$): δ 11.80 (s, 1H), 7.80 (d, J=2.0 Hz, 1H), 7.49 (d, J=1.2 Hz, 1H), 7.30 (d, J=8.2 Hz, 2H), 7.22 (dd, J=8.7, 2.6 Hz, 1H), 7.12 (d, J=8.4 Hz, 3H), 6.83 (d, J=8.8 Hz, 1H), 6.29 (s, 1H), 5.43 (s, 2H), 3.12 (s, 3H), 2.63 (q, J=7.6 Hz, 2H), 1.21 (t, J=7.6 Hz, 3H); MS (ES−) m/z 418 [M−H]$^-$.

Example 5

1-methyl-3-{2-[(1H-pyrazol-1-yl)methyl]-[1,1'-biphenyl]-4-yl}-1,3,5-triazinane-2,4,6-trione

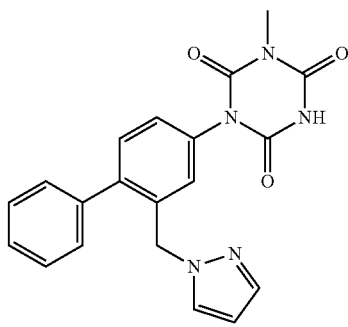 [SMILES: Cn1c(=O)[nH]c(=O)n(-c2ccc(-c3ccccc3)c(Cn3cccn3)c2)c1=O]

Into a microwave tube, previously equipped with a magnetic stirrer and nitrogen balloon, 1-methyl-3-[2-(1H-pyrazol-1-ylmethyl)biphenyl-4-yl]urea (Intermediate 10, 0.25 g, 0.8 mmol) in bromobenzene was added. The solution was cooled to 0° C. and ethoxy carbonyl isocyanate (0.37 g, 3.2 mmol) was added and the resulting reaction mixture was allowed to reach room temperature and heated at 150° C. for 3 h in a microwave synthesizer. The solvent was removed under reduced pressure and the crude product was purified by preparative RP-HPLC (acetonitrile 25-100% in water [0.1% formic acid]) to yield 0.08 g (26% yield) of the title compound. $^1$H NMR (400 MHz, DMSO-$d_6$): δ 11.83 (s, 1H), 7.59-7.46 (m, 7H), 7.43-7.33 (m, 2H), 7.00 (s, 1H), 6.25 (s, 1H), 5.32 (s, 2H), 3.14 (s, 3H); MS (ES−) m/z 374 [M−H]$^-$ Example 6

1-{3-[(1H-imidazol-1-yl)methyl]-4-phenoxyphenyl}-3-(3-methylphenyl)-1,3,5-triazinane-2,4,6-trione

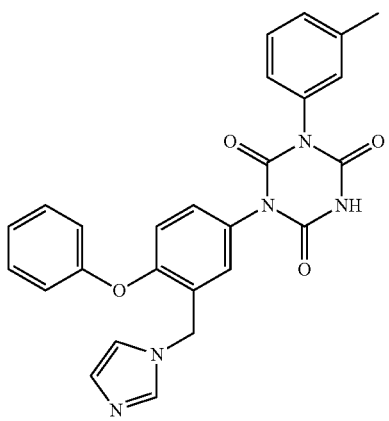 [SMILES: Cc1cccc(-n2c(=O)[nH]c(=O)n(-c3ccc(Oc4ccccc4)c(Cn4ccnc4)c3)c2=O)c1]

To a microwave vial previously equipped with a magnetic stirrer and nitrogen balloon was added imidazole (0.044 g, 0.65 mmol) in acetonitrile (2 ml) and the mixture was cooled to 0° C. K$_2$CO$_3$ (0.089 g, 0.65 mmol) was added and reaction mixture was stirred for 20 min at 0° C. 1-[3-(chloromethyl)-4-phenoxyphenyl]-3-(3-methylphenyl)-1,3,5-triazinane-2,4,6-trione (Intermediate 19, 0.130 g, 0.29 mmol) was added and the resulting reaction mixture was allowed to reach room temperature and then heated to 50° C. for 6 h. The reaction mixture was quenched with water (10 ml) and aq. layer was extracted with ethyl acetate (2×20 ml). The combined organic layer was dried over sodium sulphate and the solvent removed under reduced pressure. The crude product was purified by preparative HPLC (acetonitrile 15-100% in water [0.1% formic acid]) to yield 0.006 g (4% yield) of the title compound. $^1$H NMR (400 MHz, DMSO-$d_6$): δ 12.04 (s, 1H), 7.71 (s, 1H), 7.49-7.42 (m, 2H), 7.37-7.28 (m, 2H), 7.25-7.19 (m, 2H), 7.18-7.11 (m, 4H), 7.10-7.04 (m, 2H), 6.92 (s, 1H), 6.87 (d, J=8.4 Hz, 1H), 5.31 (s, 2H), 2.33 (s, 3H); MS (ES−) m/z 466 [M−H]$^-$ Example 7

1-{3-[(1H-imidazol-1-yl)methyl]-4-phenoxyphenyl}-3-(4-methoxyphenyl)-1,3,5-triazinane-2,4,6-trione

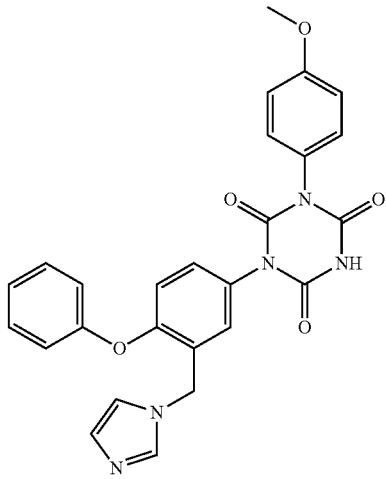 [SMILES: COc1ccc(-n2c(=O)[nH]c(=O)n(-c3ccc(Oc4ccccc4)c(Cn4ccnc4)c3)c2=O)cc1]

In a microwave vial previously equipped with a magnetic stirrer and nitrogen balloon was added imidazole (0.033 g, 0.48 mmol) in actetonitrile (1 ml) and the mixture was cooled to 0° C. K$_2$CO$_3$ (0.067 g, 0.48 mmol) was added and the reaction mixture was stirred for 10 min at 0° C. 1-[3-(chloromethyl)-4-phenoxyphenyl]-3-(4-methoxyphenyl)-1,3,5-triazinane-2,4,6-trione (Intermediate 23, 0.100 g, 0.22 mmol) was added and the resulting reaction mixture allowed to reach room temperature and then heated at 50° C. for 12 h. The reaction mixture was quenched with water (10 ml) and extracted with ethyl acetate (3×10 ml). The combined organic layer was washed with brine (20 ml), dried over sodium sulphate and the solvent removed under reduce. The crude product was purified by preparative HPLC (acetonitrile 15-100% in water [0.1% formic acid]) to yield 0.011 g (10% yield) of the title compound. $^1$H NMR (400 MHz, DMSO-$d_6$): δ 11.93 (s, 1H), 7.72 (s, 1H), 7.53-7.45 (m, 2H), 7.35-7.21 (m, 4H), 7.20-7.15 (m, 2H), 7.14-7.05 (m, 2H), 7.03-6.97 (m, 2H), 6.93 (s, 1H), 6.88 (d, J=8.80 Hz, 1H), 5.31 (s, 2H), 3.36 (s, 3H); MS (ES−) m/z 482 [M−H]$^-$ Example 8

1-[4-(4-fluorophenoxy)-3-[(1H-imidazol-1-yl)methyl]phenyl]-3-(3-methylphenyl)-1,3,5-triazinane-2,4,6-trione

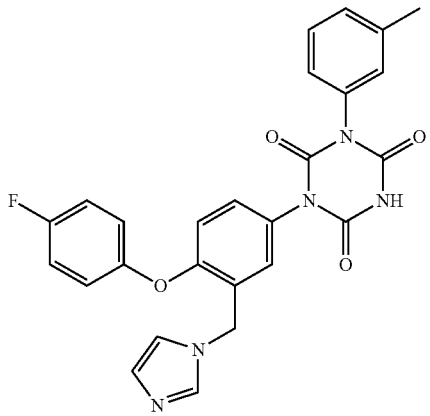 [SMILES: Cc1cccc(-n2c(=O)[nH]c(=O)n(-c3ccc(Oc4ccc(F)cc4)c(Cn4ccnc4)c3)c2=O)c1]

To a microwave vial previously equipped with a magnetic stirrer and nitrogen balloon was added 3-[4-(4-fluorophenoxy)-3-[(1H-imidazol-1-yl)methyl]phenyl]-1-(3-methylphenyl)urea (Intermediate 26, 0.43, 1.0 mmol) in bromobenzene (4.3 ml) and the mixture was cooled to 0° C. Ethoxy carbonyl isocyanate (0.47 g, 4.1 mmol) was added and the reaction mixture was allowed to reach 25° C. and then heated at 150° C. for 3 h in an Anton par microwave synthesizer-300. The reaction mixture was quenched with water (10 ml) and the aqueous layer was extracted with ethyl acetate (30 ml), the organic solvent dried over sodium sulphate and the solvent was removed under reduced pressure. The crude product was purified by preparative HPLC (acetonitrile 5-100% in water [0.1% formic acid]) to yield 0.06 g (1.2% yield) of the title compound. $^1$H NMR (400 MHz, DMSO-d$_6$): δ 12.02 (s, 1H), 7.72 (s, 1H), 7.38-7.29 (m, 4H), 7.25 (d, J=7.60 Hz, 1H), 7.20-7.12 (m, 6H), 6.93 (s, 1H), 6.86 (d, J=8.40 Hz, 1H), 5.33 (s, 2H), 2.34 (s, 3H); MS (ES−) m/z 486 [M−H]$^−$ Example 9

1-{3-[(1H-imidazol-2-yl)methoxy]-4-phenoxyphenyl}-3-(3-methylphenyl)-1,3,5-triazinane-2,4,6-trione

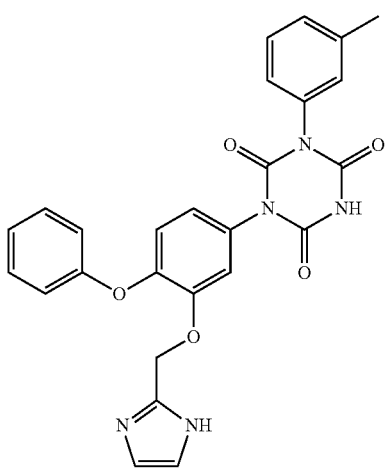 [SMILES: Cc1cccc(-n2c(=O)[nH]c(=O)n(-c3ccc(Oc4ccccc4)c(OCc4ncc[nH]4)c3)c2=O)c1]

To a vial previously equipped with a magnetic stirrer and nitrogen balloon was added 1-(3-hydroxy-4-phenoxyphenyl)-3-(3-methylphenyl)-1,3,5-triazinane-2,4,6-trione (Intermediate 30, 0.070 g, 0.17 mmol) in DMF (0.7 ml) and the mixture was cooled to 0° C. K$_2$CO$_3$ (0.035 g, 0.25 mmol) was added and mixture was stirred for 1 h at 0° C. 2-(Bromomethyl)-1H-imidazole hydrobromide (0.033 g, 0.13 mmol) was added portion-wise and the reaction mixture was allowed to reach room temperature and stirred for 16 h. The reaction mixture was quenched with water (10 ml) and product was extracted with EtOAc (3×10 ml). The combined organic layer was washed with brine (10 ml), dried over sodium sulphate and the solvent removed under reduced pressure. The crude product was purified by preparative HPLC (acetonitrile 35-100% in water [5 mM Ammonium bicarbonate+0.1% NH3]) to yield 0.005 g (5%) of the title compound obtain crude product. $^1$H NMR (400 MHz, DMSO-d$_6$): δ 11.92 (s, 1H), 9.95 (s, 1H), 7.40-7.31 (m, 3H), 7.27 (d, J=7.60 Hz, 1H), 7.23-7.17 (m, 2H), 7.11-6.99 (m, 4H), 6.92-6.81 (m, 4H), 5.03 (s, 2H), 2.35 (s, 3H); MS (ES+) m/z 484 [M+H]$^+$ Example 10

1-{3-[(1H-imidazol-5-yl)methoxy]-4-phenoxyphenyl}-3-(3-methylphenyl)-1,3,5-triazinane-2,4,6-trione

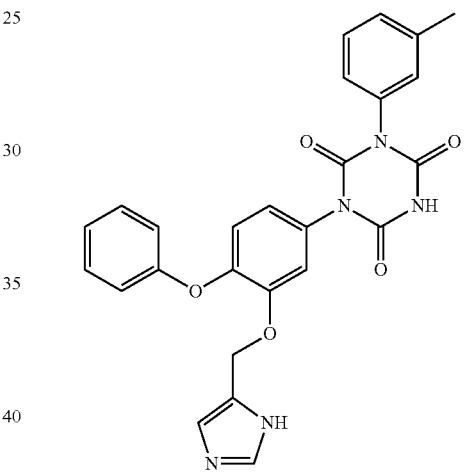

To a vial previously equipped with a magnetic stirrer and nitrogen balloon was added 1-(3-hydroxy-4-phenoxyphenyl)-3-(3-methylphenyl)-1,3,5-triazinane-2,4,6-trione (Intermediate 30, 0.070 g, 0.17 mmol) in DMF (0.7 ml) and the mixture was cooled to 0° C. K$_2$CO$_3$ (0.035 g, 0.26 mmol) was added and the mixture was stirred for 1 h at 0° C. 5-(Chloromethyl)-1H-imidazole (0.026 g, 0.13 mmol) was added portion-wise and the reaction mixture was allowed to reach room temperature and stirred for 16 h. The reaction mixture was quenched with water (10 ml) and product was extracted with EtOAc (3×10 ml). The combined organic layer was washed with brine (10 ml), dried over sodium sulphate and the solvent removed under reduced. The crude product was purified by preparative HPLC (acetonitrile 15-100% in water [0.1% formic acid]) to yield 0.004 g (4% yield) of the title compound. $^1$H NMR (400 MHz, DMSO-d$_6$): δ 11.97 (s, 1H), 9.89 (s, 1H), 7.56 (s, 1H), 7.38-7.31 (m, 3H), 7.29-7.18 (m, 3H), 7.12 (s, 1H), 7.09-6.96 (m, 3H), 6.93-6.70 (m, 3H), 4.91 (s, 2H), 2.34 (s, 3H). MS (ES+) m/z 484 [M+H]$^+$

Example 11

1-{3-[(4-methyl-1H-imidazol-1-yl)methyl]-4-phenoxyphenyl}-3-(3-methylphenyl)-1,3,5-triazinane-2,4,6-trione+1-{3-[(5-methyl-1H-imidazol-1-yl)methyl]-4-phenoxyphenyl}-3-(3-methylphenyl)-1,3,5-triazinane-2,4,6-trione

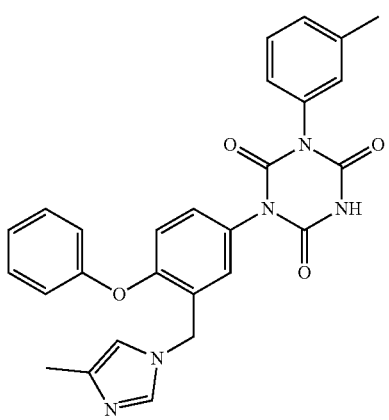

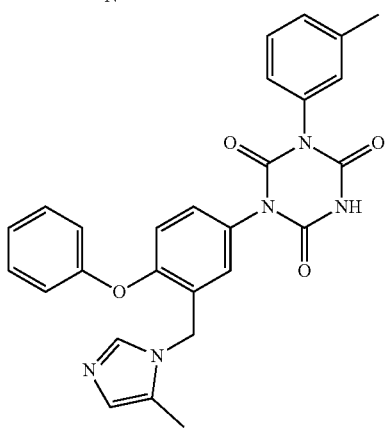

To a 10 ml microwave vial previously equipped with a magnetic stirrer and nitrogen balloon was added 4-Methyl-1H-imidazole (0.04 g, 0.5 mmol) in acetonitrile (1.0 ml) and the mixture was cooled to 0° C. K$_2$CO$_3$ (0.07 g, 0.5 mmol) was added and the mixture was stirred for 10 min at 0° C. 1-[3-(chloromethyl)-4-phenoxyphenyl]-3-(3-methylphenyl)-1,3,5-triazinane-2,4,6-trione (Intermediate 19, 0.10 g, 0.2 mmol) was added and the resulting reaction mixture was allowed to reach room temperature and then heated at 50° C. and stirred for 3 h. The solvent was removed under reduced pressure and the crude product was trituration by Dichloromethane:MeOH (9:1) (2×1 ml) and obtained solid was purified by preparative HPLC (acetonitrile 5-100% in water [0.1% formic acid]) to yield 0.0035 g (3% yield) of a mixture of the two title compounds in approximately 2:1 ratio. $^1$H NMR (400 MHz, DMSO-d$_6$): δ 12.04 (s, 1H), 7.63 (s, 1H), 7.52-7.43 (m, 2H), 7.34-7.22 (m, 5H), 7.20-7.12 (m, 2H), 7.11-7.05 (m, 2H), 6.98-6.84 (m, 2H), 5.25 (s, 1.3H), 5.23 (s. 0.7H), 2.34 (s, 2H), 2.08 (s, 1H); MS (ES−) m/z 480 [M−H]$^−$

Example 12

1-{3-[(4-fluoro-1H-imidazol-1-yl)methyl]-4-phenoxyphenyl}-3-(3-methylphenyl)-1,3,5-triazinane-2,4,6-trione

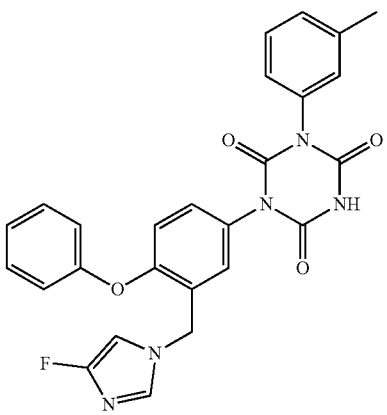 [SMILES: Cc1cccc(-n2c(=O)[nH]c(=O)n(-c3ccc(Oc4ccccc4)c(Cn4cnc(F)c4)c3)c2=O)c1]

In a microwave vial previously equipped with a magnetic stirrer and nitrogen balloon was taken 4-Fluoro-1H-imidazole (0.0325 g, 0.4 mmol) in acetonitrile (1 ml) and the mixture was cooled to 0° C. K$_2$CO$_3$ (0.0653 g, 0.5 mmol) was added and the mixture was stirred for 10 min at 0° C. 1-[3-(chloromethyl)-4-phenoxyphenyl]-3-(3-methylphenyl)-1,3,5-triazinane-2,4,6-trione (Intermediate 19, 0.1 g, 0.2 mmol) was added and the reaction mixture was allowed to reach room temperature and then heated at 50° C. and stirred for 3 h. The solvent was removed under reduced pressure to obtain crude product that was purified by preparative HPLC (acetonitrile 35-100% in water [0.1% formic acid]) to yield 0.003 g (2.7% yield) of the title compound. $^1$H NMR (400 MHz, DMSO-d$_6$): δ 12.01 (s, 1H), 7.49-7.45 (m, 3H), 7.37-7.31 (m, 2H), 7.26-7.22 (m, 3H), 7.20-7.13 (m, 2H), 7.12-7.05 (m, 2H), 6.89 (d, J=8.8, Hz, 1H), 6.85 (d, J=8.4, Hz, 1H), 5.27 (s, 2H), 2.34 (s, 3H); MS (ES+) m/z 486 [M+H]$^+$

Example 13

1-[3-(4-methyl-1H-imidazol-1-yl)-4-phenoxyphenyl]-3-(3-methylphenyl)-1,3,5-triazinane-2,4,6-trione

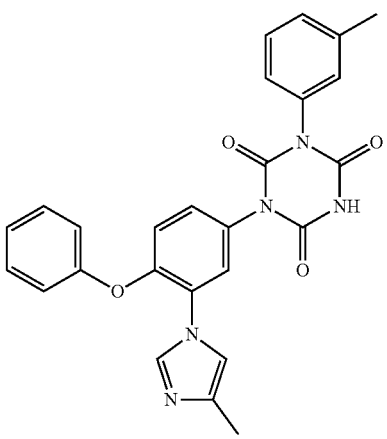

To a RBF previously equipped with a magnetic stirrer and nitrogen balloon was added 3-[5-[3-(4-methyl-1H-imidazol- 1-yl)-4-phenoxyphenyl]-1-(3-methylphenyl)-4-(methylsulfanyl)-6-oxo-1,2,5,6-tetrahydro-1,3,5-triazin-2-ylidene]-1-(3-methylphenyl)urea (Intermediate 35, 0.130 g, 0.20 mmol) in 1,4-Dioxane (3.12 ml). To this solution 2M aq. HCl (2.4 ml) was added and the reaction mixture was heated to 100° C. and stirred for 2 h. The completion of reaction was confirmed by the TLC using DCM:MeOH (9:1) as mobile phase. The TLC was visualized using UV light. After completion of the reaction, the reaction mixture was allowed to reach room temperature and quenched with ice cold water (10 ml) and extracted with dichloromethane (2×20 ml). The combined organic layer was washed with brine (20 ml), dried over sodium sulphate and the solvent removed under reduced pressure. The crude product was purified by preparative HPLC (acetonitrile 25-100% in water [0.1% formic acid]) to yield 0.033 g of the title compound. $^1$H NMR (400 MHz, DMSO-$d_6$): δ 12.1 (s, 1H), 7.99 (s, 1H), 7.64 (s, 1H), 7.43-7.343 (m, 4H), 7.25-7.06 (m, 8H), 2.33 (s, 3H), 2.144 (s, 3H). MS (ES−) m/z 466 [M−H]$^-$ Example 14

1-{3-[(4-fluoro-1H-pyrazol-1-yl)methyl]-4-phenoxyphenyl}-3-phenyl-1,3,5-triazinane-2,4,6-trione

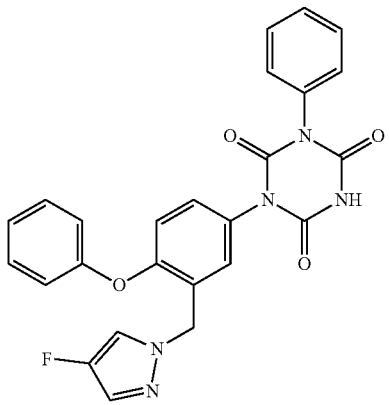 [SMILES: O=c1[nH]c(=O)n(-c2ccc(Oc3ccccc3)c(Cn3cc(F)cn3)c2)c(=O)n1-c1ccccc1]

In a sealed tube previously equipped with a magnetic stirrer and nitrogen balloon was taken 4-Fluoro-1H-pyrazole (0.048 g, 0.56 mmol) in DMF (2 ml) and the mixture was cooled to 0° C. NaH (60%, 0.022 g, 0.56 mmol) was added at 0° C. and the reaction mixture was stirred for 20 min at 0° C. 1-[3-(chloromethyl)-4-phenoxyphenyl]-3-phenyl-1,3,5-triazinane-2,4,6-trione (Intermediate 39, 0.2 g, 0.47 mmol) was added and resulting reaction mixture allowed to come to room temperature. It was then heated to 50° C. for 16 h. The reaction mixture was quenched with water (2 ml) and the solvent removed under reduced pressure and the crude product was purified by preparative HPLC (acetonitrile 20-100% in water [0.1% formic acid]) to yield 0.025 g (11%) of the title compound. $^1$H NMR (400 MHz, DMSO-$d_6$): δ 11.98 (s, 1H), 7.92 (d, J=4.40 Hz, 1H), 7.51 (d, J=4.40 Hz, 1H), 7.48-7.39 (m, 5H), 7.38-7.33 (m, 2H), 7.30 (dd, J=2.00, 8.40 Hz, 1H), 7.21 (t, J=7.20 Hz, 1H), 7.10 (d, J=2.00 Hz, 1H), 7.08-7.03 (m, 2H), 6.87 (d, J=8.40 Hz, 1H), 5.34 (s, 2H); MS (ES−) m/z 470 [M−H]$^-$ Example 15

1-{3-[(4-fluoro-1H-pyrazol-1-yl)methyl]-4-phenoxyphenyl}-3-(3-methylphenyl)-1,3,5-triazinane-2,4,6-trione

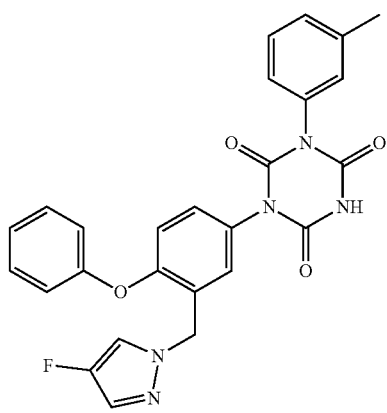 [SMILES: Cc1cccc(-n2c(=O)[nH]c(=O)n(-c3ccc(Oc4ccccc4)c(Cn4cc(F)cn4)c3)c2=O)c1]

In a sealed tube previously equipped with a magnetic stirrer and nitrogen balloon was taken 1-[3-(chloromethyl)-4-phenoxyphenyl]-3-(3-methylphenyl)-1,3,5-triazinane-2,4,6-trione (Intermediate 19, 0.240 g, 0.5 mmol) in ACN and it was cooled to 0° C. To it K$_2$CO$_3$ (0.152 g, 1.1 mmol) was added and the mixture was stirred for 10 min at 0° C. 4-Fluoro-1H-pyrazole (0.056 g, 0.6 mmol) was added and resulting reaction mixture was allowed to reach room temperature and then heated at 50° C. for 2 h. The reaction mixture was quenched with water (10 ml) and aq. layer was extracted with ethyl acetate (3×10 ml). The combined organic layer was dried over sodium sulphate and the solvent removed under reduced pressure. The crude product was purified by flash column chromatography using 4% MeOH in DCM as an eluent to obtain 0.014 g (5%) of the title compound. $^1$H NMR (400 MHz, DMSO-$d_6$): δ 12.03 (s, 1H), 7.92 (d, J=4.40 Hz, 1H), 7.51 (d, J=4.00 Hz, 1H), 7.47-7.41 (m, 2H), 7.35-7.27 (m, 2H), 7.23-7.18 (m, 2H), 7.14-7.09 (m, 3H), 7.08-7.02 (m, 2H), 6.86 (d, J=8.80 Hz, 1H), 5.34 (s, 2H), 2.32 (s, 3H). MS (ES−) m/z 484 [M−H]$^-$ Example 16

1-{3-[(1-ethyl-1H-pyrazol-4-yl)methyl]-4-phenoxyphenyl}-3-phenyl-1,3,5-triazinane-2,4,6-trione

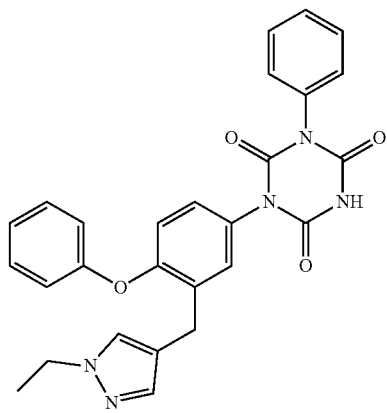 [SMILES: CCn1cc(Cc2cc(-n3c(=O)[nH]c(=O)n(-c4ccccc4)c3=O)ccc2Oc2ccccc2)cn1]

In a microwave vial previously equipped with a magnetic stirrer and nitrogen balloon was taken 3-{3-[(1-ethyl-1H-pyrazol-4-yl)methyl]-4-phenoxyphenyl}-1-phenylurea (Intermediate 43, 0.250 g, 0.60 mmol) in Bromobenzene (2.5 ml) and the mixture was cooled to 0° C. Ethoxy carbonyl isocyanate (0.279 g, 2.42 mmol) was added drop-wise and the resulting reaction mixture was allowed to reach room temperature and heated at 150° C. for 3 h in Anton paar microwave synthesizer-300. The solvent was removed under reduced pressure and the crude product was purified by preparative HPLC (acetonitrile 20-100% in water [5 mM ammonium bicarbonate+0.1% NH3]) to yield 0.030 g (10%) of the title compound. $^1$H NMR (400 MHz, DMSO-d$_6$): δ 11.85 (s, 1H), 7.49-7.34 (m, 8H), 7.27 (s, 1H), 7.22-7.12 (m, 3H), 7.02-6.97 (m, 2H), 6.90 (d, J=8.40 Hz, 1H), 4.01 (q, J=7.20 Hz, 2H), 3.76 (s, 2H), 1.29 (t, J=7.20 Hz, 3H); MS (ES−) m/z 480 [M−H]−

Example 17

1-(3-methylphenyl)-3-{3-[2-oxo-2-(1H-pyrazol-1-yl)ethoxy]-4-phenoxyphenyl}-1,3,5-triazinane-2,4,6-trione

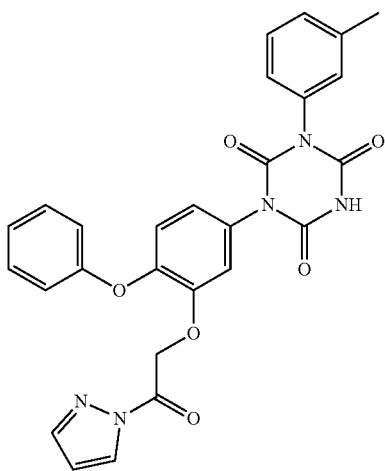 [SMILES: Cc1cccc(-n2c(=O)[nH]c(=O)n(-c3ccc(Oc4ccccc4)c(OCC(=O)n4cccn4)c3)c2=O)c1]

In a vial previously equipped with a magnetic stirrer and nitrogen balloon were taken Intermediate 46, 0.10 g, 0.216 mmol) and pyrazole (0.017 g, 0.26 mmol) in DMF (1 ml). To the mixture EDC. HCl (N-(3-Dimethylaminopropyl)-N'-ethylcarbodiimide hydrochloride, 0.083 g, 0.43 mmol) was added and resulting reaction mixture was stirred for 2 h at room temperature. After that, HOBt (1-Hydroxybenzotriazole, 0.058 g, 0.43 mmol) and N-Methylmorpholine (0.065 g, 0.65 mmol) were added and stirred for 1 h at room temperature. The completion of reaction was confirmed by the TLC using DCM:MeOH (9:1) as mobile phase. The TLC was visualized using UV light. After completion of the reaction, the reaction mixture was kept under cooling condition and purified by to preparative HPLC purification (acetonitrile 30-100% in water [0.1% formic acid]) to yield 0.022 g (19%) of the title compound. $^1$H NMR (400 MHz, DMSO-d$_6$): δ 11.99 (s, 1H), 8.46 (d, J=2.4 Hz, 1H), 7.95 (s, 1H), 7.39-7.33 (m, 3H), 7.30 (s, 1H), 7.24 (d, J=7.60 Hz, 1H), 7.14-7.07 (m, 4H), 7.03-6.99 (m, 3H), 6.67 (s, 1H), 5.58 (s, 2H), 2.34 (s, 3H);); MS (ES−) m/z 510 [M−H]−

Example 18

1-(3-methylphenyl)-3-{4-phenoxy-3-[(1H-pyrazol-1-yl)methyl]phenyl}-1,3,5-triazinane-2,4,6-trione

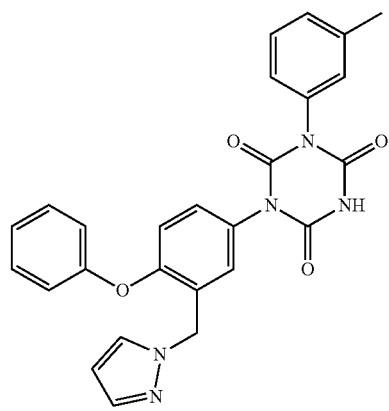 [SMILES: Cc1cccc(-n2c(=O)[nH]c(=O)n(-c3ccc(Oc4ccccc4)c(Cn4cccn4)c3)c2=O)c1]

In a sealed tube previously equipped with a magnetic stirrer and nitrogen balloon was taken pyrazole (0.093 g, 1.3 mmol) in ACN (5.0 ml) and the mixture was cooled to 0° C. K$_2$CO$_3$ (0.317 g, 2.3 mmol) was added and reaction mixture was stirred for 10 min at 0° C. After that, 1-[3-(chloromethyl)-4-phenoxyphenyl]-3-(3-methylphenyl)-1,3,5-triazinane-2,4,6-trione (Intermediate 19, 0.50 g, 1.1 mmol) was added and resulting reaction mixture was allowed to reach room temperature and then heated at 50° C. under stirring for 3 h. The solvent was removed under reduced pressure to obtain the crude product that was purified using RP-HPLC ((acetonitrile 15-100% in water [5 mM ammonium bicarbonate+0.1% NH3]) to yield 0.022 g (4%) of the title compound. $^1$H NMR (400 MHz, DMSO-d$_6$): δ 11.57 (s, 1H), 8.83 (s, 1H), 7.76 (s, 1H), 7.46-42 (m, 3H), 7.31-7.29 (m, 1H), 7.24-7.19 (m, 3H), 7.10-7.03 (m, 4H), 6.86 (d, J=8.40 Hz, 1H), 6.27 (s, 1H), 5.41 (s, 2H), 2.33 (s, 3H); MS (ES−) m/z 465 [M−H]−

Example 19

1-{3-[(4-ethyl-1H-pyrazol-1-yl)methyl]-4-phenoxyphenyl}-3-phenyl-1,3,5-triazinane-2,4,6-trione

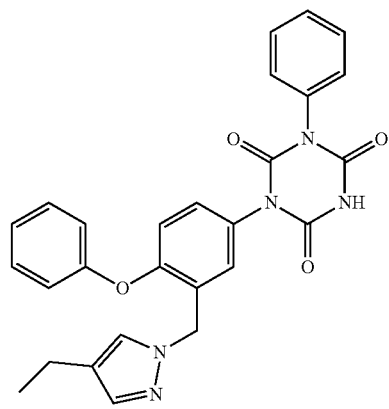 [SMILES: CCc1cnn(Cc2cc(-n3c(=O)[nH]c(=O)n(-c4ccccc4)c3=O)ccc2Oc2ccccc2)c1]

In a sealed tube previously equipped with a magnetic stirrer and nitrogen balloon was taken 4-Ethyl-1H-pyrazole (0.081 g, 0.8 mmol) in DMF (3 ml) and it was cooled to 0° C. NaH (60%, 0.022 g, 0.8 mmol) was added at 0° C. and the reaction mixture was stirred for 20 min at 0° C. 1-[3-(chloromethyl)-4-phenoxyphenyl]-3-phenyl-1,3,5-triazinane-2,4,6-trione (Intermediate 39, 0.3 g, 0.7 mmol) was added to the reaction mixture and resulting reaction mixture was allowed to reach room temperature and then heated to 50° C. for 16 h. The reaction mixture was quenched with water (2 ml) and concentrated under reduced pressure. The crude product was purified by preparative RP-HPLC ((acetonitrile 10-100% in water [5 mM ammonium bicarbonate+ 0.1% NH3]) to yield 0.015 g (4%) of the title compound. $^1$H NMR (400 MHz, DMSO-$d_6$): δ 11.96 (s, 1H), 7.55-7.35 (m, 8H), 7.33-7.10 (m, 4H), 7.03 (m, 2H), 6.88 (d, J=8.40 Hz, 1H), 5.33 (s, 2H), 2.40-2.38 (m, 2H), 1.09 (t, J=7.20 Hz, 3H). MS (ES−) m/z 480 [M−H]$^−$ The following compounds are prepared following analogous procedures to those described above.

Example 20

1-{3-[(4-ethyl-1H-pyrazol-1-yl)methyl]-4-phenoxyphenyl}-3-(3-methylphenyl)-1,3,5-triazinane-2,4,6-trione

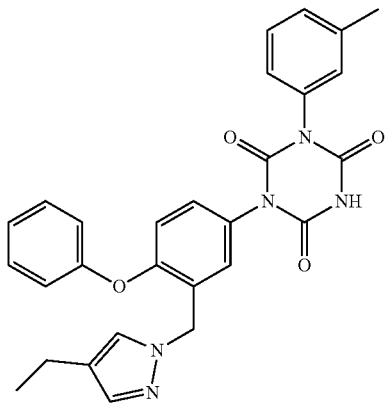 [SMILES: CCc1cnn(Cc2cc(-n3c(=O)[nH]c(=O)n(-c4cccc(C)c4)c3=O)ccc2Oc2ccccc2)c1]

Example 21

1-(3-{[4-(difluoromethyl)-1H-imidazol-1-yl]methyl}-4-phenoxyphenyl)-3-(3-methylphenyl)-1,3,5-triazinane-2,4,6-trione

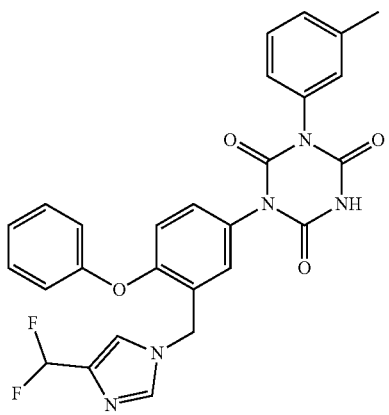 [SMILES: Cc1cccc(-n2c(=O)[nH]c(=O)n(-c3ccc(Oc4ccccc4)c(Cn4cnc(C(F)F)c4)c3)c2=O)c1]

Biological Examples

In Vitro Assay

A high throughput cell-based screen has been used to identify positive modulators of TrkA, TrkB and TrkC. The screen involves the use of cell-based assay overexpressing TrkA, TrkB or TrkC. The purpose of the assay is to identify compounds that modulate neurotrophin signalling (Forsell et al 2012). The assay can be used in inhibitor mode using a high concentration of ligand, in modulator mode using an intermediate concentration and in agonist mode using a low concentration of ligand.

The assay uses Enzyme Fragment Complementation (EFC) technique, which is a proximity-based assay. Briefly, cells used in this assay over-express two fusion proteins, i.e. the receptor, which can be one of TrkA, TrkB or TrkC fused to a small peptide of beta-galactosidase and an adaptor protein, i.e. SHC1 (or any other Trk-adaptor protein) fused to the major part of beta-galactosidase. Ligand binding to the receptor induces phosphorylation of the intracellular domain and hence, recruitment of the adaptor protein to the receptor. The proximity between the small activating peptide on the receptor and the major part of beta-galactosidase on the adaptor protein leads to an active beta-galactosidase enzyme. The activation of the receptor is quantified by measuring the amount of active beta-galactosidase by its conversion of a non-luminescent substrate into a luminescent product.

U2OS-cells, over-expressing TrkA or TrkB or TrkC, were plated in 96- or 384-well plates and incubated overnight. On the following day, test compound was pre-mixed with ligand (NGF) and the ligand-compound mixture is then added to the cells to yield a final ligand concentration of 10 ng/mL. After 3 hours of incubation at room temperature, the incubation is stopped by the addition of a beta-galactosidase substrate mixture containing detergents. The substrate mixture is incubated for 60 minutes at ambient temperature. The luminescence is thereafter read by the use of a plate reader.

Results

Data from these assays for representative compounds is shown in the Table below. The potency is expressed as EC50 (μM) for the individual receptors. The data indicate that the compounds of the invention are expected to possess useful therapeutic properties.

| Example | TrkA | TrkB | TrkC |
|---------|------|------|------|
| 1 | 0.16 | 0.2 | 0.12 |
| 2 | 0.38 | 0.27 | 0.20 |
| 3 | 0.52 | 0.81 | |
| 4 | 1.1 | 2.07 | |
| 5 | 1.32 | 31 | |
| 6 | 0.16 | 0.20 | |
| 7 | 0.72 | 0.45 | |
| 8 | 0.19 | 0.17 | |
| 9 | 0.25 | 0.12 | |
| 10 | 1.67 | 12 | |
| 11 | 0.22 | 0.14 | |
| 12 | 0.10 | 0.06 | |
| 13 | 0.65 | 0.47 | |
| 14 | 0.18 | 0.18 | |
| 15 | 0.12 | 0.09 | |
| 16 | 0.18 | 0.17 | |

The invention claimed is:
1. A compound of formula I,

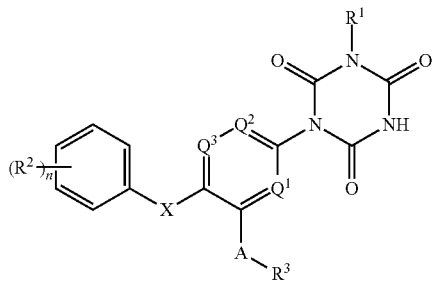

wherein:
$R^1$ represents methyl; phenyl optionally substituted by one or more groups selected from halogen, —CN, —C(O)NR$^{a1}$R$^{a2}$, —NR$^{a3}$R$^{a4}$, a 5-membered heteroaryl group, $C_{1-4}$ alkyl, $C_{1-4}$ alkoxy, $C_{1-4}$ alkoxy-$C_{1-4}$ alkyl or methylenedioxy, wherein the latter four groups are optionally substituted by one or more fluoro groups; or a 5-9-membered heteroaryl group optionally substituted by one or more groups selected from halogen, —CN, $C_{1-4}$ alkyl, $C_{1-4}$ alkoxy, $C_{1-4}$ alkoxy-$C_{1-4}$ alkyl or phenyl, which latter four groups are optionally substituted by one or more fluoro groups;
$R^2$ represents halogen, hydroxy, cyano, —C(O)NR$^{a5}$R$^{a6}$, $C_{1-4}$ alkyl, $C_{1-4}$ alkoxy or $C_{1-4}$ alkoxy-$C_{1-4}$ alkyl, wherein the latter three groups are optionally substituted by one or more fluoro groups;
n represents 0, 1 or 2;
$Q^1$, $Q^2$, and $Q^3$ each represent —C(R$^4$)— or —N—, wherein a maximum of two of $Q^1$ to $Q^3$ represent —N—;
$R^4$ represents H, halogen, $C_{1-4}$ alkyl or $C_{1-4}$ alkoxy which latter two groups are optionally substituted by one or more fluoro group;
X represents —C(R$^5$)(R$^6$)—, —O—, —S—, —N(R$^7$)— or a direct bond;
$R^5$, $R^6$ and $R^7$ each independently represent H or $C_{1-2}$ alkyl;
A represents a direct bond, —O—, $C_{1-2}$ alkylene, —$C_{1-2}$alkyleneO—, —O$C_{1-2}$alkylene-, —N(H)$C_{1-2}$alkylene- or —$C_{1-2}$ alkyleneN(H)—, which latter five groups are optionally substituted by one or more halo, $C_{1-2}$alkyl or =O groups;
$R^3$ represents a 5-6-membered heteroaryl group, optionally substituted by one or more groups selected from halo, —CN, —NR$^{a9}$R$^{a10}$, —C(O)NR$^{a11}$R$^{a12}$, $C_{1-4}$ alkyl, $C_{1-4}$ alkoxy or $C_{1-4}$ alkoxy-$C_{1-4}$ alkyl which latter three groups are optionally substituted by one or more fluoro groups;
$R^{a1}$, $R^{a2}$, $R^{a3}$, $R^{a4}$, $R^{a5}$, $R^{a6}$, $R^{a7}$, $R^{a8}$, $R^{a9}$, $R^{a10}$, $R^{a11}$ and $R^{a12}$ each independently represent H or $C_{1-4}$ alkyl, which $C_{1-4}$ alkyl groups are optionally substituted by one or more fluoro groups; or
$R^{a1}$ and $R^{a2}$, $R^{a3}$ and $R^{a4}$, $R^{a5}$ and $R^{a6}$, $R^{a7}$ and $R^{a8}$, $R^{a9}$ and $R^{a10}$ and $R^{a11}$ and $R^{a12}$ may independently be joined together to form, together with the atom to which they are attached, a 4-to 6-membered heterocyclyl ring, which heterocyclyl ring optionally contains one further heteroatom selected from N, O or S;
or a pharmaceutically-acceptable salt thereof.

2. A compound as claimed in claim 1, wherein $R^1$ represents methyl; or phenyl optionally substituted by one group selected from methyl, methoxy, chloro, fluoro, —OCF$_3$ and methylenedioxy.

3. A compound as claimed in claim 2, wherein $R^1$ represents methyl, phenyl, m-tolyl or p-tolyl.

4. A compound as claimed in claim 1, wherein $R^2$ represents fluoro, chloro, bromo, hydroxy, $C_{1-3}$ alkyl or $C_{1-3}$ alkoxy, wherein the latter two groups are each optionally substituted by one or more fluoro groups.

5. A compound as claimed in claim 1, wherein n represents 0 or 1.

6. A compound as claimed in claim 1, wherein n represents 1 and $R^2$ is in the para-position relative to the point of attachment of the phenyl ring to the X group.

7. A compound as claimed in claim 1, wherein n represents 0.

8. A compound as claimed in claim 1, wherein n represents 1, $R^2$ represents $C_{1-2}$ alkyl or fluoro and $R^2$ is in the para-position relative to the point of attachment of the phenyl ring to the X group.

9. A compound as claimed in claim 1, wherein $Q^3$ represents —N— and $Q^1$ and $Q^2$ each represent —C(R$^4$)— or wherein $Q^1$, $Q^2$ and $Q^3$ each represent —C(R$^4$)—.

10. A compound as claimed in claim 1, wherein $R^4$ represents H, halogen, $C_{1-4}$ alkyl or $C_{1-4}$ alkoxy which latter two groups are optionally substituted by one or more fluoro group.

11. A compound as claimed in claim 1, wherein each $R^4$ group represents H.

12. A compound as claimed claim 1, wherein A represents a direct bond, —O—, $C_{1-2}$ alkylene, -methyleneO—, -Omethylene-, —N(H)methylene- or -methyleneN(H)—, which latter five groups are optionally substituted by one or more halo or $C_{1-2}$ alkyl groups.

13. A compound as claimed in claim 1, wherein A represents —O— or $C_{1-2}$ alkylene optionally substituted by one or more fluoro groups.

14. A compound as claimed in claim 1, wherein A represents methylene optionally substituted by one or more fluoro group.

15. A compound as claimed in claim 1, wherein $R^3$ represents a 5-6-membered heteroaryl group, optionally substituted by one or more groups selected from halo, $C_{1-4}$ alkyl, $C_{1-4}$ alkoxy or —N($C_{1-4}$ alkyl)($C_{1-4}$ alkyl), which latter three groups are optionally substituted by one or more fluoro groups.

16. A compound as claimed in claim 1, wherein $R^3$ represents a 5-6-membered heteroaryl group selected from pyrrolyl, pyazolyl, imidazolyl, triazolyl, tetrazolyl, pyridinyl, pyridazinyl, pyrimidinyl, pyrazinyl and triazinyl, wherein each 5-6-membered heteroaryl group is optionally substituted by one or more fluoro, chloro, bromo, $C_{1-2}$ alkyl, $C_{1-2}$ alkoxy or —N($C_{1-2}$ alkyl)($C_{1-2}$ alkyl) groups, which latter three groups are optionally substituted by one or more fluoro groups.

17. A compound as claimed in claim 1, wherein $R^3$ represents pyrrol-1-yl, pyrazol-1-yl, pyrazol-4-yl, imidazol-1-yl, imidazol-2-yl, imidazol-5-yl or 1,2,4-triazol-1-yl, wherein each 5-membered heteroaryl group is optionally substituted by one or more fluoro, methyl, or ethyl groups, which latter two groups are optionally substituted by one or more fluoro groups.

18. A compound as claimed in claim 17, wherein $R^3$ represents pyrazol-1-yl, imidazol-1-yl, or 1,2,4-triazol-1-yl.

19. A compound as claimed in claim 1, wherein X represents —O— or a direct bond.

20. A compound as claimed in claim 1, wherein $R^{a1}$, $R^{a2}$, $R^{a3}$, $R^{a4}$, $R^{a5}$, $R^{a6}$, $R^{a7}$, $R^{a8}$, $R^{a9}$, $R^{a10}$, $R^{a11}$ and $R^{a12}$ each independently represent H or $C_{1-2}$ alkyl, which $C_{1-2}$ alkyl groups are optionally substituted by one or more fluoro groups.

21. A pharmaceutical composition comprising a compound as defined in claim 1, including pharmaceutically-acceptable salts thereof, in combination with one or more pharmaceutically-acceptable excipient.

22. A method of treating and/or preventing a disease characterised by impaired signalling of neurotrophins and/or other trophic factors, which comprises administering to a patient in need thereof a therapeutically effective amount of a compound as defined in claim 1, including pharmaceutically-acceptable salts thereof.

23. The method of claim 22, wherein the disease characterised by impaired signalling of neurotrophins and/or other trophic factors is selected from Alzheimer's disease, Lewy body dementia, frontotemporal dementia, HIV dementia, Huntington's disease, amyotrophic lateral sclerosis and other motor neurone diseases, Rett syndrome, epilepsy, Parkinson's disease and other parkinsonian disorders, disorders in which enhancement of nerve regeneration is beneficial, spinal cord injury, stroke, hypoxia, ischemia, brain injury including traumatic brain injury, mild cognitive impairment, dementia disorders, including dementia of mixed vascular and degenerative origin, presenile dementia, senile dementia and dementia associated with Parkinson's disease, progressive supranuclear palsy or corticobasal degeneration and cognitive dysfunction in schizophrenia, obesity, diabetes and metabolic syndrome, diabetic neuropathy, painful connective tissue disorders and tendon ruptures, Charcot Marie Tooth disease and its variants, nerve transplantation and its complications, motor neurone disease, peripheral nerve injury, genetic or acquired or traumatic hearing loss, blindness, posterior eye diseases, anterior eye diseases, neurotrophic keratitis, glaucoma, high intraocular pressure, retinitis pigmentosa, obesity, metabolic syndrome, pain, depression, schizophrenia, anxiety cognitive dysfunction and obstructive sleep apnea-hypopnea syndrome.

24. The method of claim 22, wherein the disease characterised by impaired signalling of neurotrophins and/or other trophic factors is selected from the group consisting of Alzheimer's disease, Parkinson's disease, cognitive dysfunction, mild cognitive impairment, obstructive sleep apnea-hypopnea, traumatic brain injury, depression, diabetic neuropathy, and Rett syndrome.

25. The method of claim 22, wherein the disease characterised by impaired signalling of neurotrophins and/or other trophic factors is Alzheimer's disease.

26. A combination product comprising:
(I) a compound as defined in claim 1, or a pharmaceutically acceptable salt thereof; and
(II) one or more other therapeutic agent that is useful in the treatment or prevention of a disease characterised by impaired signalling of neurotrophins and/or other trophic factors, wherein each of components (I) and (II) is formulated in admixture, optionally with a pharmaceutically-acceptable excipient, such as a pharmaceutically-acceptable adjuvant diluent or carrier.

27. A kit-of-parts comprising:
(a) pharmaceutical composition comprising a compound as defined in claim 1, or a pharmaceutically acceptable salt thereof, formulated in admixture with a pharmaceutically-acceptable excipient; and
(b) a pharmaceutical composition comprising one or more other therapeutic agent that is useful in the treatment or prevention of a disease characterised by impaired signalling of neurotrophins and/or other trophic factors, formulated in admixture with a pharmaceutically-acceptable excipient,
which components (a) and (b) are each provided in a form that is suitable for administration in conjunction with the other.

28. A process for the preparation of a compound as defined in claim 1, including a pharmaceutically-acceptable salt thereof, comprising the step of reacting a compound of formula II,

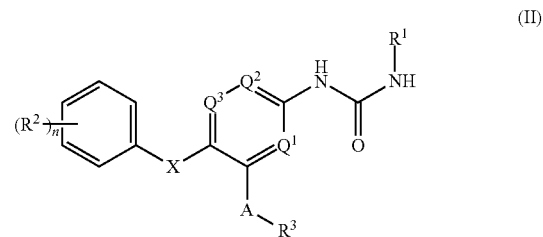

wherein $R^1$, $R^2$, $R^3$, $Q^1$, $Q^2$, $Q^3$, X, A and n are as defined above, with ethoxycarbonyl isocyanate; or
the step of reacting a compound of formula IX

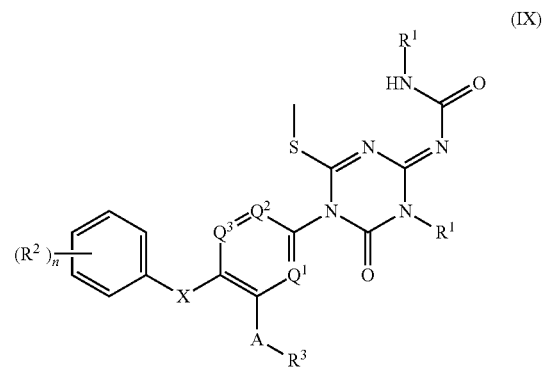

wherein $R^1$, $R^2$, $R^3$, $Q^1$, $Q^2$, $Q^3$, X, A and n are as defined above, in the presence of a suitable acid.

29. A compound as claimed in claim 1, wherein the compound is selected from the group consisting of:
1-{4-phenoxy-3-[(1H-pyrazol-1-yl)methyl]phenyl}-3-phenyl-1,3,5-triazinane-2,4,6-trione;
1-{3-[(1H-imidazol-1-yl)methyl]-4-phenoxyphenyl}-3-phenyl-1,3,5-triazinane-2,4,6-trione;
1-{4-phenoxy-3-[(1H-1,2,4-triazol-1-yl)methyl]phenyl}-3-phenyl-1,3,5-triazinane-2,4,6-trione;
1-[4-(4-ethylphenoxy)-3-[(1H-pyrazol-1-yl)methyl]phenyl]-3-methyl-1,3,5-triazinane-2,4,6-trione;
1-methyl-3-{2-[(1H-pyrazol-1-yl)methyl]-[1,1'-biphenyl]-4-yl}-1,3,5-triazinane-2,4,6-trione;
1-{3-[(1H-imidazol-1-yl)methyl]-4-phenoxyphenyl}-3-(3-methylphenyl)-1,3,5-triazinane-2,4,6-trione;
1-{3-[(1H-imidazol-1-yl)methyl]-4-phenoxyphenyl}-3-(4-methoxyphenyl)-1,3,5-triazinane-2,4,6-trione;
1-[4-(4-fluorophenoxy)-3-[(1H-imidazol-1-yl)methyl]phenyl]-3-(3-methylphenyl)-1,3,5-triazinane-2,4,6-trione;
1-{3-[(1H-imidazol-2-yl)methoxy]-4-phenoxyphenyl}-3-(3-methylphenyl)-1,3,5-triazinane-2,4,6-trione;

1-{3-[(1H-imidazol-5-yl)methoxy]-4-phenoxyphenyl}-3-(3-methylphenyl)-1,3,5-triazinane-2,4,6-trione;

1-{3-[(4-methyl-1H-imidazol-1-yl)methyl]-4-phenoxyphenyl}-3-(3-methylphenyl)-1,3,5-triazinane-2,4,6-trione;

1-{3-[(5-methyl-1H-imidazol-1-yl)methyl]-4-phenoxyphenyl}-3-(3-methylphenyl)-1,3,5-triazinane-2,4,6-trione;

1-{3-[(4-fluoro-1H-imidazol-1-yl)methyl]-4-phenoxyphenyl}-3-(3-methylphenyl)-1,3,5-triazinane-2,4,6-trione;

1-[3-(4-methyl-1H-imidazol-1-yl)-4-phenoxyphenyl]-3-(3-methylphenyl)-1,3,5-triazinane-2,4,6-trione;

1-{3-[(4-fluoro-1H-pyrazol-1-yl)methyl]-4-phenoxyphenyl}-3-phenyl-1,3,5-triazinane-2,4,6-trione;

1-{3-[(4-fluoro-1H-pyrazol-1-yl)methyl]-4-phenoxyphenyl}-3-(3-methylphenyl)-1,3,5-triazinane-2,4,6-trione;

1-{3-[(1-ethyl-1H-pyrazol-4-yl)methyl]-4-phenoxyphenyl}-3-phenyl-1,3,5-triazinane-2,4,6-trione;

1-(3-methylphenyl)-3-{3-[2-oxo-2-(1H-pyrazol-1-yl)ethoxy]-4-phenoxyphenyl}-1,3,5-triazinane-2,4,6-trione;

1-(3-methylphenyl)-3-{4-phenoxy-3-[(1H-pyrazol-1-yl)methyl]phenyl}-1,3,5-triazinane-2,4,6-trione;

1-{3-[(4-ethyl-1H-pyrazol-1-yl)methyl]-4-phenoxyphenyl}-3-phenyl-1,3,5-triazinane-2,4,6-trione;

1-{3-[(4-ethyl-1H-pyrazol-1-yl)methyl]-4-phenoxyphenyl}-3-(3-methylphenyl)-1,3,5-triazinane-2,4,6-trione; and 1-(3-{[4-(difluoromethyl)-1H-imidazol-1-yl]methyl}-4-phenoxyphenyl)-3-(3-methylphenyl)-1,3,5-triazinane-2,4,6-trione;

or a pharmaceutically-acceptable salt thereof.

30. The method as claimed in claim 22, wherein the disease characterised by impaired signalling of neurotrophins and/or other trophic factors is cognitive dysfunction.

31. The method as claimed in claim 22, wherein the disease characterised by impaired signalling of neurotrophins and/or other trophic factors is Parkinson's disease.

32. The method as claimed in claim 22, wherein the disease characterised by impaired signalling of neurotrophins and/or other trophic factors is depression.

33. The method of claim 23, wherein the disorders in which enhancement of nerve regeneration is beneficial are selected from the group consisting of demyelinating diseases and multiple sclerosis, and wherein the diabetic neuropathy related disorder is diabetes-induced osteoporosis.

* * * * *